United States Patent
Douk et al.

(10) Patent No.: US 12,364,385 B2
(45) Date of Patent: Jul. 22, 2025

(54) IMAGING PROBE WITH FLUID PRESSURIZATION ELEMENT

(71) Applicant: Gentuity, LLC, Sudbury, MA (US)

(72) Inventors: Nareak Douk, Lowell, MA (US); Giovanni J. Ughi, Arlington, MA (US); Christopher C. Petroff, Groton, MA (US); Christopher L. Petersen, Carlisle, MA (US); Christopher A. Battles, Seymour, CT (US); R. Maxwell Flaherty, Topsfield, MA (US); J. Christopher Flaherty, Nottingham, NH (US)

(73) Assignee: Gentuity, LLC, Sudbury, MA (US)

( * ) Notice: Subject to any disclaimer, the term of this patent is extended or adjusted under 35 U.S.C. 154(b) by 772 days.

(21) Appl. No.: 17/600,212

(22) PCT Filed: Apr. 30, 2020

(86) PCT No.: PCT/US2020/030616
§ 371 (c)(1),
(2) Date: Sep. 30, 2021

(87) PCT Pub. No.: WO2020/223433
PCT Pub. Date: Nov. 5, 2020

(65) Prior Publication Data
US 2022/0142462 A1    May 12, 2022

Related U.S. Application Data

(60) Provisional application No. 63/017,258, filed on Apr. 29, 2020, provisional application No. 62/906,353, (Continued)

(51) Int. Cl.
*A61B 1/00* (2006.01)
*A61B 1/015* (2006.01)
(Continued)

(52) U.S. Cl.
CPC .......... *A61B 1/00172* (2013.01); *A61B 1/015* (2013.01); *A61B 1/12* (2013.01); *A61B 1/3137* (2013.01)

(58) Field of Classification Search
CPC ... A61B 1/015; A61B 1/00172; A61B 5/0066; A61B 2090/3735; A61B 5/02154
See application file for complete search history.

(56) References Cited

U.S. PATENT DOCUMENTS

| 4,460,989 A | 7/1984 | Russell |
| 4,554,929 A | 11/1985 | Samson et al. |

(Continued)

FOREIGN PATENT DOCUMENTS

| AU | 2014200116 | 1/2014 |
| CN | 1684624 | 10/2005 |

(Continued)

OTHER PUBLICATIONS

Japanese Office Action dated Sep. 26, 2023 issued in Japanese Application No. 2022164724, with English summary.

(Continued)

*Primary Examiner* — Gerald Johnson
(74) *Attorney, Agent, or Firm* — Onello & Melllo, PC

(57) ABSTRACT

An imaging system for a patient comprises an imaging probe. The imaging probe comprises: an elongate shaft for insertion into the patient and comprising a proximal end, a distal portion, and a lumen extending between the proximal end and the distal portion; a rotatable optical core comprising a proximal end and a distal end, and at least a portion of the rotatable optical core is positioned within the lumen of the elongate shaft; an optical assembly positioned proximate the distal end of the rotatable optical core, the optical assembly configured to direct light to tissue and collect reflected light from the tissue; a damping fluid positioned (Continued)

between the elongate shaft and the rotatable optical core and configured to reduce non-uniform rotation of the optical assembly; and a fluid pressurization element configured to increase the pressure of the damping fluid to reduce the presence of bubbles proximate the optical assembly.

24 Claims, 10 Drawing Sheets

Related U.S. Application Data filed on Sep. 26, 2019, provisional application No. 62/850,945, filed on May 21, 2019, provisional application No. 62/840,450, filed on Apr. 30, 2019.

(51) Int. Cl.
*A61B 1/12* (2006.01)
*A61B 1/313* (2006.01)

(56) References Cited

U.S. PATENT DOCUMENTS

| | | |
|---|---|---|
| 4,566,330 A | 1/1986 | Fujii et al. |
| 4,583,184 A | 4/1986 | Murase |
| 4,588,982 A | 5/1986 | Goodwin |
| 4,594,895 A | 6/1986 | Fujii |
| 4,597,292 A | 7/1986 | Fujii et al. |
| 4,646,748 A | 3/1987 | Fujii et al. |
| 4,753,248 A | 6/1988 | Engler et al. |
| 4,951,677 A | 8/1990 | Crowley et al. |
| 4,957,482 A | 9/1990 | Shiber |
| 4,961,427 A | 10/1990 | Namekawa et al. |
| 4,983,169 A | 1/1991 | Furukawa |
| 5,002,059 A | 3/1991 | Crowley et al. |
| 5,039,193 A | 8/1991 | Snow et al. |
| 5,058,587 A | 10/1991 | Kohno et al. |
| 5,118,405 A | 6/1992 | Kaneko et al. |
| 5,127,405 A | 7/1992 | Alcala et al. |
| 5,143,075 A | 9/1992 | Ishizuka |
| 5,151,603 A | 9/1992 | Nakamura |
| 5,152,277 A | 10/1992 | Honda et al. |
| 5,158,086 A | 10/1992 | Brown et al. |
| 5,212,671 A | 5/1993 | Fujii et al. |
| 5,219,335 A | 6/1993 | Willard et al. |
| 5,321,501 A | 6/1994 | Swanson et al. |
| 5,331,309 A | 7/1994 | Sakai |
| 5,383,467 A | 1/1995 | Auer et al. |
| 5,443,781 A | 8/1995 | Saab |
| 5,456,245 A | 10/1995 | Bornhop et al. |
| 5,459,570 A | 10/1995 | Swanson et al. |
| 5,502,567 A | 3/1996 | Pokrowsky et al. |
| 5,554,139 A | 9/1996 | Okajima |
| 5,568,314 A | 10/1996 | Omori et al. |
| 5,568,503 A | 10/1996 | Omori |
| 5,588,081 A | 12/1996 | Takahashi |
| 5,644,427 A | 7/1997 | Omori et al. |
| 5,647,359 A | 7/1997 | Kohno et al. |
| 5,649,897 A | 7/1997 | Nakamura et al. |
| 5,689,316 A | 11/1997 | Hattori et al. |
| 5,738,100 A | 4/1998 | Yagami et al. |
| 5,745,163 A | 4/1998 | Nakamura et al. |
| 5,774,175 A | 6/1998 | Hattori |
| 5,774,261 A | 6/1998 | Omori et al. |
| 5,793,341 A | 8/1998 | Omori et al. |
| 5,818,399 A | 10/1998 | Omori et al. |
| 5,827,242 A | 10/1998 | Follmer et al. |
| 5,860,923 A | 1/1999 | Lenker et al. |
| 5,976,017 A | 11/1999 | Omori et al. |
| 5,999,591 A | 12/1999 | Kobayashi et al. |
| 6,011,580 A | 1/2000 | Hattori et al. |
| 6,011,809 A | 1/2000 | Tosaka |
| 6,019,507 A | 2/2000 | Takaki |
| 6,019,737 A | 2/2000 | Murata |
| 6,033,383 A | 3/2000 | Ginsburg |
| 6,036,682 A | 3/2000 | Lange et al. |
| 6,052,613 A | 4/2000 | Takaki |
| 6,064,684 A | 5/2000 | Yoon et al. |
| 6,069,698 A | 5/2000 | Ozawa et al. |
| 6,115,058 A | 9/2000 | Omori et al. |
| 6,134,003 A | 10/2000 | Tearney et al. |
| 6,160,826 A | 12/2000 | Swanson et al. |
| 6,165,127 A | 12/2000 | Crowley |
| 6,191,862 B1 | 2/2001 | Swanson et al. |
| 6,208,887 B1 | 3/2001 | Clarke |
| 6,217,828 B1 | 4/2001 | Bretscher et al. |
| 6,283,632 B1 | 9/2001 | Takaki |
| 6,296,608 B1 | 10/2001 | Daniels et al. |
| 6,309,358 B1 | 10/2001 | Okubo |
| 6,341,036 B1 | 1/2002 | Tearney et al. |
| 6,364,841 B1 | 4/2002 | White et al. |
| 6,383,209 B1 | 5/2002 | Crowley |
| 6,445,939 B1 | 9/2002 | Swanson et al. |
| 6,449,500 B1 | 9/2002 | Asai et al. |
| 6,471,656 B1 | 10/2002 | Shalman et al. |
| 6,485,413 B1 | 11/2002 | Boppart et al. |
| 6,485,482 B1 | 11/2002 | Belef |
| 6,520,959 B1 | 2/2003 | Iwahashi et al. |
| 6,530,921 B1 | 3/2003 | Maki |
| 6,547,757 B1 | 4/2003 | Kranz et al. |
| 6,549,687 B1 | 4/2003 | Kochergin et al. |
| 6,552,796 B2 | 4/2003 | Magnin et al. |
| 6,564,087 B1 | 5/2003 | Pitris et al. |
| 6,565,514 B2 | 5/2003 | Svanerudh et al. |
| 6,570,659 B2 | 5/2003 | Schmitt |
| 6,570,893 B1 | 5/2003 | Libatique et al. |
| 6,572,553 B2 | 6/2003 | Crowley |
| 6,577,391 B1 | 6/2003 | Faupel et al. |
| 6,579,286 B1 | 6/2003 | Maki et al. |
| 6,589,233 B1 | 7/2003 | Maki |
| 6,601,459 B1 | 8/2003 | Jenni |
| 6,607,526 B1 | 8/2003 | Maki |
| 6,615,072 B1 | 9/2003 | Izatt et al. |
| 6,654,630 B2 | 11/2003 | Zuluaga et al. |
| 6,658,278 B2 | 12/2003 | Gruhl |
| 6,758,818 B2 | 7/2004 | Pantages et al. |
| 6,879,851 B2 | 4/2005 | McNamara et al. |
| 6,881,194 B2 | 4/2005 | Miyata et al. |
| 6,891,984 B2 | 5/2005 | Petersen et al. |
| 6,904,197 B2 | 6/2005 | Bhagavatula et al. |
| 6,904,199 B2 | 6/2005 | Zuluaga |
| 6,916,286 B2 | 7/2005 | Kazakevich |
| 6,925,320 B2 | 8/2005 | Gruhl |
| 6,940,885 B1 | 9/2005 | Cheng et al. |
| 7,003,184 B2 | 2/2006 | Ronnekleiv et al. |
| 7,016,024 B2 | 3/2006 | Bridge et al. |
| 7,022,118 B2 | 4/2006 | Ariura et al. |
| 7,024,025 B2 | 4/2006 | Sathyanarayana |
| 7,029,436 B2 | 4/2006 | Izuka et al. |
| 7,099,358 B1 | 8/2006 | Chong |
| 7,134,994 B2 | 11/2006 | Alpert et al. |
| 7,139,120 B2 | 11/2006 | Sugiya |
| 7,155,272 B2 | 12/2006 | Yamaguchi et al. |
| 7,167,300 B2 | 1/2007 | Fermann et al. |
| 7,180,600 B2 | 2/2007 | Horii et al. |
| 7,231,243 B2 | 6/2007 | Tearney et al. |
| 7,241,286 B2 | 7/2007 | Atlas |
| 7,365,859 B2 | 4/2008 | Yun et al. |
| 7,366,376 B2 | 4/2008 | Shishkov et al. |
| 7,382,949 B2 | 6/2008 | Bouma et al. |
| 7,450,980 B2 | 11/2008 | Kawanishi |
| 7,551,293 B2 | 6/2009 | Yelin et al. |
| 7,567,349 B2 | 7/2009 | Tearney et al. |
| 7,625,366 B2 | 12/2009 | Atlas |
| 7,682,089 B2 | 3/2010 | Rohlen |
| 7,691,061 B2 | 4/2010 | Hirota |
| 7,711,413 B2 | 5/2010 | Feldman et al. |
| 7,724,786 B2 | 5/2010 | Bouma et al. |
| 7,733,497 B2 | 6/2010 | Yun et al. |
| 7,738,941 B2 | 6/2010 | Hirota |
| 7,740,408 B2 | 6/2010 | Irisawa |
| 7,742,173 B2 | 6/2010 | Yun et al. |
| 7,761,139 B2 | 7/2010 | Tearney et al. |
| 7,783,337 B2 | 8/2010 | Feldman et al. |

(56) References Cited

U.S. PATENT DOCUMENTS

| | | |
|---|---|---|
| 7,794,230 B2 | 9/2010 | Lakin et al. |
| 7,803,141 B2 | 9/2010 | Epstein et al. |
| 7,812,961 B2 | 10/2010 | Yamaguchi |
| 7,813,609 B2 | 10/2010 | Petersen et al. |
| 7,815,632 B2 | 10/2010 | Hayakawa et al. |
| 7,843,572 B2 | 11/2010 | Tearney et al. |
| 7,847,949 B2 | 12/2010 | Tearney et al. |
| 7,848,791 B2 | 12/2010 | Schmitt et al. |
| 7,867,778 B2 | 1/2011 | Hayenga et al. |
| 7,872,759 B2 | 1/2011 | Tearney et al. |
| 7,905,838 B2 | 3/2011 | Hirota |
| 7,911,621 B2 | 3/2011 | Motaghiannezam et al. |
| 7,916,387 B2 | 3/2011 | Schmitt |
| 7,920,271 B2 | 4/2011 | Vakoc et al. |
| 7,922,650 B2 | 4/2011 | McWeeney et al. |
| 7,926,562 B2 | 4/2011 | Poitzsch et al. |
| 7,935,060 B2 | 5/2011 | Schmitt et al. |
| 7,940,397 B2 | 5/2011 | Masuda |
| 7,952,718 B2 | 5/2011 | Li et al. |
| 7,969,578 B2 | 6/2011 | Yun et al. |
| 7,982,879 B2 | 7/2011 | Desjardins et al. |
| 8,018,598 B2 | 9/2011 | Cense et al. |
| 8,029,446 B2 | 10/2011 | Horiike et al. |
| 8,029,447 B2 | 10/2011 | Kanz et al. |
| 8,032,200 B2 | 10/2011 | Tearney et al. |
| 8,040,524 B2 | 10/2011 | Ozawa |
| 8,047,996 B2 | 11/2011 | Goodnow et al. |
| 8,049,900 B2 | 11/2011 | Kemp et al. |
| 8,052,605 B2 | 11/2011 | Muller et al. |
| 8,055,107 B2 | 11/2011 | Masuda |
| 8,081,316 B2 | 12/2011 | De Boer et al. |
| 8,094,319 B2 | 1/2012 | Onimura |
| 8,100,833 B2 | 1/2012 | Hirota |
| 8,108,032 B2 | 1/2012 | Onimura et al. |
| 8,116,605 B2 | 2/2012 | Petersen et al. |
| 8,125,648 B2 | 2/2012 | Milner et al. |
| 8,149,418 B2 | 4/2012 | Tearney et al. |
| 8,157,741 B2 | 4/2012 | Hirota |
| 8,157,742 B2 | 4/2012 | Taylor |
| 8,174,702 B2 | 5/2012 | Tearney et al. |
| 8,206,372 B2 | 6/2012 | Larson et al. |
| 8,206,377 B2 | 6/2012 | Petroff |
| 8,208,995 B2 | 6/2012 | Tearney et al. |
| 8,231,516 B2 | 7/2012 | Maschke |
| 8,241,196 B2 | 8/2012 | Scibona |
| 8,289,522 B2 | 10/2012 | Tearney et al. |
| RE43,875 E | 12/2012 | Shishkov et al. |
| 8,322,932 B2 | 12/2012 | Irisawa |
| 8,325,419 B2 | 12/2012 | Schmitt |
| 8,337,379 B2 | 12/2012 | Fletcher et al. |
| 8,339,592 B2 | 12/2012 | Hlavinka et al. |
| 8,346,348 B2 | 1/2013 | Onimura |
| 8,351,665 B2 | 1/2013 | Tearney et al. |
| 8,355,138 B2 | 1/2013 | Yun et al. |
| 8,384,907 B2 | 2/2013 | Tearney et al. |
| 8,384,909 B2 | 2/2013 | Yun et al. |
| 8,412,312 B2 | 4/2013 | Judell et al. |
| 8,414,496 B2 | 4/2013 | Goodnow et al. |
| 8,449,439 B2 | 5/2013 | Fletcher et al. |
| 8,449,468 B2 | 5/2013 | Petersen et al. |
| 8,452,371 B2 | 5/2013 | Feldman et al. |
| 8,473,037 B2 | 6/2013 | Irisawa |
| 8,473,073 B2 | 6/2013 | Vardiman |
| 8,478,384 B2 | 7/2013 | Schmitt et al. |
| 8,478,387 B2 | 7/2013 | Xu |
| 8,493,567 B2 | 7/2013 | Inoue |
| 8,501,015 B2 | 8/2013 | Fletcher et al. |
| 8,503,844 B2 | 8/2013 | Petersen et al. |
| 8,531,676 B2 | 9/2013 | Condit et al. |
| 8,535,210 B2 | 9/2013 | Kolenbrander et al. |
| 8,556,820 B2 | 10/2013 | Alpert et al. |
| 8,559,012 B2 | 10/2013 | Tearney et al. |
| 8,581,643 B1 | 11/2013 | Schmitt |
| 8,582,109 B1 | 11/2013 | Schmitt |
| 8,582,619 B2 | 11/2013 | Adler |
| 8,582,934 B2 | 11/2013 | Adler et al. |
| 8,585,592 B2 | 11/2013 | Luevano et al. |
| 8,593,619 B2 | 11/2013 | Colice et al. |
| 8,593,641 B2 | 11/2013 | Kemp et al. |
| 8,618,032 B2 | 12/2013 | Kurita |
| 8,626,453 B2 | 1/2014 | Myoujou et al. |
| 8,636,659 B2 | 1/2014 | Alpert et al. |
| 8,676,013 B2 | 3/2014 | Bouma et al. |
| 8,676,299 B2 | 3/2014 | Schmitt et al. |
| 8,687,201 B2 | 4/2014 | Adler |
| 8,705,046 B2 | 4/2014 | Yun et al. |
| 8,712,506 B2 | 4/2014 | Courtney et al. |
| 8,753,281 B2 | 6/2014 | Schmitt et al. |
| 8,760,663 B2 | 6/2014 | Tearney et al. |
| 8,761,469 B2 | 6/2014 | Kemp et al. |
| 8,786,336 B1 | 7/2014 | Schmitt |
| 8,804,126 B2 | 8/2014 | Tearney et al. |
| 8,808,186 B2 | 8/2014 | Fruland et al. |
| 8,810,901 B2 | 8/2014 | Huber et al. |
| 8,825,142 B2 | 9/2014 | Suehara |
| 8,827,926 B2 | 9/2014 | Kinoshita et al. |
| 8,831,321 B1 | 9/2014 | Elbasiony |
| 8,868,159 B2 | 10/2014 | Onimura |
| 8,885,171 B2 | 11/2014 | Watanabe et al. |
| 8,896,838 B2 | 11/2014 | Tearney et al. |
| 8,902,941 B2 | 12/2014 | Schmitt |
| 8,909,324 B2 | 12/2014 | Furuichi |
| 8,911,357 B2 | 12/2014 | Omori |
| 8,926,590 B2 | 1/2015 | Petroff |
| 8,928,889 B2 | 1/2015 | Tearney et al. |
| 8,945,526 B2 | 2/2015 | Akitsu et al. |
| 8,948,228 B2 | 2/2015 | Adler |
| 8,948,613 B2 | 2/2015 | Schmitt et al. |
| 8,953,911 B1 | 2/2015 | Xu et al. |
| 8,983,582 B2 | 3/2015 | Webler |
| 8,989,849 B2 | 3/2015 | Milner et al. |
| 8,994,803 B2 | 3/2015 | Kaneko |
| 8,996,099 B2 | 3/2015 | Feldman et al. |
| 8,998,797 B2 | 4/2015 | Omori |
| 9,007,696 B2 | 4/2015 | Petersen et al. |
| 9,033,890 B2 | 5/2015 | Furuichi |
| 9,036,966 B2 | 5/2015 | Bhagavatula et al. |
| 9,039,626 B2 | 5/2015 | Courtney |
| 9,050,238 B2 | 6/2015 | Nour et al. |
| 9,060,689 B2 | 6/2015 | Tearney et al. |
| 9,069,396 B2 | 6/2015 | Adler et al. |
| 9,076,202 B2 | 7/2015 | Courtney et al. |
| 9,081,148 B2 | 7/2015 | Tearney et al. |
| 9,084,532 B2 | 7/2015 | Horiike |
| 9,087,368 B2 | 7/2015 | Tearney et al. |
| 9,091,524 B2 | 7/2015 | Adler et al. |
| 9,101,298 B2 | 8/2015 | Hossack et al. |
| 9,107,682 B2 | 8/2015 | Scheller et al. |
| 9,107,687 B2 | 8/2015 | Kinoshita et al. |
| 9,121,926 B2 | 9/2015 | Nair et al. |
| 9,131,850 B2 | 9/2015 | Liu et al. |
| 9,138,147 B2 | 9/2015 | Schmitt et al. |
| 9,164,240 B2 | 10/2015 | Schmitt et al. |
| 9,168,003 B2 | 10/2015 | Suzuki et al. |
| 9,173,572 B2 | 11/2015 | Colice et al. |
| 9,173,591 B2 | 11/2015 | Elbasiony et al. |
| 9,194,690 B2 | 11/2015 | Bhagavatula et al. |
| 9,207,064 B2 | 12/2015 | Inoue |
| 9,226,660 B2 | 1/2016 | De Boer et al. |
| 9,226,665 B2 | 1/2016 | Tearney et al. |
| 9,254,102 B2 | 2/2016 | Tearney et al. |
| 9,289,127 B2 | 3/2016 | Mitsuhashi et al. |
| 9,289,582 B2 | 3/2016 | Suehara |
| 9,295,450 B2 | 3/2016 | Furuichi et al. |
| 9,295,455 B2 | 3/2016 | Karino et al. |
| 9,301,687 B2 | 4/2016 | Kemp |
| 9,304,121 B2 | 4/2016 | Tearney et al. |
| 9,322,639 B2 | 4/2016 | Watanabe et al. |
| 9,326,789 B2 | 5/2016 | Fruland et al. |
| 9,330,092 B2 | 5/2016 | Vakoc et al. |
| 9,339,173 B2 | 5/2016 | McWeeney et al. |
| 9,339,348 B2 | 5/2016 | Davies et al. |
| 9,345,864 B2 | 5/2016 | Suehara |
| 9,347,765 B2 | 5/2016 | Kemp et al. |

(56) References Cited

U.S. PATENT DOCUMENTS

| | | |
|---|---|---|
| 9,351,698 B2 | 5/2016 | Dascal et al. |
| 9,357,923 B2 | 6/2016 | Courtney et al. |
| 9,375,148 B2 | 6/2016 | Senoo |
| 9,375,158 B2 | 6/2016 | Vakoc et al. |
| 9,375,164 B2 | 6/2016 | Tolkowsky et al. |
| 9,377,290 B2 | 6/2016 | Yun et al. |
| 9,404,731 B2 | 8/2016 | Adler et al. |
| 9,408,539 B2 | 8/2016 | Tearney et al. |
| 9,417,052 B2 | 8/2016 | Adler |
| 9,427,173 B2 | 8/2016 | Sirohey et al. |
| 9,435,736 B2 | 9/2016 | Kolenbrander et al. |
| 9,435,956 B1 | 9/2016 | Xu et al. |
| 9,439,570 B2 | 9/2016 | Vertikov |
| 9,441,948 B2 | 9/2016 | Vakoc et al. |
| 9,462,950 B2 | 10/2016 | Xu |
| 9,464,883 B2 | 10/2016 | Swanson et al. |
| 9,488,464 B1 | 11/2016 | Schmitt |
| 9,507,074 B2 | 11/2016 | Zhu et al. |
| 9,513,276 B2 | 12/2016 | Tearney et al. |
| 9,526,424 B2 | 12/2016 | Judell et al. |
| 9,566,752 B2 | 2/2017 | Hartkorn |
| 9,572,495 B2 | 2/2017 | Schmitt et al. |
| 9,572,496 B2 | 2/2017 | Furuichi et al. |
| 9,574,870 B2 | 2/2017 | Yamazaki et al. |
| 9,591,967 B2 | 3/2017 | Nishiyama et al. |
| 9,605,942 B2 | 3/2017 | Staloff |
| 9,610,064 B2 | 4/2017 | Adler et al. |
| 9,615,771 B2 | 4/2017 | Furuichi et al. |
| 9,622,706 B2 | 4/2017 | Dick et al. |
| 9,638,862 B2 | 5/2017 | Bhagavatula et al. |
| 9,642,531 B2 | 5/2017 | Tearney et al. |
| 9,645,322 B2 | 5/2017 | Murashima et al. |
| 9,646,377 B2 | 5/2017 | Tearney et al. |
| 9,659,375 B2 | 5/2017 | Zagrodsky et al. |
| 9,702,687 B2 | 7/2017 | Schmitt |
| 9,702,762 B2 | 7/2017 | Friedman et al. |
| 9,704,240 B2 | 7/2017 | Lam et al. |
| 9,710,891 B2 | 7/2017 | Sakamoto |
| 9,730,613 B2 | 8/2017 | Stigall et al. |
| 9,763,623 B2 | 9/2017 | Tearney et al. |
| 9,778,020 B2 | 10/2017 | Tumlinson |
| 9,788,790 B2 | 10/2017 | Black et al. |
| 9,808,303 B2 | 11/2017 | Ryba et al. |
| 9,812,846 B2 | 11/2017 | Yun et al. |
| 9,833,221 B2 | 12/2017 | Hutchins et al. |
| 9,836,835 B2 | 12/2017 | Furuichi et al. |
| 9,843,159 B2 | 12/2017 | Cable et al. |
| 9,855,020 B2 | 1/2018 | Nair et al. |
| 9,858,387 B2 | 1/2018 | Lavi et al. |
| 9,864,140 B2 | 1/2018 | Adler et al. |
| 9,872,665 B2 | 1/2018 | Okubo et al. |
| 9,891,044 B2 | 2/2018 | Tu et al. |
| 9,897,538 B2 | 2/2018 | Tearney et al. |
| 9,907,527 B2 | 3/2018 | Dascal et al. |
| 9,907,536 B2 | 3/2018 | Courtney et al. |
| 9,933,244 B2 | 4/2018 | Krol et al. |
| 9,940,723 B2 | 4/2018 | Gopinath et al. |
| 9,943,233 B2 | 4/2018 | Lavi et al. |
| 9,962,127 B2 | 5/2018 | Wang et al. |
| 9,980,648 B2 | 5/2018 | Itoh et al. |
| 9,983,356 B2 | 5/2018 | Schmitt et al. |
| 9,986,916 B2 | 6/2018 | Köhler et al. |
| 9,986,938 B2 | 6/2018 | Tu et al. |
| 9,989,945 B2 | 6/2018 | Adler et al. |
| 9,996,921 B2 | 6/2018 | Ambwani et al. |
| 10,004,400 B2 | 6/2018 | Nakamoto et al. |
| 10,004,863 B2 | 6/2018 | Vazales et al. |
| 10,006,753 B2 | 6/2018 | Schmitt et al. |
| 10,028,725 B2 | 7/2018 | Petroff |
| 10,089,755 B2 | 10/2018 | Griffin et al. |
| 10,092,188 B2 | 10/2018 | Jaffer et al. |
| 10,109,058 B2 | 10/2018 | Ambwani et al. |
| 10,124,153 B2 | 11/2018 | Feig et al. |
| 10,140,712 B2 | 11/2018 | Ambwani |
| 10,162,114 B2 | 12/2018 | Bhagavatula et al. |
| 10,172,582 B2 | 1/2019 | Dascal et al. |
| 10,186,056 B2 | 1/2019 | Senzig et al. |
| 10,207,124 B2 | 2/2019 | Shimizu et al. |
| 10,213,109 B2 | 2/2019 | Itoh et al. |
| 10,213,186 B2 | 2/2019 | Inoue et al. |
| 10,219,780 B2 | 3/2019 | Castella et al. |
| 10,222,956 B2 | 3/2019 | Gopinath et al. |
| 10,231,712 B2 | 3/2019 | Ebbini et al. |
| 10,238,349 B2 | 3/2019 | Furuichi et al. |
| 10,238,816 B2 | 3/2019 | Matsubara et al. |
| 10,261,223 B2 | 4/2019 | Tearney et al. |
| 10,271,818 B2 | 4/2019 | Kobayashi |
| 10,285,568 B2 | 5/2019 | Tearney et al. |
| 10,327,726 B2 | 6/2019 | Dascal et al. |
| 10,331,099 B2 | 6/2019 | Adler et al. |
| 10,335,039 B2 | 7/2019 | Xu |
| 10,338,795 B2 | 7/2019 | Gopinath et al. |
| 10,342,502 B2 | 7/2019 | Dascal et al. |
| 10,387,013 B2 | 8/2019 | Jamello |
| 10,453,190 B2 | 10/2019 | Griffin |
| 10,453,191 B2 | 10/2019 | Shalev et al. |
| 10,453,196 B2 | 10/2019 | Ambwani |
| 10,463,254 B2 | 11/2019 | Tearney et al. |
| 10,499,813 B2 | 12/2019 | Adler |
| 10,529,093 B2 | 1/2020 | Griffin et al. |
| 10,551,251 B2 | 2/2020 | Friedman et al. |
| 10,568,831 B2 | 2/2020 | Mendenhall et al. |
| 10,593,037 B2 | 3/2020 | Gopinath |
| 10,631,718 B2 | 4/2020 | Petroff et al. |
| 10,631,754 B2 | 4/2020 | Gopinath |
| 10,646,198 B2 | 5/2020 | Peterson et al. |
| 10,648,918 B2 | 5/2020 | Schmitt |
| 10,687,777 B2 | 6/2020 | Dascal et al. |
| 10,713,786 B2 | 7/2020 | Ambwani et al. |
| 10,729,376 B2 | 8/2020 | Courtney |
| 10,792,012 B2 | 10/2020 | Hutchins et al. |
| 10,806,421 B2 | 10/2020 | Keller |
| 10,878,572 B2 | 12/2020 | Gopinath et al. |
| 10,902,599 B2 | 1/2021 | Ambwani et al. |
| 11,051,761 B2 | 7/2021 | Courtney et al. |
| 11,058,385 B2 | 7/2021 | Kunio |
| 11,064,873 B2 | 7/2021 | Petroff et al. |
| 11,278,206 B2 | 3/2022 | Petroff et al. |
| 11,298,110 B2 | 4/2022 | Mansour et al. |
| RE49,218 E | 9/2022 | Courtney et al. |
| 11,583,172 B2 | 2/2023 | Petroff et al. |
| 11,684,242 B2 | 6/2023 | Petroff et al. |
| 2002/0041724 A1 | 4/2002 | Ronnekleiv et al. |
| 2002/0045811 A1 | 4/2002 | Kittrell et al. |
| 2002/0072880 A1 | 6/2002 | Svanerudh et al. |
| 2002/0099289 A1 | 7/2002 | Crowley |
| 2002/0131049 A1 | 9/2002 | Schmitt |
| 2002/0151799 A1 | 10/2002 | Pantages et al. |
| 2002/0151823 A1 | 10/2002 | Miyata et al. |
| 2002/0163622 A1 | 11/2002 | Magnin et al. |
| 2002/0183601 A1 | 12/2002 | Tearney et al. |
| 2002/0183622 A1 | 12/2002 | Zuluaga et al. |
| 2002/0188204 A1 | 12/2002 | McNamara et al. |
| 2002/0198457 A1 | 12/2002 | Tearney et al. |
| 2003/0004417 A1 | 1/2003 | Ariura et al. |
| 2003/0013952 A1 | 1/2003 | Iizuka et al. |
| 2003/0032863 A1 | 2/2003 | Kazakevich |
| 2003/0073909 A1 | 4/2003 | Gruhl |
| 2003/0081875 A1 | 5/2003 | Kochergin et al. |
| 2003/0147551 A1 | 8/2003 | Sathyanarayana |
| 2003/0165291 A1 | 9/2003 | Bhagavatula et al. |
| 2003/0216621 A1 | 11/2003 | Alpert et al. |
| 2004/0017961 A1 | 1/2004 | Petersen et al. |
| 2004/0034290 A1 | 2/2004 | Zuluaga |
| 2004/0082861 A1 | 4/2004 | Gruhl |
| 2004/0092913 A1 | 5/2004 | Hennings et al. |
| 2004/0136053 A1 | 7/2004 | Sugiya |
| 2004/0215166 A1 | 10/2004 | Atlas |
| 2005/0004453 A1 | 1/2005 | Tearney et al. |
| 2005/0038406 A1 | 2/2005 | Epstein et al. |
| 2005/0101870 A1 | 5/2005 | Yamaguchi et al. |
| 2005/0128488 A1 | 6/2005 | Yelin et al. |
| 2005/0163426 A1 | 7/2005 | Fermann et al. |
| 2005/0168751 A1 | 8/2005 | Horii et al. |

(56) References Cited

U.S. PATENT DOCUMENTS

| | | |
|---|---|---|
| 2005/0187422 A1 | 8/2005 | Maschke |
| 2005/0201662 A1 | 9/2005 | Petersen et al. |
| 2005/0221277 A1 | 10/2005 | Kawanishi |
| 2005/0259242 A1 | 11/2005 | Bridge et al. |
| 2005/0272975 A1 | 12/2005 | McWeeney et al. |
| 2005/0288583 A1 | 12/2005 | Hirota |
| 2006/0039004 A1 | 2/2006 | De Boer et al. |
| 2006/0055936 A1 | 3/2006 | Yun et al. |
| 2006/0058622 A1 | 3/2006 | Tearney et al. |
| 2006/0067620 A1 | 3/2006 | Shishkov et al. |
| 2006/0091566 A1 | 5/2006 | Yang et al. |
| 2006/0093276 A1 | 5/2006 | Bouma et al. |
| 2006/0095065 A1 | 5/2006 | Tanimura et al. |
| 2006/0135870 A1 | 6/2006 | Webler |
| 2006/0166176 A1 | 7/2006 | Lakin et al. |
| 2006/0227333 A1 | 10/2006 | Tearney et al. |
| 2006/0241484 A1 | 10/2006 | Horiike et al. |
| 2006/0241493 A1 | 10/2006 | Feldman et al. |
| 2006/0241503 A1 | 10/2006 | Schmitt et al. |
| 2006/0244973 A1 | 11/2006 | Yun et al. |
| 2006/0247743 A1 | 11/2006 | Hayakawa et al. |
| 2006/0279742 A1 | 12/2006 | Tearney et al. |
| 2007/0012886 A1 | 1/2007 | Tearney et al. |
| 2007/0015969 A1 | 1/2007 | Feldman et al. |
| 2007/0035743 A1 | 2/2007 | Vakoc et al. |
| 2007/0038040 A1 | 2/2007 | Cense et al. |
| 2007/0038274 A1 | 2/2007 | Ishii et al. |
| 2007/0060822 A1 | 3/2007 | Alpert et al. |
| 2007/0073162 A1 | 3/2007 | Tearney et al. |
| 2007/0081236 A1 | 4/2007 | Tearney et al. |
| 2007/0106155 A1 | 5/2007 | Goodnow et al. |
| 2007/0121196 A1 | 5/2007 | Tearney et al. |
| 2007/0201033 A1 | 8/2007 | Desjardins et al. |
| 2007/0229801 A1 | 10/2007 | Tearney et al. |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0233396 A1 | 10/2007 | Tearney et al. |
| 2007/0236700 A1 | 10/2007 | Yun et al. |
| 2007/0244391 A1 | 10/2007 | Hirota |
| 2007/0260198 A1 | 11/2007 | Atlas |
| 2007/0268456 A1 | 11/2007 | Ohbayshi et al. |
| 2008/0002211 A1 | 1/2008 | Park et al. |
| 2008/0004530 A1 | 1/2008 | Feldman et al. |
| 2008/0007734 A1 | 1/2008 | Park et al. |
| 2008/0019908 A1 | 1/2008 | Akitsu et al. |
| 2008/0021275 A1 | 1/2008 | Tearney et al. |
| 2008/0045394 A1 | 2/2008 | Fletcher et al. |
| 2008/0049232 A1 | 2/2008 | Vakoc et al. |
| 2008/0161696 A1 | 7/2008 | Schmitt et al. |
| 2008/0165366 A1 | 7/2008 | Schmitt |
| 2008/0177139 A1 | 7/2008 | Courtney et al. |
| 2008/0181263 A1 | 7/2008 | Bouma et al. |
| 2008/0205739 A1 | 8/2008 | Hayenga et al. |
| 2008/0208227 A1 | 8/2008 | Kadykowski et al. |
| 2008/0225301 A1 | 9/2008 | Yamaguchi |
| 2008/0262346 A1 | 10/2008 | Assis et al. |
| 2008/0269572 A1 | 10/2008 | Kanz et al. |
| 2008/0291463 A1 | 11/2008 | Milner et al. |
| 2008/0297806 A1 | 12/2008 | Motaghiannezam et al. |
| 2009/0018393 A1 | 1/2009 | Dick et al. |
| 2009/0027689 A1 | 1/2009 | Yun et al. |
| 2009/0036782 A1 | 2/2009 | Vakoc et al. |
| 2009/0043191 A1 | 2/2009 | Castella et al. |
| 2009/0046295 A1 | 2/2009 | Kemp et al. |
| 2009/0046980 A1 | 2/2009 | Rohlen |
| 2009/0073454 A1 | 3/2009 | Ozawa |
| 2009/0073455 A1 | 3/2009 | Onimura |
| 2009/0093980 A1 | 4/2009 | Kemp et al. |
| 2009/0122320 A1 | 5/2009 | Petersen et al. |
| 2009/0131801 A1 | 5/2009 | Suter et al. |
| 2009/0135429 A1 | 5/2009 | Masuda |
| 2009/0143686 A1 | 6/2009 | Onimura et al. |
| 2009/0182246 A1 | 7/2009 | Kinoshita et al. |
| 2009/0192519 A1 | 7/2009 | Omori |
| 2009/0196477 A1 | 8/2009 | Cense et al. |
| 2009/0196554 A1 | 8/2009 | Irisawa |
| 2009/0251704 A1 | 10/2009 | Masuda |
| 2009/0261240 A1 | 10/2009 | Watanabe et al. |
| 2009/0262361 A1 | 10/2009 | Tanioka et al. |
| 2009/0281423 A1 | 11/2009 | Sirohey et al. |
| 2009/0283258 A1 | 11/2009 | Poitzsch et al. |
| 2009/0299195 A1 | 12/2009 | Muller et al. |
| 2009/0306520 A1 | 12/2009 | Schmitt et al. |
| 2009/0323076 A1 | 12/2009 | Li et al. |
| 2010/0019189 A1 | 1/2010 | Kurita |
| 2010/0042084 A1 | 2/2010 | Nariyuki et al. |
| 2010/0073682 A1 | 3/2010 | Inoue |
| 2010/0076320 A1 | 3/2010 | Petersen et al. |
| 2010/0094127 A1 | 4/2010 | Xu |
| 2010/0110414 A1 | 5/2010 | Colice et al. |
| 2010/0130872 A1 | 5/2010 | Irisawa |
| 2010/0157309 A1 | 6/2010 | Tearney et al. |
| 2010/0158339 A1 | 6/2010 | Omori |
| 2010/0160134 A1 | 6/2010 | Scibona |
| 2010/0160780 A1 | 6/2010 | Swan et al. |
| 2010/0168587 A1 | 7/2010 | Feldman et al. |
| 2010/0220334 A1 | 9/2010 | Condit et al. |
| 2010/0241154 A1 | 9/2010 | Larson et al. |
| 2010/0249588 A1 | 9/2010 | Knight |
| 2010/0249601 A1 | 9/2010 | Courtney |
| 2010/0253949 A1 | 10/2010 | Adler et al. |
| 2010/0298908 A1 | 11/2010 | Vardiman |
| 2010/0305452 A1 | 12/2010 | Black et al. |
| 2010/0309477 A1 | 12/2010 | Yun et al. |
| 2011/0007315 A1 | 1/2011 | Petersen et al. |
| 2011/0009741 A1 | 1/2011 | Matthews et al. |
| 2011/0019182 A1 | 1/2011 | Hlavinka et al. |
| 2011/0058178 A1 | 3/2011 | Tearney et al. |
| 2011/0071404 A1 | 3/2011 | Schmitt et al. |
| 2011/0071405 A1 | 3/2011 | Judell et al. |
| 2011/0092823 A1 | 4/2011 | Tearney et al. |
| 2011/0101207 A1 | 5/2011 | Schmitt |
| 2011/0143905 A1 | 6/2011 | Kolenbrander et al. |
| 2011/0144504 A1 | 6/2011 | Tearney et al. |
| 2011/0149296 A1 | 6/2011 | Tearney et al. |
| 2011/0151980 A1 | 6/2011 | Petroff |
| 2011/0152771 A1 | 6/2011 | Milner et al. |
| 2011/0157686 A1 | 6/2011 | Huber et al. |
| 2011/0172511 A1 | 7/2011 | Petersen et al. |
| 2011/0178398 A1 | 7/2011 | Tearney et al. |
| 2011/0178413 A1 | 7/2011 | Schmitt et al. |
| 2011/0190586 A1 | 8/2011 | Kemp |
| 2011/0196217 A1 | 8/2011 | Myoujou et al. |
| 2011/0201924 A1 | 8/2011 | Tearney et al. |
| 2011/0216325 A1 | 9/2011 | Schmitt |
| 2011/0218403 A1 | 9/2011 | Tearney et al. |
| 2011/0224541 A1 | 9/2011 | Yun et al. |
| 2011/0228280 A1 | 9/2011 | Schmitt et al. |
| 2011/0237958 A1 | 9/2011 | Onimura |
| 2011/0245683 A1 | 10/2011 | Onimura |
| 2011/0245684 A1 | 10/2011 | Onimura |
| 2011/0257463 A1 | 10/2011 | Nour et al. |
| 2011/0261366 A1 | 10/2011 | Tearney et al. |
| 2011/0267340 A1 | 11/2011 | Kraus et al. |
| 2011/0270091 A1 | 11/2011 | Hossack et al. |
| 2011/0292400 A1 | 12/2011 | Fleming et al. |
| 2011/0299091 A1 | 12/2011 | Yun et al. |
| 2012/0002928 A1 | 1/2012 | Irisawa |
| 2012/0004506 A1 | 1/2012 | Tearney et al. |
| 2012/0007974 A1 | 1/2012 | Kaneko |
| 2012/0008146 A1 | 1/2012 | Tearney et al. |
| 2012/0013914 A1 | 1/2012 | Kemp et al. |
| 2012/0022360 A1 | 1/2012 | Kemp |
| 2012/0035454 A1 | 2/2012 | Tearney et al. |
| 2012/0053918 A1 | 3/2012 | Taylor |
| 2012/0057157 A1 | 3/2012 | Petersen et al. |
| 2012/0063570 A1 | 3/2012 | Furuichi et al. |
| 2012/0065517 A1 | 3/2012 | Goodnow et al. |
| 2012/0071736 A1 | 3/2012 | Luevano et al. |
| 2012/0123352 A1 | 5/2012 | Fruland et al. |
| 2012/0127476 A1 | 5/2012 | De Boer et al. |
| 2012/0135384 A1 | 5/2012 | Nakao |

(56) References Cited

U.S. PATENT DOCUMENTS

| | | |
|---|---|---|
| 2012/0170848 A1 | 7/2012 | Kemp et al. |
| 2012/0190974 A1 | 7/2012 | Suehara |
| 2012/0215091 A1 | 8/2012 | Suzuki et al. |
| 2012/0220836 A1 | 8/2012 | Alpert et al. |
| 2012/0226151 A1 | 9/2012 | Irisawa |
| 2012/0236883 A1 | 9/2012 | Adler |
| 2012/0238869 A1 | 9/2012 | Schmitt et al. |
| 2012/0243761 A1 | 9/2012 | Senzig et al. |
| 2012/0245459 A1 | 9/2012 | Senoo |
| 2012/0250028 A1 | 10/2012 | Schmitt et al. |
| 2012/0253114 A1 | 10/2012 | Kinoshita et al. |
| 2012/0253123 A1 | 10/2012 | Shimizu et al. |
| 2012/0253184 A1 | 10/2012 | Furuichi et al. |
| 2012/0253185 A1 | 10/2012 | Furuichi |
| 2012/0281237 A1 | 11/2012 | Tearney et al. |
| 2012/0310081 A1 | 12/2012 | Adler et al. |
| 2012/0330101 A1 | 12/2012 | Brennan et al. |
| 2013/0002843 A1 | 1/2013 | Horiike |
| 2013/0006104 A1 | 1/2013 | Mitsuhashi et al. |
| 2013/0006105 A1 | 1/2013 | Furuichi |
| 2013/0010303 A1 | 1/2013 | Petersen et al. |
| 2013/0012810 A1 | 1/2013 | Nakamoto et al. |
| 2013/0012811 A1 | 1/2013 | Schmitt et al. |
| 2013/0023760 A1 | 1/2013 | Liu et al. |
| 2013/0023761 A1 | 1/2013 | Petroff |
| 2013/0046190 A1 | 2/2013 | Davies et al. |
| 2013/0051728 A1 | 2/2013 | Petroff et al. |
| 2013/0072367 A1 | 3/2013 | Fletcher et al. |
| 2013/0072805 A1 | 3/2013 | Schmitt et al. |
| 2013/0079630 A1 | 3/2013 | Horiike |
| 2013/0079631 A1 | 3/2013 | Horiike et al. |
| 2013/0100455 A1 | 4/2013 | Tearney et al. |
| 2013/0107043 A1 | 5/2013 | Fletcher et al. |
| 2013/0116671 A1 | 5/2013 | Scheller et al. |
| 2013/0128274 A1 | 5/2013 | Yun et al. |
| 2013/0144165 A1 | 6/2013 | Ebbini et al. |
| 2013/0148106 A1 | 6/2013 | Tearney et al. |
| 2013/0176571 A1 | 7/2013 | Tearney et al. |
| 2013/0185023 A1 | 7/2013 | Vakoc et al. |
| 2013/0188850 A1 | 7/2013 | Tearney et al. |
| 2013/0215427 A1 | 8/2013 | Bouma et al. |
| 2013/0216114 A1 | 8/2013 | Courtney et al. |
| 2013/0217964 A1 | 8/2013 | Kumoyama et al. |
| 2013/0222813 A1 | 8/2013 | Watanabe et al. |
| 2013/0246034 A1 | 9/2013 | Sharma et al. |
| 2013/0266259 A1 | 10/2013 | Bhagavatula et al. |
| 2013/0278936 A1 | 10/2013 | Inoue |
| 2013/0281844 A1 | 10/2013 | Karino et al. |
| 2013/0303907 A1 | 11/2013 | Corl |
| 2013/0310698 A1 | 11/2013 | Judell et al. |
| 2013/0314716 A1 | 11/2013 | Tearney et al. |
| 2013/0331689 A1 | 12/2013 | Le et al. |
| 2014/0004045 A1 | 1/2014 | Mendenhall et al. |
| 2014/0005023 A1 | 1/2014 | Kolenbrander et al. |
| 2014/0005521 A1 | 1/2014 | Köhler et al. |
| 2014/0018669 A1 | 1/2014 | Xu |
| 2014/0024930 A1 | 1/2014 | Furuichi et al. |
| 2014/0024931 A1 | 1/2014 | Winston et al. |
| 2014/0031677 A1 | 1/2014 | Iftimia et al. |
| 2014/0031679 A1 | 1/2014 | Tashiro et al. |
| 2014/0036941 A1 | 2/2014 | Desmond |
| 2014/0063488 A1 | 3/2014 | Adler |
| 2014/0066706 A1 | 3/2014 | McWeeney et al. |
| 2014/0066756 A1 | 3/2014 | Sinclair et al. |
| 2014/0083970 A1 | 3/2014 | Kumar et al. |
| 2014/0088411 A1 | 3/2014 | Suehara et al. |
| 2014/0094697 A1 | 4/2014 | Petroff et al. |
| 2014/0100451 A1 | 4/2014 | Tolkowsky et al. |
| 2014/0114182 A1 | 4/2014 | Petersen et al. |
| 2014/0142427 A1 | 5/2014 | Petroff |
| 2014/0142432 A1 | 5/2014 | Hutchins et al. |
| 2014/0142436 A1 | 5/2014 | Hutchins et al. |
| 2014/0150782 A1 | 6/2014 | Vazales et al. |
| 2014/0177935 A1 | 6/2014 | Nair et al. |
| 2014/0180071 A1 | 6/2014 | Stigall et al. |
| 2014/0180083 A1 | 6/2014 | Hoseit |
| 2014/0180121 A1 | 6/2014 | Fong |
| 2014/0187929 A1 | 7/2014 | Schmitt et al. |
| 2014/0200867 A1 | 7/2014 | Lavi et al. |
| 2014/0206989 A1 | 7/2014 | Colice et al. |
| 2014/0207168 A1 | 7/2014 | Kawaura et al. |
| 2014/0218742 A1 | 8/2014 | Adler |
| 2014/0243876 A1 | 8/2014 | Suehara |
| 2014/0247454 A1 | 9/2014 | Bhagavatula et al. |
| 2014/0249407 A1 | 9/2014 | Adler et al. |
| 2014/0257087 A1 | 9/2014 | Elbasiony et al. |
| 2014/0267038 A1 | 9/2014 | Adler et al. |
| 2014/0268167 A1 | 9/2014 | Friedman et al. |
| 2014/0270436 A1 | 9/2014 | Dascal et al. |
| 2014/0270445 A1 | 9/2014 | Kemp |
| 2014/0275995 A1 | 9/2014 | Sheehan |
| 2014/0276020 A1 | 9/2014 | Hutchins et al. |
| 2014/0276108 A1 | 9/2014 | Vertikov |
| 2014/0277072 A1 | 9/2014 | Suehara |
| 2014/0301620 A1 | 10/2014 | Tearney et al. |
| 2014/0323877 A1 | 10/2014 | Courtney et al. |
| 2014/0346693 A1 | 11/2014 | Hartkorn |
| 2014/0371598 A1 | 12/2014 | Okubo et al. |
| 2014/0376000 A1 | 12/2014 | Swanson et al. |
| 2014/0378845 A1 | 12/2014 | Nadkarni |
| 2014/0379269 A1 | 12/2014 | Schmitt |
| 2015/0005615 A1 | 1/2015 | Inoue et al. |
| 2015/0005626 A1 | 1/2015 | Kaneko |
| 2015/0005627 A1 | 1/2015 | Itoh et al. |
| 2015/0005628 A1 | 1/2015 | Itoh et al. |
| 2015/0025369 A1 | 1/2015 | Bhagavatula et al. |
| 2015/0029513 A1 | 1/2015 | Tearney et al. |
| 2015/0036146 A1 | 2/2015 | Staloff |
| 2015/0049339 A1 | 2/2015 | Tearney et al. |
| 2015/0051485 A1 | 2/2015 | Itoh et al. |
| 2015/0057958 A1 | 2/2015 | Watanabe et al. |
| 2015/0077755 A1 | 3/2015 | Yun et al. |
| 2015/0080700 A1 | 3/2015 | Fruland et al. |
| 2015/0099968 A1 | 4/2015 | Jamello |
| 2015/0099975 A1 | 4/2015 | Lam et al. |
| 2015/0119707 A1 | 4/2015 | Petroff |
| 2015/0133773 A1 | 5/2015 | Jaffer et al. |
| 2015/0133776 A1 | 5/2015 | Hoffman |
| 2015/0133789 A1 | 5/2015 | Ariura et al. |
| 2015/0153157 A1 | 6/2015 | Schmitt et al. |
| 2015/0164331 A1 | 6/2015 | Burgess et al. |
| 2015/0164423 A1 | 6/2015 | Webler |
| 2015/0182192 A1 | 7/2015 | Kaneko |
| 2015/0190054 A1 | 7/2015 | Kaneko |
| 2015/0192405 A1 | 7/2015 | Schmitt |
| 2015/0196285 A1 | 7/2015 | Mori |
| 2015/0209526 A1 | 7/2015 | Matsubara et al. |
| 2015/0216415 A1 | 8/2015 | Uribe-Patarroyo et al. |
| 2015/0219854 A1 | 8/2015 | Bhagavatula et al. |
| 2015/0230775 A1 | 8/2015 | Kobayashi |
| 2015/0238084 A1 | 8/2015 | Tearney et al. |
| 2015/0238121 A1 | 8/2015 | Tu et al. |
| 2015/0245768 A1 | 9/2015 | Hasegawa et al. |
| 2015/0257704 A1 | 9/2015 | Courtney |
| 2015/0257850 A1 | 9/2015 | Sakamoto |
| 2015/0265152 A1 | 9/2015 | Feldman et al. |
| 2015/0265162 A1 | 9/2015 | Lavi et al. |
| 2015/0268039 A1 | 9/2015 | Tu et al. |
| 2015/0282737 A1 | 10/2015 | Tolkowsky et al. |
| 2015/0297373 A1 | 10/2015 | Schmitt et al. |
| 2015/0306361 A1 | 10/2015 | Feig et al. |
| 2015/0320317 A1 | 11/2015 | Furuichi et al. |
| 2015/0338646 A1 | 11/2015 | Innami |
| 2015/0366534 A1 | 12/2015 | Nair et al. |
| 2015/0366536 A1 | 12/2015 | Courtney et al. |
| 2015/0370229 A1 | 12/2015 | Adler et al. |
| 2015/0371382 A1 | 12/2015 | Furuichi et al. |
| 2016/0000406 A1 | 1/2016 | Petroff |
| 2016/0007838 A1 | 1/2016 | Ariura et al. |
| 2016/0008090 A1 | 1/2016 | Yokoi et al. |
| 2016/0015337 A1 | 1/2016 | Inoue et al. |
| 2016/0018211 A1 | 1/2016 | Adler et al. |
| 2016/0022208 A1 | 1/2016 | Gopinath |
| 2016/0022248 A1 | 1/2016 | Mori et al. |

(56) References Cited

U.S. PATENT DOCUMENTS

| | | |
|---|---|---|
| 2016/0070066 A1 | 3/2016 | Schmitt et al. |
| 2016/0073885 A1 | 3/2016 | Adler |
| 2016/0089203 A1 | 3/2016 | Shimizu et al. |
| 2016/0089547 A1 | 3/2016 | Shimizu et al. |
| 2016/0092749 A1 | 3/2016 | Sakamoto |
| 2016/0093049 A1 | 3/2016 | Kobayashi |
| 2016/0095577 A1 | 4/2016 | Itoh et al. |
| 2016/0113485 A1 | 4/2016 | Nishiyama et al. |
| 2016/0120408 A1 | 5/2016 | Bhagavatula et al. |
| 2016/0120492 A1 | 5/2016 | Honma et al. |
| 2016/0124134 A1 | 5/2016 | Zhu et al. |
| 2016/0153765 A1 | 6/2016 | Yamazaki et al. |
| 2016/0157803 A1 | 6/2016 | Keller |
| 2016/0166815 A1 | 6/2016 | Suehara |
| 2016/0171701 A1 | 6/2016 | Zagrodsky et al. |
| 2016/0171711 A1 | 6/2016 | Gopinath et al. |
| 2016/0174925 A1 | 6/2016 | Dascal et al. |
| 2016/0199017 A1 | 7/2016 | Shimizu et al. |
| 2016/0202417 A1 | 7/2016 | Bhagavatula et al. |
| 2016/0206208 A1 | 7/2016 | Yamamoto et al. |
| 2016/0206267 A1 | 7/2016 | Shimizu et al. |
| 2016/0206290 A1 | 7/2016 | Itoh et al. |
| 2016/0228071 A1 | 8/2016 | Wang et al. |
| 2016/0270766 A1 | 9/2016 | Kobayashi |
| 2016/0301189 A1 | 10/2016 | Cable et al. |
| 2016/0313507 A1 | 10/2016 | Adler et al. |
| 2016/0320170 A1 | 11/2016 | Yun et al. |
| 2016/0320564 A1 | 11/2016 | Murashima et al. |
| 2016/0335763 A1 | 11/2016 | Ambwani et al. |
| 2016/0335766 A1 | 11/2016 | Ambwani et al. |
| 2016/0338753 A1 | 11/2016 | Ryba et al. |
| 2016/0341538 A1 | 11/2016 | Tumlinson et al. |
| 2016/0349417 A1 | 12/2016 | Tearney et al. |
| 2016/0361018 A1 | 12/2016 | Courtney et al. |
| 2016/0370168 A1 | 12/2016 | Krol et al. |
| 2017/0014100 A1 | 1/2017 | Mori |
| 2017/0020392 A1 | 1/2017 | Xu |
| 2017/0024532 A1 | 1/2017 | Gopinath et al. |
| 2017/0024910 A1 | 1/2017 | Griffin et al. |
| 2017/0103520 A1 | 4/2017 | Gopinath et al. |
| 2017/0135663 A1 | 5/2017 | Dascal et al. |
| 2017/0140243 A1 | 5/2017 | Ambwani |
| 2017/0140531 A1 | 5/2017 | Dascal et al. |
| 2017/0140532 A1 | 5/2017 | Dascal et al. |
| 2017/0140560 A1 | 5/2017 | Kraus et al. |
| 2017/0143296 A1 | 5/2017 | Peterson et al. |
| 2017/0148161 A1 | 5/2017 | Griffin |
| 2017/0153439 A1 | 6/2017 | Horiike |
| 2017/0188831 A1 | 7/2017 | Adler et al. |
| 2017/0238809 A1 | 8/2017 | Tearney et al. |
| 2017/0261378 A1 | 9/2017 | Friedman et al. |
| 2017/0301084 A1 | 10/2017 | Gopinath |
| 2017/0309018 A1 | 10/2017 | Shalev et al. |
| 2017/0311806 A1 | 11/2017 | Comstock, II et al. |
| 2017/0325712 A1 | 11/2017 | Gopinath |
| 2017/0367581 A1 | 12/2017 | Tearney et al. |
| 2018/0003482 A1 | 1/2018 | Schmitt |
| 2018/0085095 A1 | 3/2018 | Hutchins et al. |
| 2018/0085170 A1 | 3/2018 | Gopinath |
| 2018/0125372 A1 | 5/2018 | Petroff et al. |
| 2018/0172424 A1 | 6/2018 | Comstock, II et al. |
| 2018/0177404 A1 | 6/2018 | Liu |
| 2018/0192957 A1 | 7/2018 | Schmitt et al. |
| 2018/0192983 A1 | 7/2018 | Dascal et al. |
| 2018/0225830 A1 | 8/2018 | Gopinath et al. |
| 2018/0226773 A1 | 8/2018 | Yun et al. |
| 2018/0275622 A1 | 9/2018 | Adler et al. |
| 2018/0293730 A1 | 10/2018 | Ambwani et al. |
| 2018/0306569 A1 | 10/2018 | Schmitt et al. |
| 2018/0344173 A1 | 12/2018 | Tu et al. |
| 2018/0344174 A9 | 12/2018 | Schmitt et al. |
| 2018/0353241 A1 | 12/2018 | Tu et al. |
| 2019/0029623 A1 | 1/2019 | Kunio |
| 2019/0035114 A1 | 1/2019 | Griffin et al. |
| 2019/0046161 A1 | 2/2019 | Mansour et al. |
| 2019/0096063 A1 | 3/2019 | Ambwani |
| 2019/0099237 A1 | 4/2019 | Booker et al. |
| 2019/0220980 A1 | 7/2019 | Ambwani et al. |
| 2019/0274528 A1 | 9/2019 | Petroff et al. |
| 2019/0307412 A1 | 10/2019 | Dascal et al. |
| 2019/0365480 A1 | 12/2019 | Gopinath et al. |
| 2019/0380594 A1 | 12/2019 | Schmitt et al. |
| 2020/0129067 A1 | 4/2020 | Krug et al. |
| 2020/0142575 A1 | 5/2020 | Gopinath et al. |
| 2020/0167923 A1 | 5/2020 | Gopinath |
| 2020/0288950 A1 | 9/2020 | Petroff et al. |
| 2020/0355557 A1 | 11/2020 | Friedman et al. |
| 2020/0397405 A1 | 12/2020 | Hutchins et al. |
| 2021/0004955 A1 | 1/2021 | Ambwani et al. |
| 2021/0045622 A1 | 2/2021 | Petroff et al. |
| 2021/0177282 A1 | 6/2021 | Ahmed et al. |
| 2021/0267442 A1 | 9/2021 | Petersen et al. |
| 2021/0318111 A1 | 10/2021 | Vakoc et al. |
| 2022/0061670 A1 | 3/2022 | Petroff et al. |
| 2022/0142464 A1 | 5/2022 | Petroff et al. |
| 2022/0218206 A1 | 7/2022 | Petroff et al. |
| 2022/0225880 A1 | 7/2022 | Mueller et al. |
| 2023/0000321 A1 | 1/2023 | Ughi et al. |
| 2023/0181016 A1 | 6/2023 | Ughi et al. |
| 2024/0000302 A1 | 1/2024 | Petroff et al. |
| 2024/0099564 A1 | 3/2024 | Petroff et al. |
| 2025/0000351 A1 | 1/2025 | Petroff et al. |

FOREIGN PATENT DOCUMENTS

| | | |
|---|---|---|
| CN | 1780584 | 5/2006 |
| CN | 101669028 | 3/2010 |
| CN | 101773878 | 7/2010 |
| CN | 203801215 | 9/2014 |
| CN | 203801216 | 9/2014 |
| CN | 203805643 | 9/2014 |
| CN | 203805646 | 9/2014 |
| CN | 104126111 | 10/2014 |
| CN | 105019592 | 11/2015 |
| CN | 204826364 | 12/2015 |
| CN | 105662387 | 6/2016 |
| CN | 106343957 | 1/2017 |
| CN | 106570313 | 4/2017 |
| CN | 106650029 | 5/2017 |
| CN | 106805989 | 6/2017 |
| CN | 106974622 | 7/2017 |
| CN | 107115108 | 9/2017 |
| CN | 107133959 | 9/2017 |
| CN | 107233106 | 10/2017 |
| CN | 107745346 | 3/2018 |
| CN | 107978371 | 5/2018 |
| CN | 108022650 | 5/2018 |
| CN | 108038848 | 5/2018 |
| CN | 207464715 | 6/2018 |
| DE | 69738291 | 9/2008 |
| DE | 112016005442 | 8/2018 |
| DE | 112016005603 | 10/2018 |
| EP | 0883793 | 12/1998 |
| EP | 1685366 | 8/2006 |
| EP | 2505129 | 10/2012 |
| EP | 2803973 | 11/2014 |
| GB | 2512077 | 9/2014 |
| JP | 09168539 | 6/1997 |
| JP | 2000503237 | 3/2000 |
| JP | 2000097845 | 4/2000 |
| JP | 2000097846 | 4/2000 |
| JP | 2002214127 | 7/2002 |
| JP | 2004158652 | 6/2004 |
| JP | 2005224399 | 8/2005 |
| JP | 2005230552 | 9/2005 |
| JP | 2005533610 | 11/2005 |
| JP | 2006271869 | 10/2006 |
| JP | 2007268131 | 10/2007 |
| JP | 2007271728 | 10/2007 |
| JP | 20077267866 | 10/2007 |
| JP | 2008510586 | 4/2008 |
| JP | 2008514383 | 5/2008 |
| JP | 2008523954 | 7/2008 |
| JP | 2009072291 | 4/2009 |

(56) References Cited

FOREIGN PATENT DOCUMENTS

| | | |
|---|---|---|
| JP | 2009276454 | 11/2009 |
| JP | 4494203 | 6/2010 |
| JP | 2010167029 | 8/2010 |
| JP | 2010188138 | 9/2010 |
| JP | 2010533052 | 10/2010 |
| JP | 2011078550 | 4/2011 |
| JP | 2012147860 | 8/2012 |
| JP | 2012521852 | 9/2012 |
| JP | 2012205661 | 10/2012 |
| JP | 5093787 | 12/2012 |
| JP | 2012254211 | 12/2012 |
| JP | 2013500142 | 1/2013 |
| JP | 2013506136 | 2/2013 |
| JP | 2013521070 | 6/2013 |
| JP | 5269809 | 8/2013 |
| JP | 2013541392 | 11/2013 |
| JP | 2014505496 | 3/2014 |
| JP | 5474190 | 4/2014 |
| JP | 2014145942 | 8/2014 |
| JP | 2014180575 | 9/2014 |
| JP | 2014526283 | 10/2014 |
| JP | 5622796 | 11/2014 |
| JP | 5635149 | 12/2014 |
| JP | 5643315 | 12/2014 |
| JP | 2015013217 | 1/2015 |
| JP | 5689728 | 3/2015 |
| JP | 2015062638 | 4/2015 |
| JP | 5721721 | 5/2015 |
| JP | 2015518393 | 7/2015 |
| JP | 5778579 | 9/2015 |
| JP | 2015164660 | 9/2015 |
| JP | 5814860 | 11/2015 |
| JP | 2015532717 | 11/2015 |
| JP | 5856605 | 2/2016 |
| JP | 2016038329 | 3/2016 |
| JP | 2016508750 | 3/2016 |
| JP | 2016512772 | 5/2016 |
| JP | 2016514996 | 5/2016 |
| JP | 5987025 | 9/2016 |
| JP | 5997232 | 9/2016 |
| JP | 2017524422 | 8/2017 |
| JP | 2017532173 | 11/2017 |
| JP | 2018020158 | 2/2018 |
| JP | 2018507400 | 3/2018 |
| JP | 2018516147 | 6/2018 |
| JP | 2018527961 | 9/2018 |
| JP | 2018527995 | 9/2018 |
| JP | 2018191848 | 12/2018 |
| JP | 2018192287 | 12/2018 |
| WO | 2004010856 | 2/2004 |
| WO | 2004096049 | 11/2004 |
| WO | 2005047813 | 5/2005 |
| WO | 2006022342 | 3/2006 |
| WO | 2006024015 | 3/2006 |
| WO | 2006037132 | 4/2006 |
| WO | 2006068927 | 6/2006 |
| WO | 2008134449 | 11/2008 |
| WO | 2009009799 | 1/2009 |
| WO | 2009009802 | 1/2009 |
| WO | 2009010963 | 1/2009 |
| WO | 2010095370 | 8/2010 |
| WO | 2010113374 | 10/2010 |
| WO | 2011038010 | 3/2011 |
| WO | 2011059829 | 5/2011 |
| WO | 2011064775 | 6/2011 |
| WO | 2012002302 | 1/2012 |
| WO | 2012061940 | 5/2012 |
| WO | 2012064966 | 5/2012 |
| WO | 2013033415 | 3/2013 |
| WO | 2013126390 | 8/2013 |
| WO | 2014055908 | 4/2014 |
| WO | 2014142789 | 9/2014 |
| WO | 2014142815 | 9/2014 |
| WO | 2014147039 | 9/2014 |
| WO | 2014149127 | 9/2014 |
| WO | 2014163601 | 10/2014 |
| WO | 2014175853 | 10/2014 |
| WO | 2015022760 | 2/2015 |
| WO | 2015044978 | 4/2015 |
| WO | 2015044982 | 4/2015 |
| WO | 2015044983 | 4/2015 |
| WO | 2015044984 | 4/2015 |
| WO | 2015074018 | 5/2015 |
| WO | 2015103277 | 7/2015 |
| WO | 2015136853 | 9/2015 |
| WO | 2015141136 | 9/2015 |
| WO | 2016039884 | 3/2016 |
| WO | 2016168605 | 10/2016 |
| WO | WO-2016168605 A1 * 10/2016 ............... A61B 1/07 |
| WO | 2016187218 | 11/2016 |
| WO | 2016187231 | 11/2016 |
| WO | 2016210132 | 12/2016 |
| WO | 2017011587 | 1/2017 |
| WO | 2017019626 | 2/2017 |
| WO | 2017019634 | 2/2017 |
| WO | 2015044987 | 3/2017 |
| WO | 2015045368 | 3/2017 |
| WO | 2017040484 | 3/2017 |
| WO | 2017097074 | 6/2017 |
| WO | 2017189942 | 11/2017 |
| WO | 2017200381 | 11/2017 |
| WO | 2019108598 | 6/2019 |
| WO | 2020061001 | 3/2020 |
| WO | 2020237024 | 11/2020 |
| WO | 2021222530 | 11/2021 |
| WO | 2023133355 | 7/2023 |
| WO | 2024081414 | 4/2024 |
| WO | 2025076164 | 4/2025 |

OTHER PUBLICATIONS

Japanese Office Action dated Mar. 19, 2024 issued in Japanese Application No. 2021564648, with English translation.

Japanese Office Action dated Feb. 21, 2023 issued in corresponding Japanese Application No. 2021-117103, with English summary.

Extended European Search Report dated Apr. 21, 2022 issued in corresponding European Application No. 19862071.8.

Tran et al. "In vivo endoscopic optical coherence tomography by use of a rotational microelectromechanical system probe", Optics Letters, vol. 29 No. 11 (Jun. 1, 2004), p. 1236-1238.

Japanese Office Action dated Apr. 26, 2022 issued in corresponding Japanese Application No. 2021-068226, with English translation.

Abozenadah, H., et al. Consumer Chemistry: How Organic Chemistry Impacts Our Lives. CC BY-NC-SA. Available at: https://wou.edu/chemistry/courses/online-chemistry-textbooks/ch105-consumer-chemistry/ (2017).

Athanasiou, L.S. et al. "Fully automated lumen segmentation of intracoronary optical coherence tomography images", Medical Imaging 2017, vol. 10133, pp. 1013321-1-1013321-7. Downloaded from the internet on Mar. 6, 2017: http://proceedings.spiedigitallibrary.org/.

Berger, J.D. et al. "Widely tunable external cavity diode laser based on a MEMS electrostatic rotary actuator", OSA/OFC 2001, pp. TuJ2-1-TuJ2-3.

BlazePhotonics. "NL-2.4-800 Highly nonlinear PCF" technical specification sheet.

Buus, J. et al. "Tunable Lasers in Optical Networks", Journal Of Lightwave Technology, vol. 24, No. 1 (Jan. 2006), pp. 5-11.

Chang-Hasnain, C.J. "Tunable VCSEL", IEEE Journal On Selected Topics In Quantum Electronics, vol. 6, No. 6 (Nov./Dec. 2000), pp. 978-987.

Chang-Hasnain, C.J., "Progress And Prospects Of Long-Wavelength VCSELs", IEEE Optical Communications (Feb. 2003), pp. S30-S34.

Chinn, S.R. et al. "Optical coherence tomography using a frequency-tunable optical source", Optics Letters, vol. 22, No. 5 (Mar. 1, 1997), pp. 340-342.

Chinese Notice of Allowance and Supplementary Search Report dated Jan. 13, 2021 issued in related Chinese Application No. 201680034490.4.

(56) References Cited

OTHER PUBLICATIONS

Chinese Office Action dated Aug. 28, 2019 issued in related Chinese Application No. 201680034490.4, with English translation.
Chinese Office Action dated Feb. 27, 2019 issued in related Chinese Application No. 201680034490.4, with English translation.
Chinese Office Action dated May 25, 2020 issued in related Chinese Application No. 201680034490.4, with English summary.
European Office Action dated Apr. 21, 2021 issued in corresponding European Application No. 16842796.1.
European Office Action dated Feb. 4, 2020 issued in related European Application No. 16780839.3.
Extended European Search Report dated Apr. 9, 2019 issued in related European Application No. 16842796.1.
Extended European Search Report dated Jan. 2, 2019 issued in related European Application No. 16780839.3.
Extended European Search Report dated Nov. 26, 2021 issued in corresponding European Application No. 18883166.3.
International Preliminary Report on Patentability dated Jun. 11, 2020 issued in related International Application No. PCT/US2018/062766.
International Preliminary Report on Patentability dated Mar. 15, 2018 issued in related International Application No. PCT/US2016/049415.
International Preliminary Report on Patentability dated Oct. 17, 2017 issued in related International Application No. PCT/US2016/027764.
International Search Report & Written Opinion dated Feb. 11, 2019, issued in related International Application No. PCT/US2018/062766.
International Search Report and Written Opinion dated Aug. 2, 2021 issued in corresponding International Application No. PCT/US2021/029836.
International Search Report and Written Opinion dated Jan. 31, 2020 issued in related International Application No. PCT/US2019/051447.
International Search Report and Written Opinion dated Jul. 30, 2020 issued in related International Application No. PCT/US20/33953.
International Search Report and Written Opinion dated Sep. 14, 2020 issued in corresponding International Application No. PCT/US20/30616.
International Search Report and Written Opinion dated Sep. 14, 2020 issued in related International Application No. PCT/US20/30616.
International Search Report and Written Opinion dated Jul. 14, 2016 issued in related International Application No. PCT/US2016/027764.
International Search Report and Written Opinion dated Nov. 7, 2016, issued in related International Application No. PCT/US2016/049415.
Japanese Office Action dated Mar. 16, 2021 issued in related Japanese Application No. 2018-510969, with English language summary.
Japanese Office Action dated Mar. 31, 2020 issued in related Japanese Application No. 2018-505582, with English translation.
Japanese Office Action dated Nov. 17, 2020 issued in related Japanese Application No. 2018-505582, with English translation.
Japanese Office Action dated Sep. 15, 2020 issued in related Japanese Application No. 2018-510969, with English language summary.
Fermann, M.E. et al. "Ultrawide tunable Er solition fiber laser amplified in Yb-doped fiber", Optics Letters, vol. 24, No. 20 (Oct. 15, 1999), pp. 1428-1430.
Focabex, "Core Structure of Optical Cables" Article (online). Feb. 1, 2002 (retrieved Jan. 8, 2020). Retrieved from the Internet: URL: http://www.focabex.com/library-n/CORE-STRUCTURE-OF-OPTICAL-FIBER-CABLES.pdf.
Ghannam, M.T., et al. "Rheological Properties of Poly(dimethylsiloxane)". Industrial & Engineering Chemistry Research vol. 37, No. 4 (1998) pp. 1335-1340.

Golubovic, B. et al. "Optical frequency-domain reflectometry using rapid wavelength tuning of a Cr4+:forsterite laser", Optics Letters, vol. 22, No. 22 (Nov. 15, 1997), pp. 1704-1706.
Harris Jr., U.S. "Tunable Long-Wavelength Vertical-Cavity Lasers: The Engine of Next Generation Optical Networks?", IEEE Journal On Selected Topics In Quantum Electronics, vol. 6, No. 6 (Nov./Dec. 2000), pp. 1145-1160.
Introduction to silicone fluids (https://www.clearcoproducts.com/introduction-to-silicone-fluids.html), retrieved Sep. 24, 2020.
Ki, et al. "Diffractive catheter for ultrahigh-resolution spectral-domain volumetric OCT imaging", Optics Letters, vol. 39, No. 7, Optical Society of America, Mar. 26, 2014, pp. 2016-2019.
Kakuta, T. et al. "Behavior of optical fibers under heavy irradiation", Fusion Engineering And Design, vol. 41 (1998), pp. 201-205.
Madigan, Jeremy. "Vascular access: guide catheter selection, usage, and compatibility." Interventional Neuroradiology, Springer, London (2014), pp. 27-38.
Meuwissen, M. et al. "Role of Variability in Microvascular Resistance onFractional Flow Reserve and Coronary Blood Flow Velocity Reserve in Intermediate Coronary Lesions", Circulation, 103 (2001), pp. 184-187 [online—retrieved on Mar. 7, 2018]. Retrieved from the Internet URL: http://circ.ahajournals.org/content/103/2/184.
NKT Photonics. "ESM-12 SingleOmode 12 um core fiber" technical specification sheet.
NKT Photonics. "HC-1550-02 Hollow Core Photonic Bandgap Fiber" technical specification sheet.
NKT Photonics. "HC-800-02 Hollow Core Photonic Bandgap Fiber" technical specification sheet.
Ofili, E.O. et al. "Differential characterization of blood flow, velocity, and vascular resistance between proximal and distal normal epicardial human coronary arteries: Analysis by intracoronary Doppler spectral flow velocity", American Heart Journal (Jul. 1995), pp. 37-46.
Reed, W.A. et al. "Gradient-index fiber-optic microprobes for minimally invasive in vivo low-coherence interferometry", Optics Letters, vol. 27, No. 20 (Oct. 15, 2002), pp. 1794-1796.
Tearney, G.J. et al. "High-speed phase- and group-delay scanning with a grating-based phase control delay line", Optics Letters, vol. 22, No. 23 (Dec. 1, 1997), pp. 1811-1813.
Thorlabs, "Single Wavelength Graded-Index (GRIN) Lenses" Product Catalogue (online). Apr. 9, 2016 (retrieved Jan. 8, 2020). Retrieved from the Internet: URL: https://www.thorlabs.com/NewGroupPage9.cfm?ObjectGroup_ID=1209.
Von der Weid, J.P. et al. "On the Characterization of Optical Fiber Network Components with Optical Frequency Domain Reflectometry", Journal of Lightwave Technology, vol. 15, No. 7 (Jul. 1997), pp. 1131-1141.
International Search Report and Written Opinion dated Feb. 9, 2024 issued in International Application No. PCT/US2023/035132.
Chinese Office Action dated Oct. 13, 2023 issued in Chinese Application No. 202110324448.9, with English summary.
Japanese Office Action dated Nov. 15, 2022 issued in related Japanese Application No. 2021-068226, with English translation.
International Preliminary Report on Patentability electronically transmitted to Applicant on Nov. 10, 2022, Issued in related International Application No. PCT/US2021/029836.
International Search Report and Written Opinion dated Apr. 14, 2023 issued in related International Application No. PCT/US2023/010508.
Atif et al. "Catheters for optical coherence tomography", Laser Physics Letters, vol. 8, No. 9, (Jul. 1, 2011), pp. 629-646.
Extended European Search Report dated Apr. 21, 2023 issued in related European Application No. 20810126.1.
Japanese Office Action dated Apr. 25, 2023 issued in related Japanese Application No. 2021-514598, with English summary.
Summons To Attend Oral Proceedings dated Mar. 17, 2023 issued in related European Application No. 16842796.1.
Brezinski et al. "Optical Coherence Tomography: High-Resolution Imaging in Nontransparent Tissue", IEEE Journal of Selected Topics in Quantum Electronics, vol. 5, No. 4, Jul./Aug. 1999, pp. 1185-1192.

(56) References Cited

OTHER PUBLICATIONS

Extended European Search Report dated Mar. 21, 2023 issued in related European Application No. 20798343.8.
Jung et al. "Handheld Optical Coherence Tomography Scanner for Primary Care Diagnostics", IEEE Transactions On Biomedical Engineering, Mar. 2011, vol. 58, No. 3, p. 741-744.
Youngquist, R.C. et al."Optical coherence-domain reflectometry: a new optical evaluation technique", Optics Letters, vol. 12, No. 3 (Mar. 1987), pp. 158-160.
Yun, S.H. et al. "High-speed optical frequency-domain imaging", Optics Express, vol. 11, No. 22 (Nov. 3, 2003), pp. 2953-2963.
Zheng, W. "Optic Lenses Manufactured on Fiber Ends", IEEE, 978-1-4673-7732-4/15, 2015, pp. 1-10.
International Preliminary Report on Patentability dated Dec. 2, 2021 issued in corresponding International Application No. PCT/US2020/033953.
Japanese Office Action dated Aug. 2, 2022 issued in corresponding Japanese Application No. 2021-117103, with English translation.
International Preliminary Report on Patentability dated Jul. 25, 2024 issued in corresponding International Application No. PCT/US2023/010508.
Japanese Office Action dated Sep. 10, 2024 issued in Japanese Application No. 2021564648, with English translation.
Extended European Search Report dated Jun. 8, 2022 issued in related European Application No. 21217738.0.
European Office Action dated Mar. 14, 2025 issued in European Application No. 20798343.8.
International Preliminary Report on Patentability dated Apr. 24, 2025 issued in International Application No. PCT/US2023/035132.
Chinese Office Action dated May 16, 2025 issued in Chinese Application No. 202080032004.1, with English summary.

\* cited by examiner

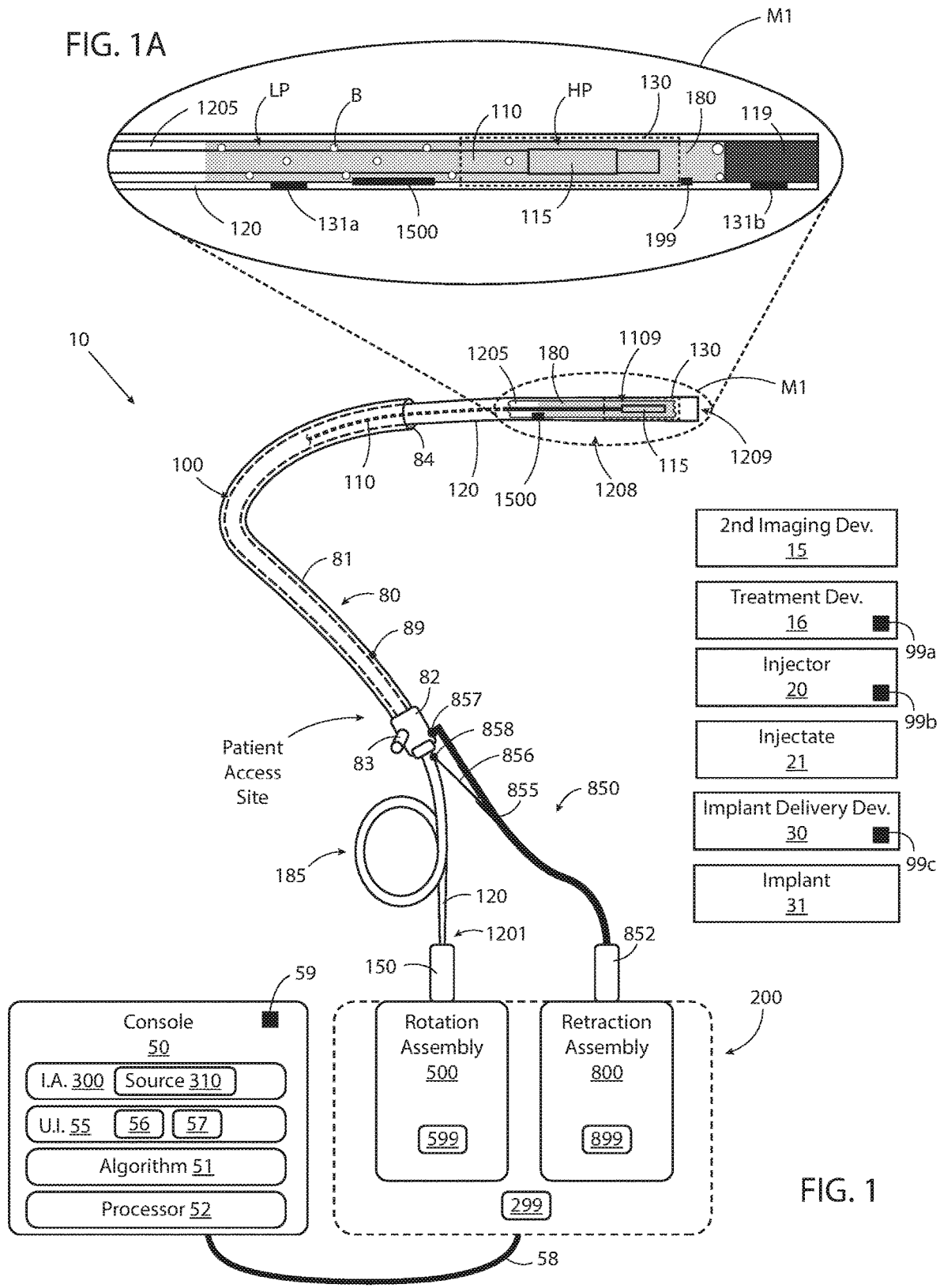

IMAGING PROBE WITH FLUID PRESSURIZATION ELEMENT

RELATED APPLICATIONS

This application claims benefit to U.S. Provisional Application Ser. No. 62/840,450, titled "Imaging Probe with Fluid Pressurization Element", filed Apr. 30, 2019, the content of which is incorporated by reference in its entirety.

This application claims benefit to U.S. Provisional Application Ser. No. 63/017,258, titled "Imaging System", filed Apr. 29, 2020, the content of which is incorporated by reference in its entirety.

This application claims benefit to U.S. Provisional Application Ser. No. 62/850,945, titled "OCT-Guided Treatment of a Patient", filed May 21, 2019, the content of which is incorporated by reference in its entirety.

This application claims benefit to U.S. Provisional Application Ser. No. 62/906,353, titled "OCT-Guided Treatment of a Patient", filed Sep. 26, 2019, the content of which is incorporated by reference in its entirety.

This application is related to U.S. Provisional Application Ser. No. 62/148,355, titled "Micro-Optic Probes for Neurology", filed Apr. 16, 2015, the content of which is incorporated by reference in its entirety.

This application is related to U.S. Provisional Application Ser. No. 62/322,182, titled "Micro-Optic Probes for Neurology", filed Apr. 13, 2016, the content of which is incorporated by reference in its entirety.

This application is related to International PCT Patent Application Serial Number PCT/US2016/027764, titled "Micro-Optic Probes for Neurology" filed Apr. 15, 2016, Publication Number WO 2016/168605, published Oct. 20, 2016, the content of which is incorporated by reference in its entirety.

This application is related to U.S. patent application Ser. No. 15/566,041, titled "Micro-Optic Probes for Neurology", filed Oct. 12, 2017, United States Publication Number 2018-0125372, published May 10, 2018, the content of which is incorporated by reference in its entirety.

This application is related to U.S. Provisional Application Ser. No. 62/212,173, titled "Imaging System Includes Imaging Probe and Delivery Devices", filed Aug. 31, 2015, the content of which is incorporated by reference in its entirety.

This application is related to U.S. Provisional Application Ser. No. 62/368,387, titled "Imaging System Includes Imaging Probe and Delivery Devices", filed Jul. 29, 2016, the content of which is incorporated by reference in its entirety.

This application is related to International PCT Patent Application Serial Number PCT/US2016/049415, titled "Imaging System Includes Imaging Probe and Delivery Devices", filed Aug. 30, 2016, Publication Number WO 2017/040484, published Mar. 9, 2017, the content of which is incorporated by reference in its entirety.

This application is related to U.S. patent application Ser. No. 15/751,570, titled "Imaging System Includes Imaging Probe and Delivery Devices", filed Feb. 9, 2018, U.S. Pat. No. 10,631,718, issued Apr. 28, 2020, the content of which is incorporated by reference in its entirety.

This application is related to U.S. Provisional Application Ser. No. 62/591,403, titled "Imaging System", filed Nov. 28, 2017, the content of which is incorporated by reference in its entirety.

This application is related to U.S. Provisional Application Ser. No. 62/671,142, titled "Imaging System", filed May 14, 2018, the content of which is incorporated by reference in its entirety.

This application is related to International PCT Patent Application Serial Number PCT/US2018/062766, titled "Imaging System", filed Nov. 28, 2018, Publication Number WO 2019/108598, published Jun. 6, 2019, the content of which is incorporated by reference in its entirety.

This application is related to U.S. Provisional Application Ser. No. 62/732,114, titled "Imaging System with Optical Pathway", filed Sep. 17, 2018, the content of which is incorporated by reference in its entirety.

This application is related to International PCT Patent Application Serial Number PCT/US2019/051447, titled "Imaging System with Optical Pathway", filed Sep. 17, 2019, Publication Number WO 2020/0611001, published Mar. 26, 2020, the content of which is incorporated by reference in its entirety.

FIELD

The present inventive concepts relate generally to imaging systems, and in particular, intravascular imaging systems including imaging probes and delivery devices.

BACKGROUND

Imaging probes have been commercialized for imaging various internal locations of a patient, such as an intravascular probe for imaging a patient's heart. Current imaging probes are limited in their ability to reach certain anatomical locations due to their size and rigidity. Current imaging probes are inserted over a guidewire, which can compromise their placement and limit use of one or more delivery catheters through which the imaging probe is inserted. There is a need for imaging systems that include probes with reduced diameter and high flexibility, as well as systems with one or more delivery devices compatible with these improved imaging probes.

SUMMARY

According to one aspect of the present inventive concepts, an imaging system for a patient comprising an imaging probe. The imaging probe comprises: an elongate shaft comprising a proximal end, a distal portion, and a lumen extending between the proximal end and the distal portion; a rotatable optical core comprising a proximal end and a distal end, and at least a portion of the rotatable optical core is positioned within the lumen of the elongate shaft; an optical assembly positioned proximate the distal end of the rotatable optical core, the optical assembly configured to direct light to tissue and collect reflected light from the tissue; a damping fluid positioned between the elongate shaft and the rotatable optical core and configured to reduce non-uniform rotation of the optical assembly; and a fluid pressurization element configured to increase the pressure of the damping fluid to reduce the presence of bubbles proximate the optical assembly; an imaging assembly constructed and arranged to optically couple to the imaging probe, the imaging assembly configured to emit light into the imaging probe and receive the reflected light collected by the optical assembly.

In some embodiments, the fluid pressurization element is configured to reduce bubble formation.

In some embodiments, the fluid pressurization element is configured to reduce the growth of one or more bubbles.

In some embodiments, the fluid pressurization element is configured to reduce the size of one or more bubbles.

In some embodiments, the system comprises an optical beam path, and the fluid pressurization element is configured to propel one or more bubbles to a location remote from the optical beam path.

In some embodiments, the fluid pressurization element is configured to create a pressure gradient within the damping fluid.

In some embodiments, the fluid pressurization element is configured to increase the pressure of the damping fluid for a limited period of time.

In some embodiments, the fluid pressurization element is configured to increase the pressure of the damping fluid intermittently. The fluid pressurization element can be configured to increase the pressure of the damping fluid only when imaging can be occurring. The fluid pressurization element can be configured to increase the pressure of the damping fluid only when the rotatable optical core is rotated. The fluid pressurization element can be configured to increase the pressure of the damping fluid for discrete time periods of no more than two minutes. The fluid pressurization element can be configured to increase the pressure of the damping fluid for discrete time periods of no more than 30 seconds. The fluid pressurization element can be configured to increase the pressure of the damping fluid for discrete time periods of no more than five seconds.

In some embodiments, the fluid pressurization element is configured to generate a pressure of the damping fluid of at least: 3.6 psi; 5.0 psi; 10 psi; 15 psi; 20 psi; 30 psi; and/or 40 psi.

In some embodiments, the fluid pressurization element is configured to generate a pressure of the damping fluid of at least: 75 psi; 100 psi; 125 psi; and/or 150 psi.

In some embodiments, the fluid pressurization element is configured to generate a high pressure area and a low pressure area within the damping fluid.

In some embodiments, the fluid pressurization element comprises a pressurization source. The pressurization source can comprise a pump. The fluid pressurization element can further comprise a valve configured to allow passage of gas while limiting passage of the damping fluid.

In some embodiments, the fluid pressurization element is configured to increase the pressure of the damping fluid when the rotatable optical core is rotated. The fluid pressurization element can comprise at least one projection that radially extends from the rotatable optical core. The at least one projection can comprise multiple projections that each radially extend from the rotatable optical core. The fluid pressurization element can comprise a helical projection that radially extends from the rotatable optical core. The fluid pressurization element can comprise a helical coil surrounding the rotatable optical core. The helical coil can have uniform pitch. The fluid pressurization element can comprise an element with a propeller-like construction. The fluid pressurization element can comprise a spring-type element.

In some embodiments, the fluid pressurization element comprises a first fluid pressurization element and a second fluid pressurization element, and the second fluid pressurization element is positioned proximal to the first fluid pressurization element. The second fluid pressurization element can be configured to prime the first fluid pressurization element when rotated.

In some embodiments, the fluid pressurization element is adhesively attached to the rotatable optical core.

In some embodiments, the fluid pressurization element is molded on and/or with the rotatable optical core.

In some embodiments, the fluid pressurization element is fused onto the rotatable optical core.

In some embodiments, the fluid pressurization element is formed into the rotatable optical core. The system can be formed onto the rotatable optical core via deposition and/or three-dimensional (3D) printing.

In some embodiments, the fluid pressurization element comprises a material selected from the group consisting of: metal; plastic; stainless steel; nickel-titanium alloy; nylon; polyether ether ketone; polyimide; and combinations thereof.

In some embodiments, the rotatable optical core comprises a diameter D1, and the elongate shaft lumen comprises a diameter D2, and the fluid pressurization element extends from the rotatable optical core with a radial height H1, and H1 comprises at least 5% and/or no more than 95% of half the difference between D1 and D2.

In some embodiments, the rotatable optical core comprises a diameter D1, and the elongate shaft lumen comprises a diameter D2, and the fluid pressurization element extends from the rotatable optical core with a radial height H1, and a clearance C1 comprises one half the difference between D1 and D2 minus H1, and clearance C1 comprises a length of no more than 100 µm and/or no more than 75 µm.

In some embodiments, the fluid pressurization element comprises a covering. The covering can comprise an element selected from the group consisting of: sheath; heat shrink tube; painted on coating; sprayed on coating; and combinations thereof.

In some embodiments, the fluid pressurization element is further configured to produce a motive force, and the motive force is configured to translate the rotatable optical core. The fluid pressurization element can be configured to advance the rotatable optical core when rotated in a first direction and to retract the rotatable optical core when rotated in a second direction which is opposite the first direction.

In some embodiments, the damping fluid comprises a non-Newtonian fluid.

In some embodiments, the damping fluid comprises a shear-thinning fluid.

In some embodiments, the damping fluid comprises a static viscosity of at least 500 centipoise. The damping fluid can comprise a shear viscosity that is less than its static viscosity. The damping fluid can comprise a static viscosity to shear viscosity ratio of at least 1.2:1 and/or no more than 100:1.

In some embodiments, the damping fluid comprises a first fluid and a second fluid. The first fluid can comprise a low viscosity fluid and the second fluid can comprise a high viscosity fluid.

In some embodiments, the damping fluid comprises a low viscosity fluid configured to reduce bubble formation. The damping fluid can comprise a fluid with a viscosity of no more than 1000 centipoise.

In some embodiments, the damping fluid comprises a fluid with high surface tension configured to reduce bubble formation. The damping fluid can comprise a fluid with a surface tension of at least 40 dynes/cm.

In some embodiments, the imaging probe comprises a distal portion with a diameter of no more than 0.020". The imaging probe distal portion can comprise a diameter of no more than 0.016".

In some embodiments, the imaging probe further includes a sealing element in a distal portion of the elongate shaft.

According to another aspect of the present inventive concepts, an imaging probe comprises: an elongate shaft comprising a proximal end, a distal portion, and a lumen extending between the proximal end and the distal portion; a rotatable optical core comprising a proximal end and a distal end, and at least a portion of the rotatable optical core is positioned within the lumen of the elongate shaft; and an optical assembly positioned proximate the distal end of the rotatable optical core, the optical assembly configured to direct light to tissue and collect reflected light from the tissue; and the shaft comprises a proximal shaft and a distal shaft attached thereto; and the proximal shaft comprises a first tubular member with a first lumen, and the distal shaft comprises a second tubular member with a second lumen, and the shaft further comprises a third tubular member that extends into the first lumen and the second lumen, and the shaft further comprises a fourth tubular member with a proximal portion that surrounds a distal portion of the first tubular member and a distal portion positioned between a proximal portion of the second tubular member and the third tubular member.

In some embodiments, the first tubular member comprises a spiral cut hypotube.

In some embodiments, the second tubular member comprises a transparent material.

In some embodiments, the third tubular member comprises an outer diameter that is greater than the first lumen.

In some embodiments, the fourth tubular member comprises a heat shrink material.

In some embodiments, the imaging probe further comprises adhesive positioned between two or more of the first tubular member, second tubular member, third tubular member, and/or fourth tubular member.

In some embodiments, the imaging probe further comprises a fluid propulsion element with a diameter D1, and the third tubular member comprises a lumen with a diameter less than D1.

In some embodiments, the second tubular member comprises a projection extending toward the third tubular member.

In some embodiments, the second tubular member comprises a maximum diameter proximate the third tubular member, and the fourth tubular member comprises a maximum diameter proximate the third tubular member, and each maximum diameter does not exceed a diameter of 0.02", 0.0175", and/or 0.0155".

In some embodiments, the fluid pressurization element comprises a first fluid pressurization element and a second fluid pressurization element. The first and second pressurization elements can create opposing pressure gradients when rotated.

According to another aspect of the invention, a method of producing a fluid propulsion element for an optical probe comprises: providing a tube with a mandrel inserted therethrough; creating two or more helical channels along the length of the tube; removing a first fluid propulsion element from the mandrel; and removing a second fluid propulsion element from the mandrel.

In some embodiments, the method further comprises producing a first optical probe using at least the first fluid propulsion element. The method can further comprise producing a second optical probe using the second fluid propulsion element.

The technology described herein, along with the attributes and attendant advantages thereof, will best be appreciated and understood in view of the following detailed description taken in conjunction with the accompanying drawings in which representative embodiments are described by way of example.

INCORPORATION BY REFERENCE

All publications, patents, and patent applications mentioned in this specification are herein incorporated by reference to the same extent as if each individual publication, patent, or patent application was specifically and individually indicated to be incorporated by reference. The content of all publications, patents, and patent applications mentioned in this specification are herein incorporated by reference in their entirety for all purposes.

BRIEF DESCRIPTION OF THE DRAWINGS

FIG. 1 illustrates a schematic view of an imaging system comprising an imaging probe with a fluid pressurization element, consistent with the present inventive concepts.

FIG. 1A illustrates a magnified view of the components within circle M1 of FIG. 1, consistent with the present inventive concepts.

DETAILED DESCRIPTION OF THE INVENTION

Figure 2A:
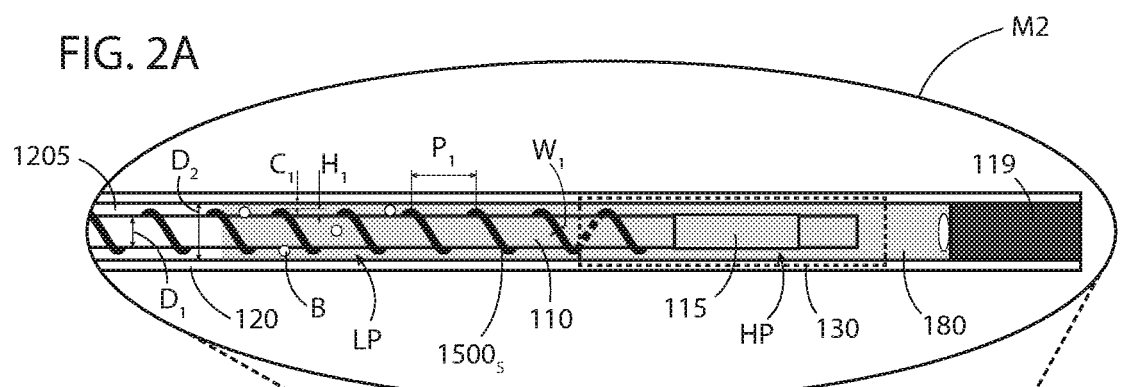
FIGS. 2 and 2A illustrate a schematic view of the distal portion of an imaging probe and delivery catheter, and a magnified view of the components within circle M2, respectively, consistent with the present inventive concepts.

Reference will now be made in detail to the present embodiments of the technology, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third, etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

As used herein, the term "proximate", when used to describe proximity of a first component or location to a second component or location, is to be taken to include one or more locations near to the second component or location, as well as locations in, on and/or within the second component or location. For example, a component positioned proximate an anatomical site (e.g. a target tissue location), shall include components positioned near to the anatomical site, as well as components positioned in, on and/or within the anatomical site.

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The terms "reduce", "reducing", "reduction" and the like, where used herein, are to include a reduction in a quantity, including a reduction to zero. Reducing the likelihood of an occurrence shall include prevention of the occurrence. Correspondingly, the terms "prevent", "preventing", and "prevention" shall include the acts of "reduce", "reducing", and "reduction", respectively.

The term "and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

The term "one or more", where used herein can mean one, two, three, four, five, six, seven, eight, nine, ten, or more, up to any number.

The terms "and combinations thereof" and "and combinations of these" can each be used herein after a list of items that are to be included singly or collectively. For example, a component, process, and/or other item selected from the group consisting of: A; B; C; and combinations thereof, shall include a set of one or more components that comprise: one, two, three or more of item A; one, two, three or more of item B; and/or one, two, three, or more of item C.

In this specification, unless explicitly stated otherwise, "and" can mean "or", and "or" can mean "and". For example, if a feature is described as having A, B, or C, the feature can have A, B, and C, or any combination of A, B, and C. Similarly, if a feature is described as having A, B, and C, the feature can have only one or two of A, B, or C.

The expression "configured (or set) to" used in the present disclosure may be used interchangeably with, for example, the expressions "suitable for", "having the capacity to", "designed to", "adapted to", "made to" and "capable of" according to a situation. The expression "configured (or set) to" does not mean only "specifically designed to" in hardware. Alternatively, in some situations, the expression "a device configured to" may mean that the device "can" operate together with another device or component.

As used herein, the term "threshold" refers to a maximum level, a minimum level, and/or range of values correlating to a desired or undesired state. In some embodiments, a system parameter is maintained above a minimum threshold, below a maximum threshold, within a threshold range of values, and/or outside a threshold range of values, such as to cause a desired effect (e.g. efficacious therapy) and/or to prevent or otherwise reduce (hereinafter "prevent") an undesired event (e.g. a device and/or clinical adverse event). In some embodiments, a system parameter is maintained above a first threshold (e.g. above a first temperature threshold to cause a desired therapeutic effect to tissue) and below a second threshold (e.g. below a second temperature threshold to prevent undesired tissue damage). In some embodiments, a threshold value is determined to include a safety margin, such as to account for patient variability, system variability, tolerances, and the like. As used herein, "exceeding a threshold" relates to a parameter going above a maximum threshold, below a minimum threshold, within a range of threshold values and/or outside of a range of threshold values.

As described herein, "room pressure" shall mean pressure of the environment surrounding the systems and devices of the present inventive concepts. Positive pressure includes pressure above room pressure or simply a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described hereabove.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

As used herein, the term "functional element" is to be taken to include one or more elements constructed and arranged to perform a function. A functional element can comprise a sensor and/or a transducer. In some embodiments, a functional element is configured to deliver energy and/or otherwise treat tissue (e.g. a functional element configured as a treatment element). Alternatively or additionally, a functional element (e.g. a functional element comprising a sensor) can be configured to record one or more parameters, such as a patient physiologic parameter; a patient anatomical parameter (e.g. a tissue geometry parameter); a patient environment parameter; and/or a system parameter. In some embodiments, a sensor or other functional element is configured to perform a diagnostic function (e.g. to gather data used to perform a diagnosis). In some embodiments, a functional element is configured to perform a therapeutic function (e.g. to deliver therapeutic energy and/or a therapeutic agent). In some embodiments, a functional element comprises one or more elements constructed and arranged to perform a function selected from the group consisting of: deliver energy; extract energy (e.g. to cool a component); deliver a drug or other agent; manipulate a system component or patient tissue; record or otherwise sense a parameter such as a patient physiologic parameter or a system parameter; and combinations of one or more of these. A functional element can comprise a fluid and/or a fluid delivery system. A functional element can comprise a reservoir, such as an expandable balloon or other fluid-maintaining reservoir. A "functional assembly" can comprise an assembly constructed and arranged to perform a function, such as a diagnostic and/or therapeutic function. A functional assembly can comprise an expandable assembly. A functional assembly can comprise one or more functional elements.

The term "transducer" where used herein is to be taken to include any component or combination of components that receives energy or any input, and produces an output. For example, a transducer can include an electrode that receives electrical energy, and distributes the electrical energy to tissue (e.g. based on the size of the electrode). In some configurations, a transducer converts an electrical signal into any output, such as light (e.g. a transducer comprising a light emitting diode or light bulb), sound (e.g. a transducer comprising a piezo crystal configured to deliver ultrasound energy), pressure, heat energy, cryogenic energy, chemical energy; mechanical energy (e.g. a transducer comprising a motor or a solenoid), magnetic energy, and/or a different electrical signal (e.g. a Bluetooth or other wireless communication element). Alternatively or additionally, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); chemical energy; electromagnetic energy; magnetic energy; and combinations of one or more of these.

As used herein, the term "fluid" can refer to a liquid, gas, gel, or any flowable material, such as a material which can be propelled through a lumen and/or opening.

It is appreciated that certain features of the inventive concepts, which are, for clarity, described in the context of separate embodiments, may also be provided in combination in a single embodiment. Conversely, various features of the inventive concepts which are, for brevity, described in the context of a single embodiment, may also be provided separately or in any suitable sub-combination. For example, it will be appreciated that all features set out in any of the claims (whether independent or dependent) can be combined in any given way.

It is to be understood that at least some of the figures and descriptions of the inventive concepts have been simplified to focus on elements that are relevant for a clear understanding of the inventive concepts, while eliminating, for purposes of clarity, other elements that those of ordinary skill in the art will appreciate may also comprise a portion of the inventive concepts. However, because such elements are well known in the art, and because they do not necessarily facilitate a better understanding of the invention, a description of such elements is not provided herein.

Terms defined in the present disclosure are only used for describing specific embodiments of the present disclosure and are not intended to limit the scope of the present disclosure. Terms provided in singular forms are intended to include plural forms as well, unless the context clearly indicates otherwise. All of the terms used herein, including technical or scientific terms, have the same meanings as those generally understood by an ordinary person skilled in the related art, unless otherwise defined herein. Terms defined in a generally used dictionary should be interpreted as having meanings that are the same as or similar to the contextual meanings of the relevant technology and should not be interpreted as having ideal or exaggerated meanings, unless expressly so defined herein. In some cases, terms defined in the present disclosure should not be interpreted to exclude the embodiments of the present disclosure.

Provided herein are imaging systems for a patient including an imaging probe and an imaging assembly that optically couples to the imaging probe. The probe comprises an elongate shaft, a rotatable optical core, and an optical assembly. The rotatable optical core is positioned within a lumen of the elongate shaft. The optical assembly is positioned proximate a distal end of the optical core and is configured to direct light to tissue and collect reflected light from tissue. The imaging assembly, when optically coupled to the imaging probe, is configured to emit light into the imaging probe and receive the reflected light collected by the optical assembly, such as to provide images of blood vessels and devices positioned within blood vessels. The probe can include a damping fluid positioned between the elongate shaft and the rotatable optical core, and this damping fluid can be configured to reduce non-uniform rotation of the optical assembly, thus reducing undesired distortions of images produced by the system. The probe can further include a fluid pressurization element configured to increase the pressure of the damping fluid to reduce presence of bubbles proximate the optical assembly (e.g. bubbles that would limit or reduce the quality of images produced by the system).

Imaging of blood vessels is the primary diagnostic tool when planning and applying therapies such as thrombolytic drugs or stent retrievers for clot removal (e.g. ischemic stroke) or coils, flow diverters and other devices for aneurysm repair (e.g. hemorrhagic stroke). External, non-invasive, imaging such as x-ray angiography or magnetic resonance imaging (MRI) are the primary imaging techniques but such techniques provide information only on the vessel size and shape, and with moderate resolution (~0.2 mm or 200 um). Such levels of resolution do not permit the imaging of important smaller features present in the vasculature. An inability to adequately image these vessels limits pre-procedural planning and acute assessment of therapeutic results. These imaging technologies are further limited in effectiveness due to the shadowing and local image obliteration created by the therapies themselves in the case of coils. Thus, there is a desire to also perform the intravascular imaging of the present inventive concepts to examine the detailed morphology of the interior vessel wall and/or to better plan and assess the results of catheter-based interventions. Currently, intravascular imaging techniques such as Intravascular Ultrasound (IVUS) and intravascular Optical Coherence Tomography (OCT) have been developed and approved for use in the coronary arteries. IVUS is also used in the larger peripheral vasculature. However, intravascular imaging has not been extended into the neurological vessels except for the larger carotid arteries. This limitation is due mainly to two reasons: the neurological vessel sizes can become very small, on the order of 1 mm in diameter or less, and the vessel tortuosity becomes quite high. Therefore, there is a need for smaller and more flexible imaging probes, such as probes that can safely and effectively navigate the tortuous carotid sinus to reach and image the mid-cranial artery, as well as its more distal branches and segments.

Due to the fundamental limits of ultrasound resolution, especially the unavoidable beam spreading when small transducers are used, optical techniques are preferred. In particular, with the advent of new light sources such as broad band superluminescent light emitting diodes (SLEDs), super-continuum lasers, compact swept-frequency light sources, micro-optical systems, and interferometric detection of the return light using techniques such as Optical Coherence Tomography (OCT), all of which are compatible with single-mode fibers, the use of optical techniques becomes highly advantageous both from a clinical performance as well as commercial viewpoint. Furthermore, the use of single mode fibers allows the smallest possible imaging probes to be considered.

In general, to create a three-dimensional (3D) view of the interior wall of a blood vessel, light delivered by distally located imaging optics of an inserted probe can be swept over the surface of the lumen by simultaneous axial translation ('pull-back') and rotation of the optics and an attached fiber. To facilitate accurate, distortion-free images, the distal rotation rate should be uniform in speed. Due to size and cost, drive motors that cause the rotation are located proximally, outside the patient and separate from the imaging probe (e.g. configured in a reusable arrangement for use with multiple imaging probes). The natural tendency of the probe's fiber is to "whip" at the distal end, creating an effect known as Non-Uniform Rotational Distortion (NURD). To overcome this undesired effect, tightly wound, spring-like coils known as torque wires, with the fiber located in the center of the coil, have been used to reduce non-uniform rotation to the distal optics. These torque wires can add bulk to the catheter (e.g. increase in diameter), have tortuosity limits beyond which NURD reappears, and can be costly. Furthermore, torque wires are sensitive to the total accumulated tortuosity integrated along the length of the catheter, and since torque wires must be attached to a proximal drive source, this total integrated tortuosity can become significant (e.g. and cause NURD to reappear). Since uniform rotation is only required for the optics at the distal tip, the rotation of components proximal to the distal optics need not be as well controlled; in other words, the fiber can twist and untwist in the proximal regions as the tortuosity varies without generating NURD, as long as the rotational speed of the distal optics remains relatively constant. Thus, a configuration in which uniform rotation is controlled for the distal optics without a torque wire can both avoid numerous limitations as well as provide numerous advantages.

To overcome the limitations of torque wires, damping fluids have been used to control rotational speed variations. For example, U.S. Pat. No. 6,891,984 (the '984 patent), describes the use of viscous fluids to cause fiber "wind-up" and rotational energy storage. The unwinding rate is also determined by the fluid's viscosity, which can provide an effective feedback mechanism for rotational control. Any fluid over the lens needs to meet desired optical properties, in particular an optical index within an acceptable range to minimize cylindrical distortion, as well as a low absorption at the operating wavelengths. The fluid selected can comprise a biocompatible fluid, since is it temporarily positioned inside the body. If not biocompatible, additional protective layers can be added to guard against undesirable single-fault conditions (e.g. leak conditions).

Systems of the present inventive concepts can include a non-Newtonian fluid and/or shear-thinning fluid such as to accommodate high-speed rotation, such as is described in applicant's co-pending U.S. patent application Ser. No. 15/566,041, titled "Micro-Optic Probes for Neurology", filed Oct. 12, 2017.

Fluid-based rotational control solutions (e.g. fluid damping solutions) all suffer from a susceptibility to bubbles forming within the fluid. Although the bubbles will have, in general, a small effect on the mechanical performance, it is easily appreciated that a bubble located in the path of delivered and/or received light (the "optical beam path") will have significant undesired effects on the image quality. Bubble formation is inherent with rotating elements in a fluid field, such as via a phenomenon known as cavitation. Fluid-solid interfaces can also create bubbles in the fluid through nucleation, but cavitation is usually dominant with high-speed rotating. Due to the requirement for directing the light beam relatively orthogonal to the probe axis, some asymmetry will exist in the distal optics (e.g. a lens assembly with a beveled distal end configured to direct light 90° from the axis of the distal end of the attached fiber) and thus a propensity for generating low pressure regions at high speed rotation will typically occur.

Cavitation is the presence of small vapor-filled zones ("bubbles"), that are the consequence when a liquid is subjected to rapid changes of pressure that cause the formation of cavities in the regions where the pressure is relatively low. There are several general properties of the system of the present inventive concepts that can be optimized to minimize cavitation and its associated bubble formation. For example, the geometry of the imaging probe (e.g. the spaces in which a damping fluid is positioned) can be constructed and arranged to minimize bubble formation. The viscosity of an included damping fluid can be chosen to limit bubble formation. A damping fluid can comprise a fluid with low vapor pressure and/or low levels of dissolved gas (or gasses). A damping fluid can comprise a fluid that has high surface tension (e.g. to tend to cause bubbles to collapse). A damping fluid can comprise a fluid with low surface tension (e.g. if bubble formation is caused via nucleation), such as a wetting agent. Low viscosity fluids will tend to reduce bubble formation, but they may not effectively control NURD by themselves. Combinations of two or more fluids (e.g. in a stacked arrangement) can be used, such as when one or more sealing elements are included to keep the fluids separated. The low-viscosity fluid can be positioned over the distal optics (e.g. only over the distal optics), and the high viscosity fluid placed proximal to the low viscosity fluid and extending over a relatively longer segment of the imaging probe. In some embodiments, one or more damping fluids are used, wherein the one or more damping fluids comprise: a viscosity chosen to reduce bubble formation; a low vapor pressure; a low level of dissolved gas; a low surface tension; and/or a high surface tension.

In some embodiments, pressure of an included damping fluid (or other fluid) can be increased, such as to cause an effect selected from the group consisting of: reduction of bubble formation; reduced growth of one or more bubbles (e.g. one or more existing bubbles); reduction in size of one or more bubbles (e.g. one or more existing bubbles); propulsion of one or more bubbles to a location remote from the optical beam path; and combinations of these. Increased pressurization of the damping fluid can be performed for a limited time, as prolonged pressurization can cause the fluid to adsorb additional gasses, causing a new vapor pressure to be established. The pressurization elements of the present inventive concepts can be of small size (e.g. compact), so as to be enclosed within the probe. These pressurization elements can be activated (e.g. to generate increased pressure of a damping fluid) only when actual imaging is occurring (e.g. when the fiber and distal optics are rotated at high speeds), such as to avoid establishing an undesired equilibrium condition caused by prolonged pressurization.

All of the above bubble-reducing configurations can be applied individually and/or in combination to prevent, limit, and/or reduce bubble formation proximate the distal optics of the probe.

The systems of the present inventive concepts can include a probe with a fluid pressurization element configured to "minimize a bubble effect" (e.g. reduce the presence of bubbles at one or more locations), which shall include: preventing, limiting, and/or reducing formation of one or more bubbles; limiting and/or reducing the expansion of one or more bubbles; reducing the size of one or more bubbles; and/or moving one or more bubbles away from the optical beam path (e.g. moving one or more bubbles away from the optical assembly transmitting light to and/or from tissue).

Referring now to FIG. 1, a schematic view of an imaging system comprising an imaging probe with a fluid pressurization element is illustrated, consistent with the present inventive concepts. Referring additionally to FIG. 1A, a magnified view of the components within circle M1 is illustrated, consistent with the present inventive concepts. Imaging system 10 is constructed and arranged to collect image data and produce one or more images based on the recorded data, such as when imaging system 10 comprises an Optical Coherence Tomography (OCT) imaging system constructed and arranged to collect image data of an imaging location (e.g. a segment of a blood vessel, such as during a pullback procedure). Imaging system 10 comprises a catheter-based probe, imaging probe 100, as well as a rotation assembly 500 and a retraction assembly 800, each of which can operably attach to imaging probe 100. Imaging system 10 can further comprise console 50 which is configured to operably connect to imaging probe 100, such as via rotation assembly 500 and/or retraction assembly 800. Imaging probe 100 can be introduced into a conduit of the patient, such as a blood vessel or other conduit of the patient, through one or more delivery catheters, for example delivery catheter 80 shown. Additionally or alternatively, imaging probe 100 can be introduced through an introducer device, such as an endoscope, arthroscope, balloon dilator, or the like. In some embodiments, imaging probe 100 is configured to be introduced into a conduit selected from the group consisting of: an artery; a vein; an artery within or proximate the heart; a vein within or proximate the heart; an artery within or proximate the brain; a vein within or proximate the brain; a peripheral artery; a peripheral vein; through a natural body orifice into a conduit, such as the esophagus; through a surgically created orifice into a body cavity, such as the abdomen; and combinations of one or more of these. Imaging system 10 can further comprise additional imaging devices, such as second imaging device 15 shown. Imaging system 10 can further comprise a device configured to treat the patient, treatment device 16. Imaging system 10 can further comprise a fluid injector, such as injector 20, which can be configured to inject one or more fluids, such as a flushing fluid, an imaging contrast agent (e.g. a radiopaque contrast agent, hereinafter "contrast") and/or other fluid, such as injectate 21 shown. Imaging system 10 can further comprise an implant, such as implant 31, which can be implanted in the patient via a delivery device, such as an implant delivery device 30 and/or delivery catheter 80.

In some embodiments, imaging probe 100 and/or another component of imaging system 10 can be of similar construction and arrangement to the similar components described in applicant's co-pending U.S. patent application Ser. No. 15/566,041, titled "Micro-Optic Probes for Neurology", filed Oct. 12, 2017, and/or applicant's co-pending U.S. Provisional Patent Application Ser. No. 62/732,114, titled "Imaging System with Optical Pathway", filed Sep. 17, 2018. Imaging probe 100 can be constructed and arranged to collect image data from a patient site, such as an intravascular cardiac site, an intracranial site, or other site accessible via the vasculature of the patient. In some embodiments, imaging system 10 can be of similar construction and arrangement to the similar systems and their methods of use described in applicant's co-pending U.S. patent application Ser. No. 15/751,570, titled "Imaging System includes Imaging Probe and Delivery Devices", filed Feb. 9, 2018.

Delivery catheter 80 comprises an elongate shaft, shaft 81, with a lumen 84 therethrough, and a connector 82 positioned on its proximal end. Connector 82 can comprise a Touhy or other valved connector, such as a valved connector configured to prevent fluid egress from the associated delivery catheter 80 (with and/or without a separate shaft positioned within the connector 82). Connector 82 can comprise a port 83, such as a port constructed and arranged to allow introduction of fluid into delivery catheter 80 and/or for removing fluids from delivery catheter 80. In some embodiments, a flushing fluid, as described herebelow, is introduced via one or more ports 83, such as to remove blood or other undesired material from locations proximate an optical assembly (e.g. from a location proximal to an optical assembly to a location distal to the optical assembly, such as optical assembly 115 described herebelow). Port 83 can be positioned on a side of connector 82 and can include a luer fitting and a cap and/or valve. Shafts 81, connectors 82, and ports 83 can each comprise standard materials and be of similar construction to commercially available introducers, guide catheters, diagnostic catheters, intermediate catheters and microcatheters used in interventional procedures. Delivery catheter 80 can comprise a catheter configured to deliver imaging probe 100 (via lumen 84) to an intracerebral location, an intracardiac location, and/or another location within a patient.

Imaging system 10 can comprise two or more delivery catheters 80, such as three or more delivery catheters 80. Multiple delivery catheters 80 can comprise at least a vascular introducer, and other delivery catheters 80 that can be inserted into the patient therethrough, after the vascular introducer is positioned through the skin of the patient. Two or more delivery catheters 80 can collectively comprise sets of inner diameters (IDs) and outer diameters (ODs) such that a first delivery catheter 80 slidingly receives a second delivery catheter 80 (e.g. the second delivery catheter OD is less than or equal to the first delivery catheter ID), and the second delivery catheter 80 slidingly receives a third delivery catheter 80 (e.g. the third delivery catheter OD is less than or equal to the second delivery catheter ID), and so on. In these configurations, the first delivery catheter 80 can be advanced to a first anatomical location, the second delivery catheter 80 can be advanced through the first delivery catheter to a second anatomical location distal or otherwise remote (hereinafter "distal") to the first anatomical location, and so on as appropriate, using sequentially smaller diameter delivery catheters 80. Probe 100 can be advanced through and/or alongside one or more of the delivery catheters 80 (e.g. through the lumen of the smallest delivery catheter 80). In some embodiments, delivery catheters 80 can be of similar construction and arrangement to the similar components described in applicant's co-pending U.S. patent application Ser. No. 15/751,570, titled "Imaging System includes Imaging Probe and Delivery Devices", filed Feb. 9, 2018.

Imaging probe 100 comprises an elongate body, comprising one or more elongate shafts and/or other tubes, elongate shaft 120 herein. Shaft 120 comprises a proximal end 1201, distal end 1209, and a lumen 1205 extending therebetween. In some embodiments, lumen 1205 includes multiple coaxial lumens within the one or more elongate shafts 120, such as one or more lumens abutting each other to define a single lumen 1205. In some embodiments, at least a portion of shaft 120 comprises a torque shaft. In some embodiments, a portion of shaft 120 comprises a braided construction. Shaft 120 operably surrounds a rotatable optical fiber, optical core 110 (e.g. optical core 110 is positioned within lumen 1205), comprising a proximal end 1101 and a distal end 1109 (proximal end 1101 not shown, but proximate proximal end 1201 of shaft 120). Optical core 110 can comprise a dispersion shifted optical fiber, such as a depressed cladding dispersion shifted fiber. Shaft 120 further comprises a distal portion 1208, including a transparent window, window 130 (e.g. a window that is relatively transparent to the one or more frequencies of light transmitted through optical core 110). Window 130 can comprise a full circumferential portion of distal portion 1208 of shaft 120. An optical assembly, optical assembly 115, is operably attached to the distal end 1109 of optical core 110 (e.g. such that optical assembly 115 rotates in unison with optical core 110). Optical assembly 115 is positioned within window 130 of shaft 120. A connector assembly, connector assembly 150, is positioned on the proximal end of shaft 120. Connector assembly 150 operably attaches imaging probe 100 to rotation assembly 500, such that rotation assembly 500 is operably attached to optical core 110. Rotation assembly 500 can be configured to rotate optical core 110 within shaft 120, as described herein. Connector assembly 150 can be of similar construction and arrangement to similar components described in applicant's co-pending International PCT Patent Application Serial Number PCT/US2018/062766, titled "Imaging System", filed Nov. 28, 2018, and applicant's co-pending U.S. Provisional Patent Application Ser. No. 62/732,114, titled "Imaging System with Optical Pathway", filed Sep. 17, 2018. A second connector, pullback connector 858, is positioned on shaft 120. Connector 858 can be removably attached and/or adjustably positioned along the length of shaft 120. Connector 858 can be positioned along shaft 120, such as by an operator, proximate the proximal end of delivery catheter 80 after imaging probe 100 has been inserted into a patient via delivery catheter 80 (e.g. proximal to connector 82 of delivery catheter 80). Shaft 120 can comprise a portion between connector assembly 150 and the placement location of connector 858 that accommodates slack in shaft 120, a proximal portion of shaft 120 (e.g. a proximal portion of imaging probe 100), service loop 185.

Imaging probe 100 can comprise one or more visualizable markers along its length (e.g. along shaft 120), markers 131a-b shown (marker 131 herein). Marker 131 can comprise markers selected from the group consisting of: radiopaque markers; ultrasonically reflective markers; magnetic markers; ferrous material; visible markers; and combinations of one or more of these. In some embodiments, marker 131 comprises a marker positioned at a location (e.g. a location within and/or at least proximate distal portion 1208) to assist an operator of imaging system 10 in performing a pullback procedure (e.g. a pullback procedure in which fluoroscopy and/or external ultrasound imaging is used), such as to cause distal end 1209 of shaft 120 to be positioned at a location distal to the proximal end of an implant after the pullback is completed (e.g. so that imaging probe 100 can be safely advanced through the implant after the pullback).

In some embodiments, imaging probe 100 includes a viscous damping fluid or other damping material, gel 180, positioned within lumen 1205 of shaft 120, and configured to reduce non-uniform rotation of optical assembly 115. Gel 180 can surround at least a distal portion of optical core 110. Gel 180 can further surround optical assembly 115. Gel 180 can comprise a non-Newtonian fluid, for example a shear-thinning fluid. In some embodiments, gel 180 comprises a static viscosity of at least 500 centipoise, and a shear viscosity that is less than the static viscosity. In these embodiments, the ratio of static viscosity to shear viscosity of gel 180 can be between 1.2:1 and 100:1. Gel 180 can comprise a gel as described in reference to applicant's co-pending U.S. patent application Ser. No. 15/566,041, titled "Micro-Optic Probes for Neurology", filed Oct. 12, 2017, and applicant's co-pending International PCT Patent Application Serial Number PCT/US2018/062766, titled "Imaging System", filed Nov. 28, 2018.

Imaging probe 100 can include a distal tip portion, distal tip 119. In some embodiments, distal tip 119 comprises a spring tip, such as a spring tip configured to improve the "navigability" of imaging probe 100 (e.g. to improve "trackability" and/or "steerability" of imaging probe 100), for example within a tortuous pathway (e.g. within a blood vessel of the brain or heart with a tortuous pathway). In some embodiments, tip 119 comprises a length of between 5 mm and 100 mm (e.g. a spring with a length between 5 mm and 100 mm). Alternatively or additionally, tip 119 can comprise a cap, plug, or other element configured to seal the distal opening of window 130. In some embodiments, tip 119 comprises a radiopaque marker configured to increase the visibility of imaging probe 100 under an X-ray or fluoroscope. In some embodiments, tip 119 comprises a relatively short luminal guidewire pathway to allow "rapid exchange" translation of imaging probe 100.

In some embodiments, at least the distal portion of imaging probe 100 (e.g. the distal portion of shaft 120 surrounding optical assembly 115) comprises an outer diameter of no more than 0.020", or no more than 0.016".

In some embodiments, imaging probe 100 is constructed and arranged for use in an intravascular neural procedure (e.g. a procedure in which the blood, vasculature, and other tissue proximate the brain are visualized, and/or devices positioned temporarily or permanently proximate the brain are visualized). An imaging probe 100 configured for use in a neural procedure can comprise an overall length of at least 150 cm, such as a length of approximately 300 cm.

Alternatively or additionally, imaging probe 100 can be constructed and arranged for use in an intravascular cardiac procedure (e.g. a procedure in which the blood, vasculature, and other tissue proximate the heart are visualized, and/or devices positioned temporarily or permanently proximate the heart are visualized). An imaging probe 100 configured for use in a cardiovascular procedure can comprise an overall length of at least 120 cm, such as an overall length of approximately 280 cm. In some embodiments, imaging probe 100 comprises a length of at least 260 cm and/or at most 320 cm.

Rotation assembly 500 operably attaches to connector 150 of imaging probe 100. Rotation assembly 500 can comprise one or more rotary joints, optical connectors, rotational energy sources, and/or linkages, configured to operably attach and rotate optical core 110. Connector 150 can be constructed and arranged to removably attach to rotation assembly 500, and to allow a rotating connection between proximal end 1101 and a rotating fiber optic joint (such as a fiber optic rotary joint or FORJ). Rotation assembly 500 can be of similar construction and arrangement to similar components described in applicant's co-pending International PCT Patent Application Serial Number PCT/US2018/062766, titled "Imaging System", filed Nov. 28, 2018, and applicant's co-pending U.S. Provisional Patent Application Ser. No. 62/732,114, titled "Imaging System with Optical Pathway", filed Sep. 17, 2018. Rotation assembly 500 can be configured to rotate optical core 110 at speeds of at least 100 rotations per second, such as at least 200 rotations per second or 250 rotations per second, or between 20 rotations per second and 1000 rotations per second. Rotation assembly 500 can comprise a rotational energy source selected from the group consisting of: a motor; a servo; a stepper motor (e.g. a stepper motor including a gear box); a linear actuator; a hollow core motor; and combinations thereof. In some embodiments, rotation assembly 500 is configured to rotate optical assembly 115 and optical core 110 in unison.

Retraction assembly 800 operably attaches to imaging probe 100, such as to retract imaging probe 100 relative to a patient access site. A retraction element 850 can operably attach to retraction assembly 800 and imaging probe 100, such as to transfer a retraction force from retraction assembly 800 to imaging probe 100. Retraction element 850 can comprise a conduit 855, surrounding a linkage 856, slidingly received therein. Retraction element 850 can comprise a connector 852, that operably attaches to retraction assembly 800, such that retraction assembly 800 can retract linkage 856 relative to conduit 855. In some embodiments, conduit 855 comprises a connector 857 that operably attaches to a reference point near the patient access site, for example to connector 82 of delivery catheter 80, such as to establish a reference for retraction of imaging probe 100 relative to the patient. Connector 857 can attach to a reference point such as a patient introduction device, surgical table, and/or another fixed or semi fixed point of reference. Linkage 856 releasably attaches to connector 858 of imaging probe 100. Retraction assembly 800 retracts at least a portion of imaging probe 100 (e.g. the portion of imaging probe 100 distal to the attached connector 858), relative to the established reference by retracting linkage 856 relative to conduit 855 (e.g. retract a portion of linkage 856 exiting a portion of conduit 855, as shown). In some embodiments, retraction assembly 800 is configured to retract at least a portion of imaging probe 100 (e.g. at least optical assembly 115 and a portion of shaft 120) at a rate of between 5 mm/sec and 200 mm/sec, or between 5 mm/sec and 100 mm/sec, such as a rate of approximately 60 mm/sec. Additionally or alternatively, the pullback procedure can be performed during a time period of between 0.5 sec and 25 sec, for example approximately 20 sec (e.g. over a distance of 100 mm at 5 mm/sec). Service loop 185 of imaging probe 100 can be positioned between connector 857, and rotation assembly 500, such that imaging probe 100 can be retracted relative to the patient while rotation assembly 500 remains stationary (e.g. attached to the surgical table and/or to a portion of console 50).

Retraction assembly 800 further comprises a motive element configured to retract linkage 856. In some embodiments, the motive element comprises a linear actuator, a worm drive operably attached to a motor, a pulley system, and/or other linear force transfer mechanisms. Linkage 856 can be operably attached to the motive element via one or more linkages and/or connectors. Retraction assembly 800 can be of similar construction and arrangement to similar components described in applicant's co-pending International PCT Patent Application Serial Number PCT/US2018/062766, titled "Imaging System", filed Nov. 28, 2018.

In some embodiments, imaging system 10 comprises a patient interface unit 200. Patient interface unit 200 can comprise a single housing, containing both rotation assembly 500 and retraction assembly 800. Alternatively or additionally, patient interface unit 200 can comprise two or more housings, such as a separate housing for each of rotation assembly 500 and retraction assembly 800. In some embodiments, connector 150, service loop 185, retraction element 850, and connector 852 are housed in a single housing, configured to operably attach to both rotation assembly 500 and retraction assembly 800 (e.g. such as when rotation assembly 500 and retraction assembly 800 are housed within a single housing).

Console 50 comprises an imaging assembly 300, a user interface 55, processor 52, and one or more algorithms 51. Imaging assembly 300 can be configured to provide light to optical assembly 115 (e.g. via optical core 110) and collect light from optical assembly 115 (e.g. via optical core 110). Imaging assembly 300 can include a light source 310. Light source 310 can comprise one or more light sources, such as one or more light sources configured to provide one or more wavelengths of light to optical assembly 115 via optical core 110. Light source 310 is configured to provide light to optical assembly 115 (via optical core 110) such that image data can be collected comprising cross-sectional, longitudinal and/or volumetric information related to a patient site or implanted device being imaged. Light source 310 can be configured to provide light such that the image data collected includes characteristics of tissue within the patient site being imaged, such as to quantify, qualify or otherwise provide information related to a patient disease or disorder present within the patient site being imaged. Light source 310 can be configured to deliver broadband light and have a center wavelength in the range from 350 nm to 2500 nm, from 800 nm to 1700 nm, from 1280 nm to 1310 nm, or approximately 1300 nm (e.g. light delivered with a sweep range from 1250 nm to 1350 nm). Light source 310 bandwidth can be selected to achieve a desired resolution, which can vary according to the needs of the intended use of imaging system 10. In some embodiments, bandwidths are about 5% to 15% of the center wavelength, which allows resolutions of between 20 µm and 5 µm. Light source 310 can be configured to deliver light at a power level meeting ANSI Class 1 ("eye safe") limits, though higher power levels can be employed. In some embodiments, light source 310 delivers light in the 1.3 µm band at a power level of approximately 20 mW. Tissue light scattering is reduced as the center wavelength of delivered light increases, however water absorption increases. Light source 310 can deliver light at a wavelength approximating 1300 nm to balance these two effects. Light source 310 can be configured to deliver shorter wavelength light (e.g. approximately 800 nm light) to traverse patient sites to be imaged including large amounts of fluid. Alternatively or additionally, light source 310 can be configured to deliver longer wavelengths of light (e.g. approximately 1700 nm light), such as to reduce a high level of scattering within a patient site to be imaged. In some embodiments, light source 310 comprises a tunable light source (e.g. light source 310 emits a single wavelength that changes repetitively over time), and/or a broad-band light source. Light source 310 can comprise a single spatial mode light source or a multimode light source (e.g. a multimode light source with spatial filtering). Imaging assembly 300 can be of similar construction and arrangement to similar components described in applicant's co-pending U.S. Provisional Patent Application Ser. No. 62/732,114, titled "Imaging System with Optical Pathway", filed Sep. 17, 2018.

Console 50 can comprise one or more algorithms, such as algorithm 51 shown, which can be configured to adjust (e.g. automatically and/or semi-automatically adjust) one or more operational parameters of imaging system 10, such as an operational parameter of console 50, imaging probe 100 and/or a delivery catheter 80. Console 50 can further comprise a processing assembly, processor 52, configured to execute algorithm 51, and/or perform any type of data processing, such as digital signal processing, described herebelow in reference to FIG. 4. Additionally or alternatively, algorithm 51 can be configured to adjust an operational parameter of a separate device, such as injector 20 or implant delivery device 30 described herebelow. In some embodiments, algorithm 51 is configured to adjust an operational parameter based on one or more sensor signals, such as a sensor signal provided by a sensor-based functional element of the present inventive concepts as described herein. Algorithm 51 can be configured to adjust an operational parameter selected from the group consisting of: a rotational parameter such as rotational velocity of optical core 110 and/or optical assembly 115; a retraction parameter of shaft 120 and/or optical assembly 115 such as retraction velocity, distance, start position, end position and/or retraction initiation timing (e.g. when retraction is initiated); a position parameter such as position of optical assembly 115; a line spacing parameter such as lines per frame; an image display parameter such as a scaling of display size to vessel diameter; an imaging probe 100 configuration parameter; an injectate 21 parameter such as a saline to contrast ratio configured to determine an appropriate index of refraction; a light source 310 parameter such as power delivered and/or frequency of light delivered; and combinations of one or more of these. In some embodiments, algorithm 51 is configured to adjust a retraction parameter such as a parameter triggering the initiation of the pullback, such as a pullback that is initiated based on a parameter selected from the group consisting of: lumen flushing (the lumen proximate optical assembly 115 has been sufficiently cleared of blood or other matter that would interfere with image creation); an indicator signal is received from injector 20 (e.g. a signal indicating sufficient flushing fluid has been delivered); a change in image data collected (e.g. a change in an image is detected, based on the image data collected, that correlates to proper evacuation of blood from around optical assembly 115); and combinations of one or more of these. In some embodiments, algorithm 51 is configured to adjust an imaging system 10 configuration parameter related to imaging probe 100, such as when algorithm 51 identifies (e.g. automatically identifies via an RF or other embedded ID) the attached imaging probe 100 and adjusts an imaging system 10 parameter, such as an arm path length parameter, a dispersion parameter, and/or other parameter as listed above.

Imaging system 10 can comprise one or more interconnect cables, bus 58 shown. Bus 58 can operably connect rotation assembly 500 to console 50, retraction assembly 800 to console 50, and or rotation assembly 500 to retraction assembly 800 (e.g. by connecting patient interface unit 200 to console 50). Bus 58 can comprise one or more optical transmission fibers, electrical transmission cables, fluid conduits, and combinations of one or more of these. In some embodiments, bus 58 comprises at least an optical transmission fiber that optically couples rotation assembly 500 to imaging assembly 300 of console 50. Additionally or alternatively, bus 58 comprises at least power and/or data transmission cables that transfer power and/or motive information to retraction assembly 800.

User interface 55 can comprise an output 56 and an input 57. Output 56 can comprise one or more outputs selected from the group consisting of: a screen; an indicator light; a tactile transducer such as a vibrational transducer; a speaker; an output signal, such as a wireless signal, to be received by an external device; and combinations of these. Input 57 can comprise an input selected from the group consisting of: a button; two or more buttons; a touch screen; a mouse; an input signal, such as a wireless signal received from an external device; and combinations of these. In some embodiments, output 56 and/or input 57 are integrated into patient interface unit 200, and/or either or both of rotational assembly 500 and retraction assembly 800.

Second imaging device 15 can comprise an imaging device such as one or more imaging devices selected from the group consisting of: an X-ray; a fluoroscope such as a single plane or biplane fluoroscope; a CT Scanner; an MRI; a PET Scanner; an ultrasound imager; and combinations of one or more of these. In some embodiments, second imaging device 15 comprises a device configured to perform rotational angiography.

Treatment device 16 can comprise an occlusion treatment or other treatment device selected from the group consisting of: a balloon catheter constructed and arranged to dilate a stenosis or other narrowing of a blood vessel; a drug eluting balloon; an aspiration catheter; a sonolysis device; an atherectomy device; a thrombus removal device such as a stent retriever device; a Trevo™ stentriever; a Solitaire™ stentriever; a Revive™ stentriever; an Eric™ stentriever; a Lazarus™ stentriever; a stent delivery catheter; a microbraid implant; an embolization system; a WEB™ embolization system; a Luna™ embolization system; a Medina™ embolization system; and combinations of one or more of these. In some embodiments, imaging probe 100 is configured to collect data related to treatment device 16 (e.g. treatment device 16 location, orientation and/or other configuration data), after treatment device 16 has been inserted into the patient.

Injector 20 can comprise a power injector, syringe pump, peristaltic pump or other fluid delivery device configured to inject a contrast agent, such as radiopaque contrast, and/or other fluids. In some embodiments, injector 20 is configured to deliver contrast and/or other fluid (e.g. contrast, saline and/or Dextran). In some embodiments, injector 20 delivers fluid in a flushing procedure as described herebelow. In some embodiments, injector 20 delivers contrast or other fluid through a delivery catheter 80 with an ID of between 5 Fr and 9 Fr, a delivery catheter 80 with an ID of between 0.53" to 0.70", or a delivery catheter 80 with an ID between 0.0165" and 0.027". In some embodiments, contrast or other fluid is delivered through a delivery catheter as small as 4 Fr (e.g. for distal injections). In some embodiments, injector 20 delivers contrast and/or other fluid through the lumen of one or more delivery catheters 80, while one or more smaller delivery catheters 80 also reside within the lumen. In some embodiments, injector 20 is configured to deliver two dissimilar fluids simultaneously and/or sequentially, such as a first fluid delivered from a first reservoir and comprising a first concentration of contrast, and a second fluid from a second reservoir and comprising less or no contrast.

Injectate 21 can comprise fluid selected from the group consisting of: optically transparent material; saline; visualizable material; contrast; Dextran; an ultrasonically reflective material; a magnetic material; and combinations thereof. Injectate 21 can comprise contrast and saline. Injectate 21 can comprise at least 20% contrast. During collection of image data, a flushing procedure can be performed, such as by delivering one or more fluids, injectate 21 (e.g. as propelled by injector 20 or other fluid delivery device), to remove blood or other somewhat opaque material (hereinafter non-transparent material) proximate optical assembly 115 (e.g. to remove non-transparent material between optical assembly 115 and a delivery catheter and/or non-transparent material between optical assembly 115 and a vessel wall), such as to allow light distributed from optical assembly 115 to reach and reflectively return from all tissue and other objects to be imaged. In these flushing embodiments, injectate 21 can comprise an optically transparent material, such as saline. Injectate 21 can comprise one or more visualizable materials, as described herebelow.

As an alternative or in addition to its use in a flushing procedure, injectate 21 can comprise material configured to be viewed by second imaging device 15, such as when injectate 21 comprises a contrast material configured to be viewed by a second imaging device 15 comprising a fluoroscope or other X-ray device; an ultrasonically reflective material configured to be viewed by a second imaging device 15 comprising an ultrasound imager; and/or a magnetic material configured to be viewed by a second imaging device 15 comprising an Mill.

Implant 31 can comprise an implant (e.g. a temporary or chronic implant) for treating one or more of a vascular occlusion or an aneurysm. In some embodiments, implant 31 comprises one or more implants selected from the group consisting of: a flow diverter; a Pipeline™ flow diverter; a Surpass™ flow diverter; an embolization coil; a stent; a Wingspan™ stent; a covered stent; an aneurysm treatment implant; and combinations of one or more of these.

Implant delivery device 30 can comprise a catheter or other tool used to deliver implant 31, such as when implant 31 comprises a self-expanding or balloon expandable portion. In some embodiments, imaging system 10 comprises imaging probe 100, one or more implants 31 and/or one or more implant delivery devices 30. In some embodiments, imaging probe 100 is configured to collect data related to implant 31 and/or implant delivery device 30 (e.g. implant 31 and/or implant delivery device 30 anatomical location, orientation and/or other configuration data), after implant 31 and/or implant delivery device 30 has been inserted into the patient.

In some embodiments, one or more system components, such as console 50, delivery catheter 80, imaging probe 100, patient interface unit 200, rotation assembly 500, retraction assembly 800, treatment device 16, injector 20, and/or implant delivery device 30, further comprise one or more functional elements ("functional element" herein), such as functional elements 59, 89, 199, 299, 599, 899, 99a, 99b, and/or 99c, respectively, shown. Each functional element can comprise at least two functional elements. Each functional element can comprise one or more elements selected from the group consisting of: sensor; transducer; and combinations thereof. The functional element can comprise a sensor configured to produce a signal. The functional element can comprise a sensor selected from the group consisting of: a physiologic sensor; a pressure sensor; a strain gauge; a position sensor; a GPS sensor; an accelerometer; a temperature sensor; a magnetic sensor; a chemical sensor; a biochemical sensor; a protein sensor; a flow sensor such as an ultrasonic flow sensor; a gas detecting sensor such as an ultrasonic bubble detector; a sound sensor such as an ultrasound sensor; and combinations thereof. The sensor can comprise a physiologic sensor selected from the group consisting of: a pressure sensor such as a blood pressure sensor; a blood gas sensor; a flow sensor such as a blood flow sensor; a temperature sensor such as a blood or other tissue temperature sensor; and combinations thereof. The sensor can comprise a position sensor configured to produce a signal related to a vessel path geometry (e.g. a 2D or 3D vessel path geometry). The sensor can comprise a magnetic sensor. The sensor can comprise a flow sensor. The system can further comprise an algorithm configured to process the signal produced by the sensor-based functional element. Each functional element can comprise one or more transducers. Each functional element can comprise one or more transducers selected from the group consisting of: a heating element such as a heating element configured to deliver sufficient heat to ablate tissue; a cooling element such as a cooling element configured to deliver cryogenic energy to ablate tissue; a sound transducer such as an ultrasound transducer; a vibrational transducer; and combinations thereof.

In some embodiments, imaging probe 100 comprises a "bubble-handling" mechanism, fluid pressurization element (FPE) 1500 shown, such as for preventing or at least reducing the presence of bubbles proximate optical assembly 115, as described in detail herein. FPE 1500 can be configured to generate a pressure differential within a volume of gel 180 and/or otherwise to increase the pressure of one or more volumes of gel 180. FPE 1500 can comprise a distal end that is placed relatively proximate the proximal end of optical assembly 115. In some embodiments, FPE 1500 is configured to increase the pressure of and/or generate a pressure differential within a volume of gel 180 that is proximate optical assembly 115. Additionally or alternatively, FPE 1500 can generate a flow of gel 180 (e.g. a flow of gel 180 including one or more bubbles, such as to move the bubbles away from optical assembly 115). FPE 1500 can comprise a projection extending from optical core 110 that increases the pressure of gel 180 when FPE 1500 is rotated (via rotation of optical core 110). Alternatively or additionally, FPE 1500 can comprise a pump, pressurized vessel, and/or other pressurization source ("pump" herein) that is fluidly attached to one or more lumens (e.g. lumen 1205 of shaft 120), such as to increase the pressure of gel 180 (e.g. intermittently and on demand by system 10).

As shown in FIG. 1A, one or more air bubbles B can exist within gel 180. For example, as optical core 110 and optical assembly 115 rotate within gel 180, bubbles B can form, such as via cavitation and/or other bubble-forming anomalies as described hereabove. Additionally or alternatively, one or more bubbles B can (already) exist within gel 180, such as a result of a manufacturing process of imaging probe 100. In operation, bubbles B proximate optical assembly 115 can cause unwanted imaging artifacts and/or other imaging issues. FPE 1500 can be constructed and arranged to prevent or at least reduce bubbles B from forming, reduce expansion of one or more bubbles B, reduce the size of one or more bubbles B, and/or move one or more bubbles away from optical assembly 115. In an initial start-up condition (e.g. when FPE 1500 has just started rotating) the pressure of gel 180 distal to FPE 1500 increases, bubbles distal to FPE 1500 move distally and compress due to the increasing pressure, and bubbles proximal to FPE 1500 initially move toward FPE 1500 (as fluid is moving to fill the space created by the compressing bubble), but then stop moving once an equilibrium pressure gradient is reached, In some embodiments, FPE 1500 is configured to manipulate (e.g. propel) gel 180, such as to generate a high-pressure area HP surrounding optical assembly 115 (e.g. a volume of gel 180 that is proximate optical assembly 115), and a low-pressure area LP proximal to FPE 1500 (e.g. a volume of gel 180 that is proximal to optical assembly 115).

In some embodiments, one or more bubbles B may become trapped distal to high-pressure area HP, however FPE 1500 is constructed and arranged to manipulate gel 180 proximate optical assembly 115, such as to prevent any bubbles B from becoming trapped proximate assembly 115 (e.g. the distally trapped bubbles B do not migrate toward optical assembly 115). Additionally or alternatively, the increased pressure of high-pressure area HP can cause a reduction in size of any existing bubbles B proximate optical assembly 115 (e.g. a compression of any bubbles B within high pressure area HP) and/or the increased pressure can prevent new bubbles B from forming. In some embodiments, high pressure area HP generated by FPE 1500 comprises a pressure of at least 3.6 psi (e.g. at least approximately 0.25 atmospheres), such as a pressure of at least 5 psi, at least 10 psi, at least 15 psi, at least 20 psi, at least 30 psi, and/or at least 40 psi. In some embodiments, FPE 1500 generates pressure in area HP of at least 75 psi, at least 100 psi, at least 125 psi, and/or at least 150 psi. In some embodiments, high pressure-area HP comprises a pressure at least 5 psi above low pressure area LP, such as at least 10 psi, at least 20 psi, and/or at least 30 psi greater than the pressure of low pressure area LP. In some embodiments, each bubble B undergoes a compression of two or three times (i.e. ½ or ⅓ the original size) under the high-pressure conditions of high-pressure area HP.

In some embodiments, gel 180 comprises a low viscosity fluid, such as a shear thinning fluid with a low starting viscosity, such that bubbles B have a lower likelihood of formation. For example, gel 180 can comprise a viscosity of 1000 centipoise or less. Additionally or alternatively, gel 180 can comprise a high surface tension, such as a surface tension of at least 40 dynes/cm, again such that bubbles B have a lower likelihood of formation.

In some embodiments, gel 180 is pressurized by a pump (e.g. intermittently pressurized to a pressure at or above atmospheric pressure), such as when lumen 1205 is pressurized, such as via a pump fluidly connected to lumen 1205 and located within console 50 or patient interface unit 200 (e.g. FPE 1500 comprises this pump that is fluidly attached but external to lumen 1205). In some embodiments, gel 180 is pressurized by an external source, and FPE 1500 is constructed and arranged to generate (e.g. when rotated) a pressure differential within gel 180 in addition to the pressure applied by the separate pump. Intermittent pressurization (e.g. via an external pump or via rotation of FPE 1500) can provide numerous advantages, such as to prevent the increase of dissolved gasses in gel 180 that would result from constant applied pressure, as described herein.

Figure 2:
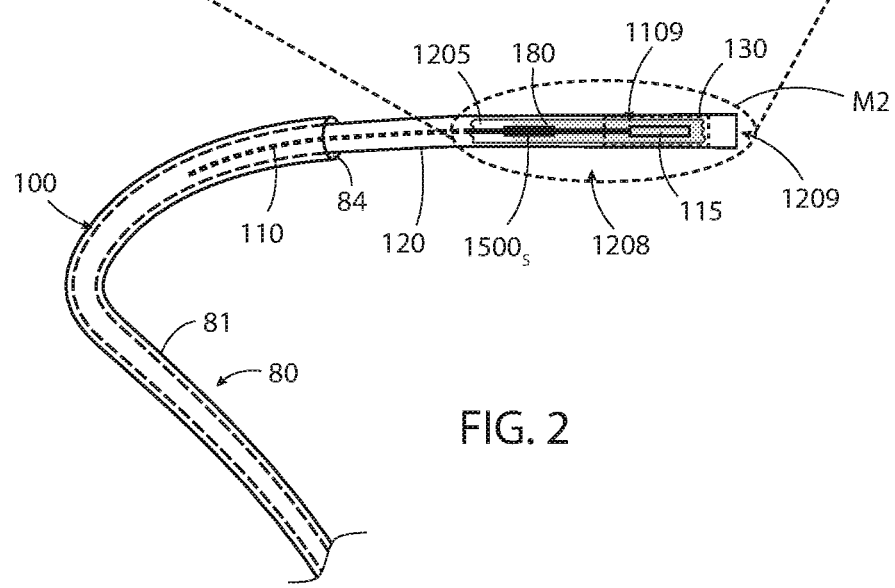

In some embodiments, FPE 1500 comprises a helical projection radially extending from optical core 110 that is configured to increase pressure of gel 180 and/or generate a pressure differential within gel 180 when optical core 110 is rotated, such as is described herebelow in reference to FIG. 2. In some embodiments, FPE 1500 comprises one or more radially extending projections from optical core 110, configured to generate a pressure differential in gel 180 when optical core 110 is rotated, such as is described herebelow in reference to FIG. 3. In some embodiments, FPE 1500 comprises a pump, pressurized vessel, and/or other pressurization source ("pump" herein), such as a fluid conduit fluidly attached to a pump on its proximal end, and exiting into lumen 1205 proximate optical assembly 115, as described herebelow in reference to FIG. 4.

In some embodiments, FPE 1500 is configured to operate intermittently, such as to intermittently increase the pressure of gel 180 such as to intermittently generate a pressure differential within gel 180. For example, FPE 1500 can comprise one or more radially extending projections from optical core 110 that are configured to generate a pressure differential in gel 180 only when optical core 110 is rotating, such as is described herebelow in reference to FIG. 4A. In these embodiments, while FPE 1500 is not operating (e.g. not being rotated), the pressure of gel 180 can normalize, such as to a pressure lower than that of high pressure-area HP while FPE 1500 is operating (e.g. is being rotated). Intermittent pressurizing can be implemented to prevent the increase of dissolved gasses in gel 180. In some embodiments, FPE 1500 is configured to operate continuously only for limited time periods, such as discrete time periods of no more than 2 minutes at a time, such as no more than 30 seconds, or no more than 5 seconds (e.g. to intermittently pressure gel 180 to prevent undesired dissolved gases in gel 180).

Referring now to FIGS. 2 and 2A, a schematic view of the distal portion of an imaging probe and delivery catheter, and a magnified view of the components within circle M2, are illustrated, respectively, consistent with the present inventive concepts. Imaging probe 100 and delivery catheter 80 can be of similar construction and arrangement to imaging probe 100 and delivery catheter 80 described hereabove in reference to FIGS. 1 and 1A. In the embodiment shown in FIGS. 2-2A, the fluid pressurization mechanism, FPE $1500_S$ shown, comprises a helical projection radially extending from optical core 110. During operation, as optical core 110 rotates, FPE $1500_S$ rotates in unison, generating a fluid flow proximate FPE $1500_S$, and causing a pressure gradient within gel 180 (e.g. across FPE $1500_S$). Modeling of examples of the fluid flow dynamics are described hereinbelow in reference to FIG. 2B-C.

In some embodiments, FPE $1500_S$ comprises a helical coil, such as a spring or other wound wire, affixed along a portion of the length of optical core 110 (e.g. surrounding core 110). FPE $1500_S$ can be adhered, such as via glue or another adhesive, to optical core 110. In some embodiments, FPE $1500_S$ is molded on and/or with core 110, formed into (e.g. such as via a material removal process) core 110, fused onto core 110, and/or otherwise manufactured with or adhered to core 110. In some embodiments, FPE $1500_S$ comprises a material selected from the group consisting of: metal; plastic; stainless steel; nickel-titanium alloy; nylon; polyether ether ketone (PEEK); polyimide; and combinations of these. In some embodiments, FPE $1500_S$ can be formed directly onto optical core 110, such as using a deposition technique and/or 3D printing technique. In some embodiments, a selectively curable material is applied to optical core 110 and cured in a spiral pattern to form FPE $1500_S$. For example, a high-strength UV-cured adhesive can be applied to the surface of optical core 110 and selectively cured using a rotating, focused UV beam. In some embodiments, FPE $1500_S$ can comprise a material selected to minimize deformation of FPE $1500_S$ while the pressure gradient is applied. For example, during rotation a pressure gradient occurs across the length of FPE $1500_S$, such that to prevent deformation, a shorter FPE $1500_S$ would require a stiffer material than a longer FPE $1500_S$ configured to produce the same pressure gradient.

FPE $1500_S$ comprises a radial height, height $H_1$, which is the distance from the surface of optical core 110 to the outer edge of FPE $1500_S$. Optical core 110 comprises a diameter $D_1$. Lumen 1205 of shaft 120 comprises an internal diameter $D_2$. In some embodiments, diameters $D_1$ and $D_2$ vary along the length of probe 100, and the following dimensions relate to a segment of probe 100, such as a distal segment shown in FIG. 2A (e.g. a segment proximal and proximate optical assembly 115). Probe 100 can comprise a clearance $C_1$, between FPE $1500_S$ (e.g. the outer diameter of FPE $1500_S$) and the inner wall of shaft 120. Clearance $C_1$ relates both to the difference between diameter $D_1$ and $D_2$, and the height $H_1$ of FPE $1500_S$, such that $C_1$ equals one half of the difference between $D_1$ and $D_2$ minus $H_1$. In some embodiments, clearance $C_1$ comprises a clearance of no more than 100 µm, such as no more than 75 µm, such as between 10 µm and 75 µm. In some embodiments, height $H_1$ comprises a height that is between 5% and 95% of half the difference between $D_1$ and $D_2$, (e.g. a height $H_1$ that occupies at least 5% and/or no more than 95% of the space between the outer surface of core 110 and the inner wall of shaft 120). In some embodiments, the optimal height $H_1$ depends on factors such as: damping fluid viscosity (e.g. gel 180 viscosity); desired rotational rate of optical core 110; desired pressure gradient; and/or the clearance between FPE $1500_S$ and the inner wall of shaft 120 (e.g. tighter clearances create higher pressures). In some embodiments, the coil profile of FPE $1500_S$ comprises a width $W_1$ as shown. Width $W_1$ can comprise a width of 1% to 95% of diameter $D_1$. FPE $1500_S$ can also comprise a pitch $P_1$ as shown. Pitch $P_1$ can comprise a pitch such that the gap between adjacent coils is 0.5 to 20 times the diameter $D_1$. In some embodiments, adjacent coils do not come into contact with each other. In some embodiments, pitch $P_1$ is uniform along the length of FPE $1500_S$. In some embodiments, pitch P1 can comprise a pitch between 0.2 mm and 1.2 mm, such as a pitch of approximately 0.5 mm or 1 mm. In some embodiments, the length of FPE $1500_S$ and/or Pitch P1 can be selected to achieve a desired pressure to be generated when optical core 110 is rotated.

In some embodiments, gel 180 comprises a high viscosity, shear thinning fluid, such as is described hereabove in reference to FIG. 1. In some embodiments, the maximum functional clearance $C_1$ (e.g. the largest clearance $C_1$ allowable such that rotation of FPE $1500_S$ generates sufficient fluid pressurization within lumen 1205), is proportional to the viscosity of gel 180. For example, the higher the viscosity of gel 180, the greater the maximum clearance $C_1$. In some embodiments, the clearance $C_1$ is proportional to the pressure differential that can be generated within gel 180 by rotating FPE $1500_S$, as described hereabove. For example, the smaller clearance $C_1$, the greater the pressure differential that can be generated. In some embodiments, clearance $C_1$ and height $H_1$ are minimized to limit turbulent, recirculatory, and/or other unwanted fluid flow proximate optical core 110. In some embodiments, gel 180 comprises a Newtonian (non-shear thinning) fluid. The dimensions $C_1$, $H_1$, $D_1$, and $D_2$ can be optimized for differing properties of gel 180.

In some embodiments, FPE $1500_S$ comprises a covering (not shown). The covering can comprise a sheath, such as a heat shrink tube, and/or a painted or sprayed on coating. The covering can be configured to improve the bonding of FPE $1500_S$ to optical core 110, and/or to control the dimensions of FPE $1500_S$ (e.g. to hold FPE $1500_S$ tightly to optical core 110, such as to limit unwanted variations in height $H_1$). Additionally or alternatively, the covering can be configured to modify the surface properties of either or both of optical core 110 and FPE $1500_S$. In some embodiments, the covering comprises a thickness that does not significantly affect the fluid propulsion and/or other fluid pressurization ("fluid pressurization" herein) performance of FPE $1500_S$. Alternatively or additionally, FPE $1500_S$ can be constructed and arranged such that the dimensions $C_1$, $H_1$, and $D_1$ are optimal after the application of the covering.

In some embodiments, the pressurization of gel 180 within lumen 1205 caused by the rotation of FPE $1500_S$ exerts a functional torsional sheer force on the inner wall of lumen 1205. Shaft 120 can comprise a torsional resistance greater than the functional torsional sheer force exerted by gel 180. In some embodiments, gel 180 exerts a torque of approximately 0.004 N-cm, and shaft 120 comprises a torsional resistance of at least 0.01 N-cm, such as 0.03 N-cm. Additionally or alternatively, FPE $1500_S$ can exert a "wind-up" stress on optical core 110 as optical core 110 is rotated, driving FPE $1500_S$ within gel 180. Optical core 110 can be constructed and arranged to not be adversely affected by (e.g. not break or otherwise fail) the sheer stress induced by the rotation of core 110 and FPE 1500, within gel 180 as well as the shear stress induced by the pullback motion within gel 180. In some embodiments, the additional windup stress on optical core 110 caused by FPE $1500_S$ functions as a NURD reduction mechanism, similar to NURD reduction caused by gel 180, as described in applicant's co-pending International PCT Patent Application Serial Number PCT/US2018/062766, titled "Imaging System", filed Nov. 28, 2018.

Figure 2B:
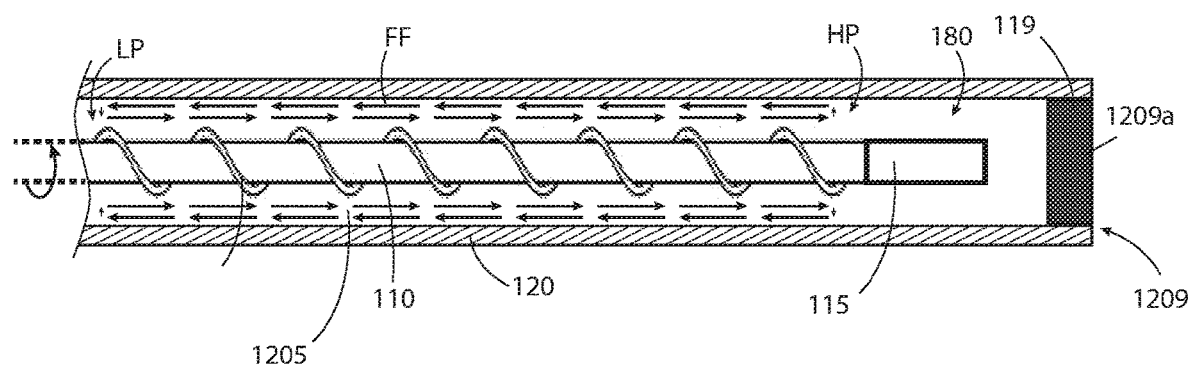
FIGS. 2B and 2C illustrate a schematic view of the distal portion of an imaging probe showing a fluid flow pattern, and a fluid flow simulation, respectively, consistent with the present inventive concepts.
Figure 2C:
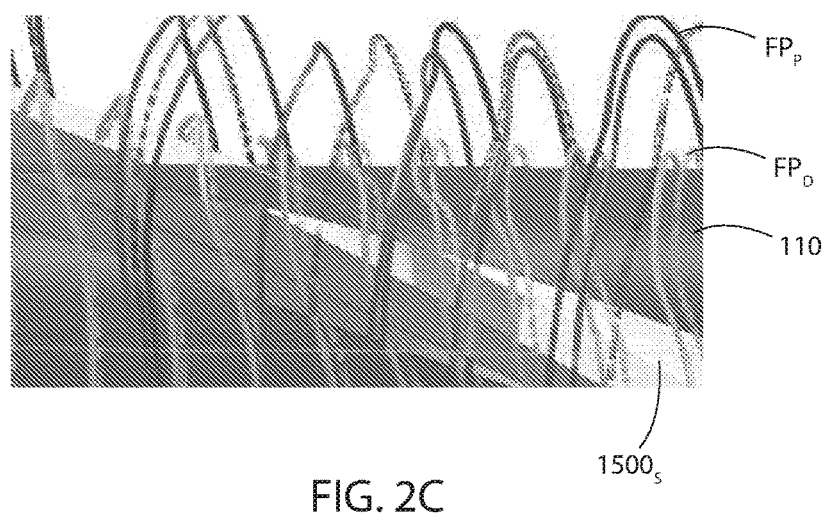

Referring additionally to FIGS. 2B and 2C, a schematic view of the distal portion of an imaging probe showing a fluid flow pattern, and a fluid flow simulation, are illustrated, respectively, consistent with the present inventive concepts. The motion of gel 180 is depicted by fluid flow arrows FF in FIG. 2B, and paths $FP_P$ and $FP_D$ in FIG. 2C. Optical core 110 and FPE $1500_S$ are depicted rotating with the top edge of FPE $1500_S$ rotating into the page. Along with the axial motion shown, a fluid flow comprises a rotational component as well, shown in FIG. 2C. The distal end 1209 and/or at least a distal portion of shaft 120 can be sealed, such as when distal tip 119 comprises a cap or plug configured as a sealing element, plug 1209a shown in FIG. 2B. Rotation of FPE $1500_S$ as shown causes a fluid flow proximate optical core 110 in the distal direction towards high pressure area HP. As the pressure within high pressure area HP increases to match the pressure of the distal fluid flow, a closed loop recirculation pattern emerges, as shown. Fluid propelled distally by FPE $1500_S$ encounters the pressure within high pressure area HP and redirects proximally along the surface of lumen 1205 (e.g. along a path of least resistance). This fluid flow pattern creates a "dead head" pressure profile (e.g. there is no net fluid flow), maintaining the pressure gradient along FPE $1500_S$, from low pressure area LP to high pressure area HP. As shown in FIG. 2C, fluid paths $FP_D$ depict fluid flow proximate optical core 110, distally towards high pressure area HP. Fluid paths $FP_P$ depict fluid flow proximate the surface of lumen 1205, proximally towards low pressure area LP.

Figure 3A:
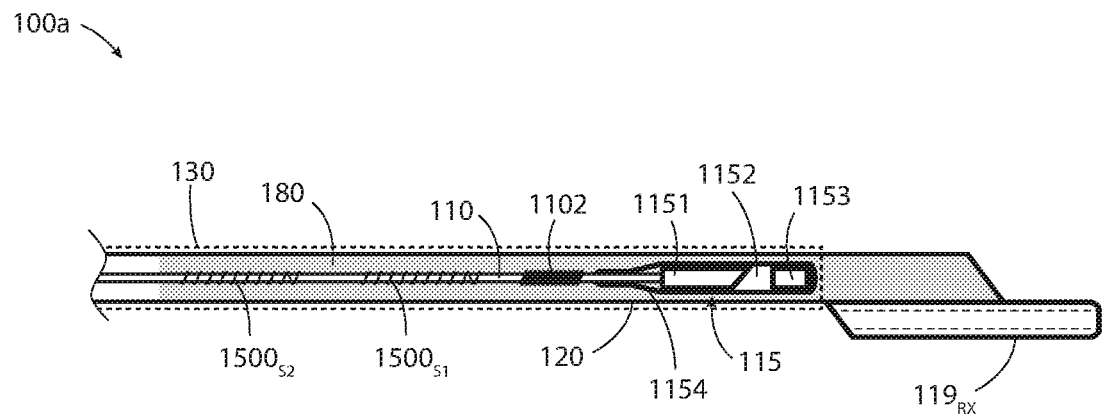
FIGS. 3A and 3B illustrate schematic views of the distal portion of imaging probes, consistent with the present inventive concepts.
Figure 3B:
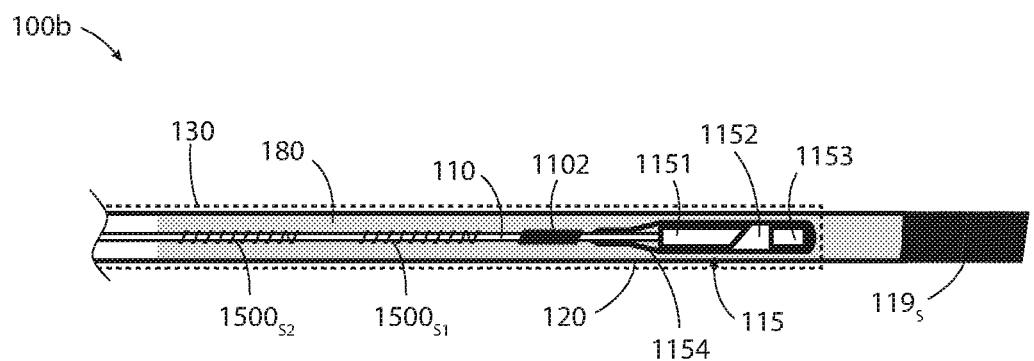

Referring now to FIGS. 3A and 3B, schematic views of the distal portion of two imaging probes including a fluid propulsion element are illustrated, consistent with the present inventive concepts. FIG. 3A illustrates the distal portion of imaging probe 100a, including a rapid exchange distal tip $119_{RX}$. FIG. 3B illustrates the distal portion of imaging probe 100b, including a spring tip $119_S$. Imaging probes 100a and 100b of FIGS. 3A and 3B can comprise similar components and be of similar construction and arrangement to imaging probe 100 of FIGS. 1 and 1A described hereabove. Optical assembly 115 can comprise a lens assembly, assembly 1151, which is optically and physically coupled to the distal end of optical core 110. Lens assembly 1151 can comprise a GRIN lens comprising a beveled distal end. The beveled distal end of lens assembly 1151 can comprise a total internally reflective surface. An elongate tube, tube 1154, surrounds at least a distal portion of optical core 110, lens assembly 1151, and a sealing element, plug 1153 (e.g. a sealing element similar to plug 1209a of FIG. 2B). Tube 1154 can comprise a heat shrink material. Tube 1154 can comprise PET. At least a portion of tube 1154 can be glued, or otherwise adhered, to at least a portion of lens assembly 1151, optical core 110, and/or plug 1153. Plug 1153 is configured to prevent and/or limit the egress of gel 180 into a cavity created between lens assembly 1151 and plug 1153, space 1152 shown. Space 1152 can be filled with air and/or one or more other fluids. The fluid within space 1152 can be configured to provide desired optical properties between lens assembly 1151 and the fluid (e.g. provide a glass-air interface). Optical core 110 can comprise a support element 1102. Support element 1102 can comprise a torque wire positioned proximal to optical assembly 115. Support element 1102 can be configured to reinforce a distal portion of optical core 110, such as to provide a rotational reinforcement to optical core 110.

In some embodiments, FPE 1500 comprises two fluid propulsion elements, such as FPE $1500_{S1}$ and $1500_{S2}$, as shown in FIGS. 3A and 3B. Distal FPE $1500_{S1}$ can be configured to produce the pressure gradient across optical assembly 115, as described herein. Additionally, proximal FPE $1500_{S2}$ can be configured to prevent or otherwise minimize gel 180 from migrating proximally (e.g. beyond FPE $1500_{S2}$) and/or to prevent cavitation proximate FPE $1500_{S1}$ (e.g. "priming" FPE $1500_{S1}$ with gel 180 such as to prevent bubble formation proximate FPE $1500_{S1}$). FPE $1500_{S2}$ can be positioned proximate the proximal end of gel 180 (e.g. proximate the position within shaft 120 to where gel 180 is inserted from the distal end of shaft 120 during manufacturing).

Figure 4A:
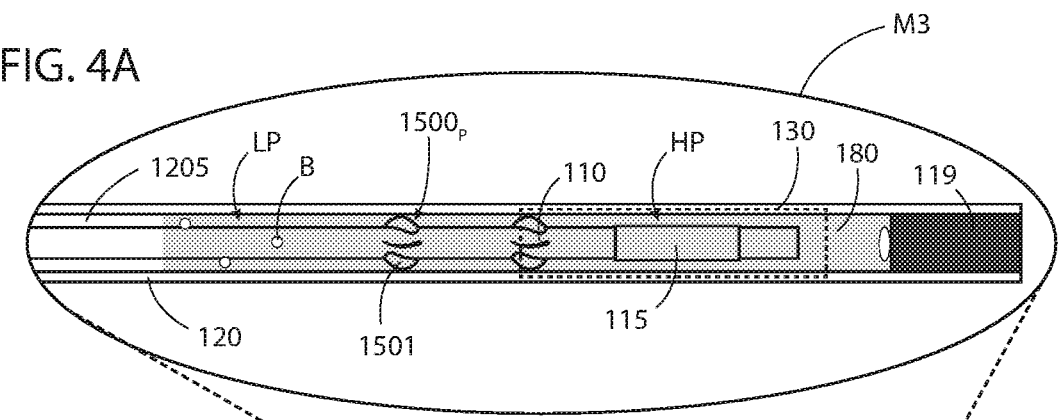
FIGS. 4 and 4A illustrate a schematic view of the distal portion of an imaging probe and delivery catheter, and a magnified view of the components within circle M3, respectively, consistent with the present inventive concepts.
Figure 4:
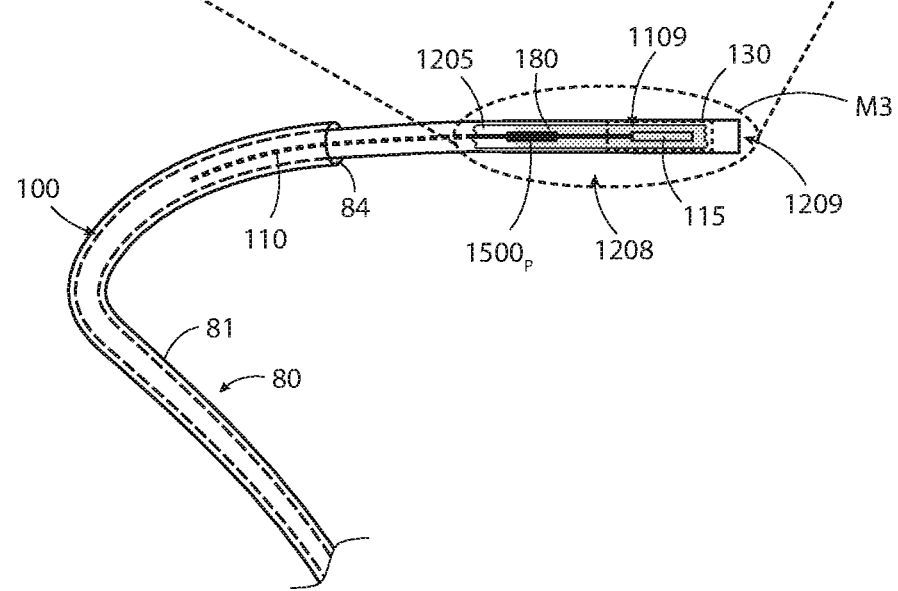

Referring now to FIGS. 4 and 4A, a schematic view of the distal portion of an imaging probe and delivery catheter, and a magnified view of the components within circle M3, are illustrated, respectively, consistent with the present inventive concepts. Imaging probe 100 of FIGS. 4 and 4A can comprise similar components and be of similar construction and arrangement to imaging probe 100 of FIG. 1 described hereabove. Imaging probe 100 of FIGS. 4 and 4A comprises a pressurization element with a propeller-like construction, FPE $1500_P$. FPE $1500_P$ can comprise one, or more radial projections 1501 extending from optical core 110. Projections 1501 comprise a profile configured to propel fluid when optical core 110 is rotated, similar to propeller blades. FPE $1500_P$ can be configured to produce a pressure gradient within gel 180 as described hereabove.

Figure 5A:
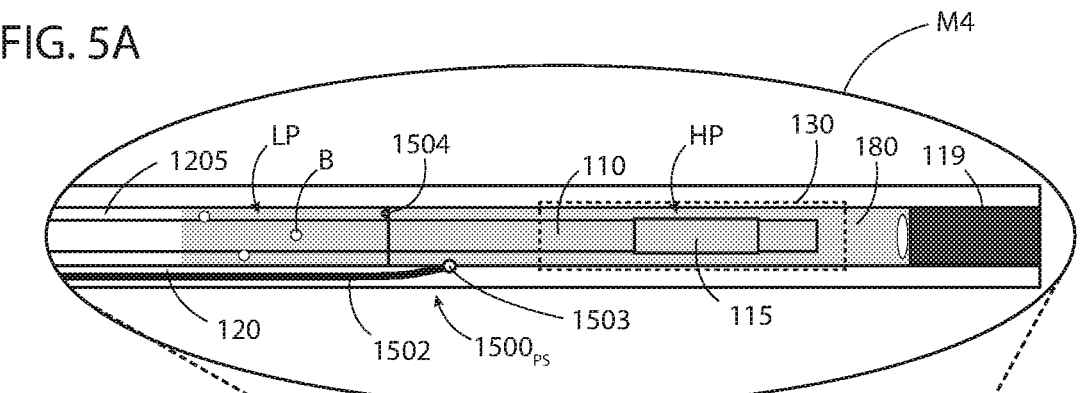
FIGS. 5 and 5A illustrate a schematic view of the distal portion of an imaging probe and delivery catheter, and a magnified view of the components within circle M4, respectively, consistent with the present inventive concepts.
Figure 5:
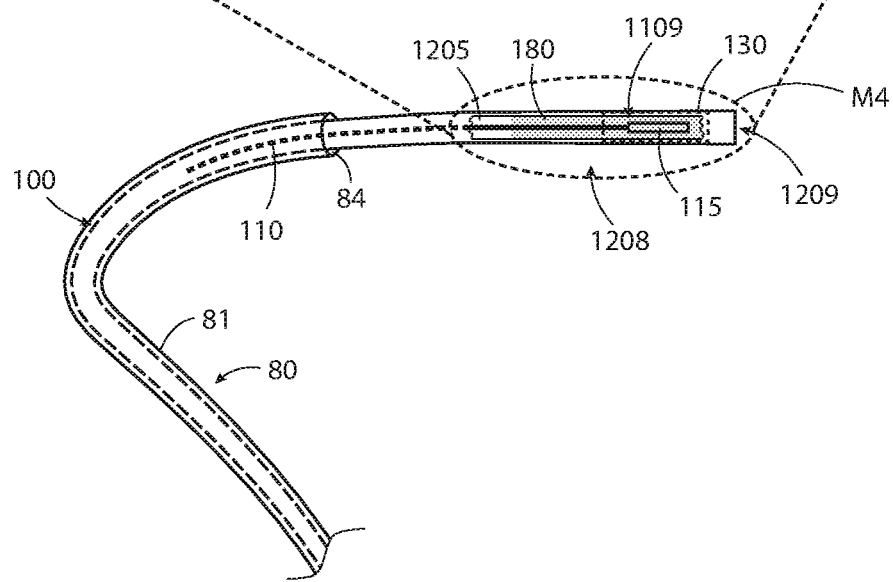

Referring now to FIGS. 5 and 5A, a schematic view of the distal portion of an imaging probe and delivery catheter, and a magnified view of the components within circle M4, are illustrated, respectively, consistent with the present inventive concepts. Imaging probe 100 of FIGS. 5 and 5A can comprise similar components and be of similar construction and arrangement to imaging probe 100 of FIG. 1 described hereabove. Imaging probe 100 of FIGS. 5 and 5A comprises a pressurization element comprising a pump, FPE $1500_{PS}$. FPE $1500_{PS}$ can comprise a fluid lumen 1502, with an exit port 1503, exiting into lumen 1205 proximal to optical assembly 115. Lumen 1205 can be fluidly attached to a pump, not shown, but such as a pump within console 50 of FIG. 1. The pump can be configured to apply a pressure to gel 180 via FPE $1500_{PS}$ prior to, during, and/or after an imaging procedure. FPE $1500_{PS}$ can further comprise a fluid restriction element, valve 1504. Valve 1504 is shown positioned proximal to exit port 1503 within lumen 1205. Valve 1504 can be configured to limit the flow of fluid (e.g. gel 180) proximally within lumen 1205, such that FPE $1500_{PS}$ can generate an increased pressure of gel 180 at locations distal to valve 1504. Valve 1504 can be configured to allow the passage of air and/or other gas (e.g. bubbles B described herein), while limiting the passage of gel 180 (e.g. due to the viscosity and/or molecular size of gel 180). FPE $1500_{PS}$ can be configured to produce a pressure gradient within gel 180 as described hereabove in reference to FIGS. 1 and 1A.

Figure 6A:
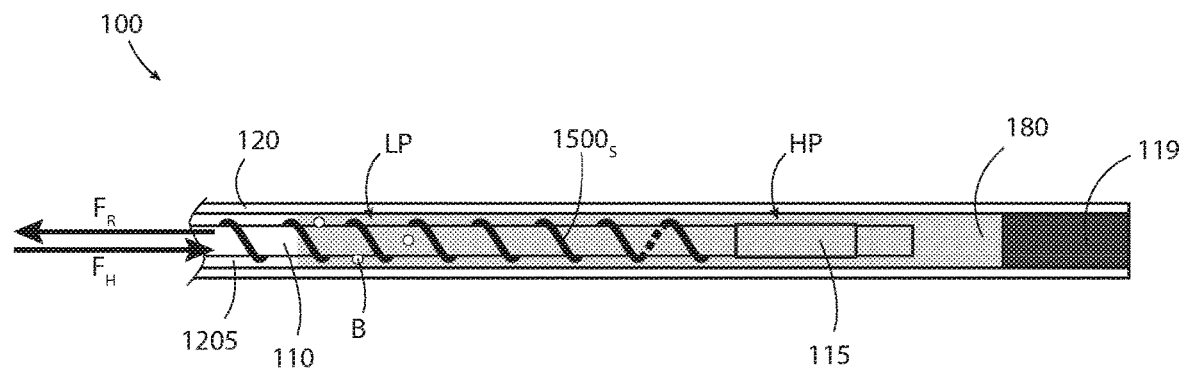
FIG. 6A-C illustrate schematic views of the distal portion of an optical probe, consistent with the present inventive concepts.
Figure 6B:
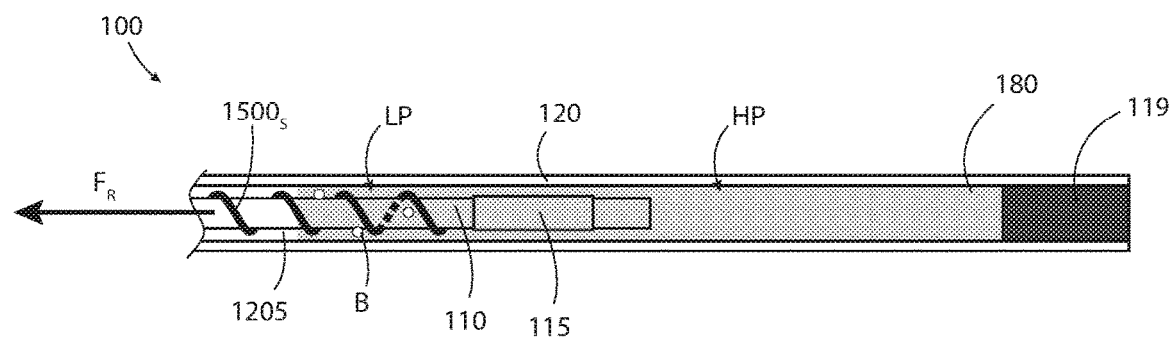
Figure 6C:
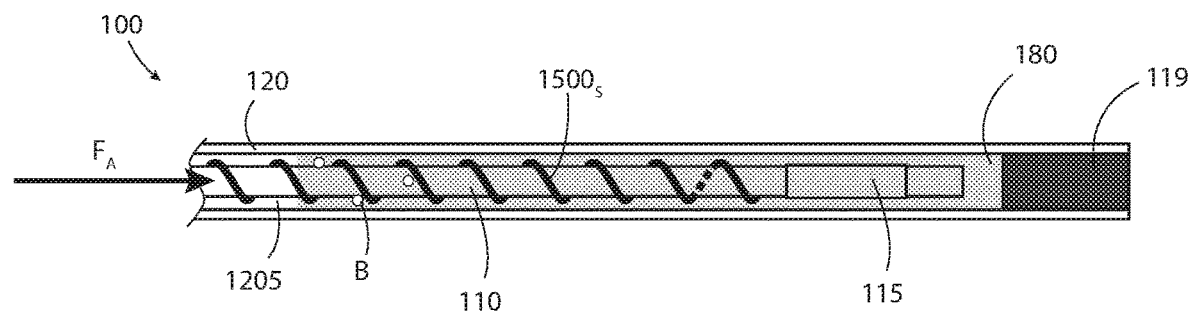

Referring now to FIGS. 6A, 6B, and 6C, sectional views of the distal portion of an optical probe are illustrated, consistent with the present inventive concepts. Imaging probe 100 can be of similar construction and arrangement to imaging probe 100 described hereabove in reference to FIGS. 1 and 1A. In some embodiments, optical core 110 is configured to be retracted and advanced within shaft 120, as shown in FIGS. 6A-C. Optical core 110 can be retracted via linkage 856, which is operably attached to a proximal portion of optical core 110 (as shown in FIG. 1 hereabove). A fluid pressurization element optically coupled to optical core 110 can comprise a spring-type element, FPE $1500_S$, such as described hereabove in reference to FIGS. 2-3B. FPE $1500_S$ can be configured to generate a pressure gradient from a low pressure area LP to a high pressure area HP within gel 180, such as is described hereabove. In some embodiments, when optical core 110 is retracted within shaft 120, the retraction can cause voids (e.g. one or more air bubbles formed due to a pressure drop caused by the retraction of optical core 110) within gel 180. FPE $1500_S$ can be configured to minimize the creation of these voids by producing the pressure gradient within gel 180 while optical core 110 is rotated and retracted. Additionally or alternatively, FPE $1500_S$ can be configured to produce a motive force, configured to drive at least the distal end of optical core 110 longitudinally (e.g. translate proximally and/or distally) within lumen 1205 of shaft 120.

FPE $1500_S$ can be configured to generate both a motive force and a pressure gradient within gel 180, causing one or more resulting scenarios, as illustrated in FIGS. 6A-C. In FIG. 6A, as optical core 110 is rotated in a first direction (such that FPE $1500_S$ propels gel 180 distally), a retracting force FR is exerted on optical core 110 and a pressure gradient is generated from low pressure area LP to high pressure area HP. Optical core 110 can be held in place by a holding force FH, such as a force exerted from retraction assembly 800 as described hereabove in reference to FIG. 1. In this state, optical core 110 does not travel longitudinally (e.g. proximally and/or distally) within shaft 120.

As shown in FIG. 6B, when holding force FH is removed, force FR acts to retract at least a distal portion of optical core 110 within shaft 120. In some embodiments, retraction assembly 800 also applies a retraction force to optical core 110. Force FR can be configured to limit the stress applied to optical core 110 while a retraction force is applied from a proximal portion, by assisting the retraction of optical core 110 within shaft 120.

In some embodiments, as shown in FIG. 6C, optical core 110 (and FPE $1500_S$) can be rotated in a second direction (e.g. opposite the first direction), such that FPE $1500_S$ drives gel 180 proximally, applying an advancing force FA to optical core 110. In some embodiments, retraction assembly 800 can apply an advancing force to a proximal portion of optical core 110. Force FA can be configured to limit and/or prevent kinking of optical core 110 within shaft 120 by applying force FA (a pulling force) to a distal portion of optical core 110 while retraction assembly 800 applies a pushing force to a proximal portion.

Figure 7:
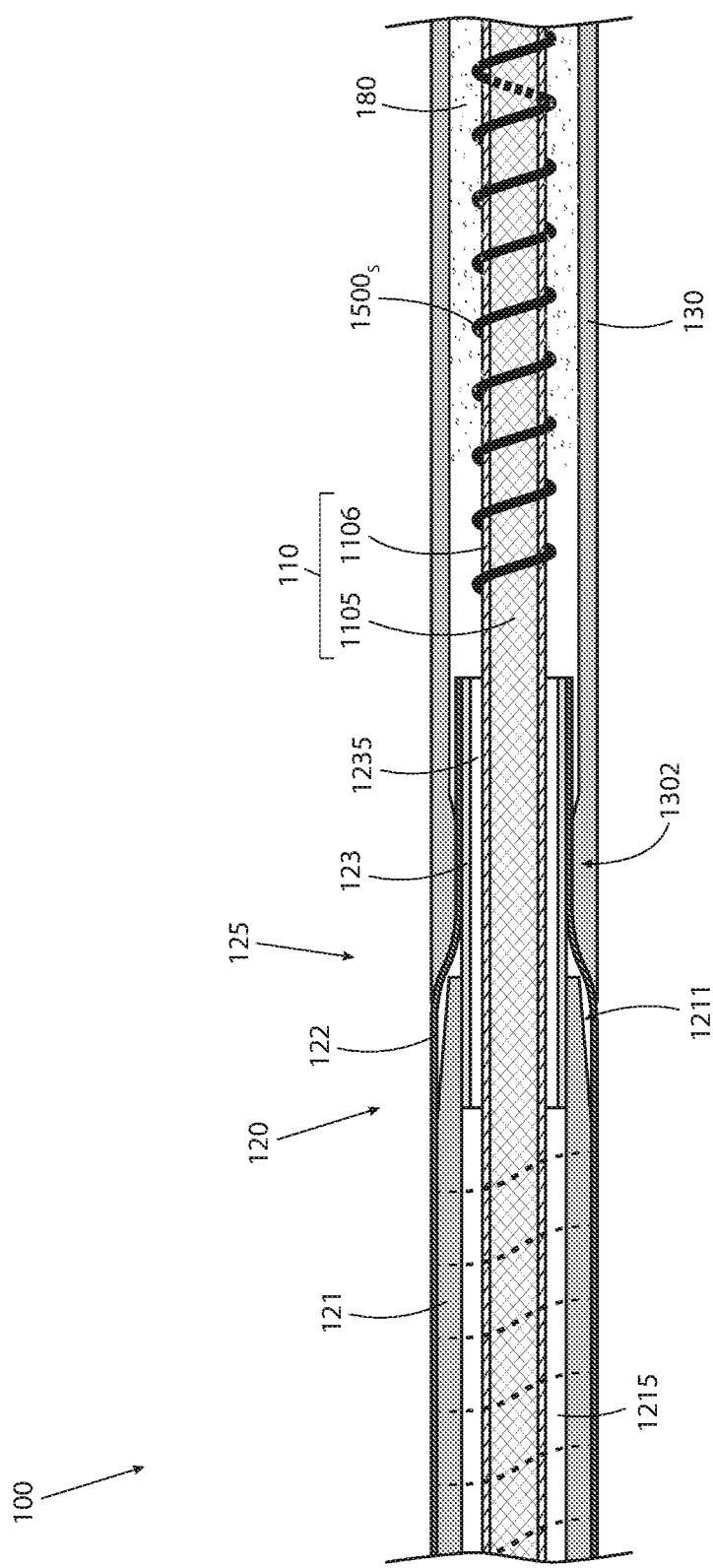
FIG. 7 illustrates a sectional view of a segment of an imaging probe comprising a shaft with a multi-component construction, consistent with the present inventive concepts.

Referring now to FIG. 7, a sectional view of a segment of an imaging probe comprising a shaft with a multi-component construction is illustrated, consistent with the present inventive concepts. Imaging probe 100 of the present inventive concepts can comprise a shaft constructed with multiple components, such as the components of shaft 120 shown in FIG. 7. Shaft 120 can comprise at least a first (proximal) portion, tube 121, fixedly attached, via joint 125, to a second (distal) portion, window 130. Tube 121 can comprise an elongate hollow member, such as a hypotube (e.g. a metal tube that can include one or more engineered features along its length). In some embodiments, tube 121 comprises a hypotube including a spiral cut along at least a portion of its length. In some embodiments, tube 121 comprises nickel titanium alloy (e.g. Nitinol). In some embodiments, tube 121 comprises a plastic material, such as polyimide or PEEK. In some embodiments, window 130 comprises a transparent elongate hollow member, such as is described hereabove in reference to FIG. 1.

Joint 125 can comprise at least the distal portion of tube 121 and at least the proximal portion of window 130. The distal portion of tube 121 can comprise a tapered portion, taper 1211. Taper 1211 can be configured such that the outer diameter of tube 121 decreases from the proximal end of taper 1211 to the distal end of taper 1211. Tube 121 comprises a lumen 1215 therethrough. An elongate segment, tube 123, is partially inserted into lumen 1215 of tube 121. Tube 123 can comprise an outer diameter approximately equal to the diameter of lumen 1215. In some embodiments, tube 123 comprises an outer diameter slightly greater than the diameter of lumen 1215 (e.g. such that tube 123 can be press fit into lumen 1215), or tube 123 comprises a diameter equal to or slightly smaller than the diameter of lumen 1215 (e.g. such as to provide space for an adhesive between tube 125 and tube 121). Tube 123 comprises a lumen 1235 therethrough. In some embodiments, lumen 1235 comprises a diameter greater than the outer diameter of optical core 110 (e.g. such that optical core 110 can be slidingly positioned therethrough). Additionally or alternatively, lumen 1235 can comprise a diameter (e.g. tube 123 comprises an inner diameter) that is less than the outer diameter of FPE $1500_S$, such that FPE $1500_S$ cannot translate proximally beyond tube 123 (e.g. translation of FPE $1500_S$ proximally causes FPE $1500_S$ to contact the end of tube 123, preventing FPE $1500_S$ from entering lumen 1235).

Joint 125 can further comprise an overtube 122, configured to surround at least the distal portion of tube 121 and at least a portion of tube 123 (e.g. at least a portion of tube 123 extending distally from lumen 1215). Overtube 122 can comprise a "heat shrink" material, (e.g. a material configured to contract when heat is applied). In these embodiments, overtube 122 can comprise a first diameter (e.g. a pre-shrunk diameter) equal to or greater than the outer diameter of tube 121, such that tube 121 can be slidingly received within overtube 122. After overtube 122 is positioned relative to tubes 121 and 123, heat can be applied such that overtube 122 shrinks and conforms to the outer profile of tubes 121 and 123. Additionally or alternatively, overtube 122 can comprise an elastic material. In some embodiments, overtube 122 can comprise an elastic material and an inner diameter less than or equal to the outer diameter of tube 123. In these embodiments, overtube 122 can be positioned about tubes 121 and 123 by stretching overtube 122 to slidingly receive tubes 121 and 123, such that overtube 122 contracts after positioning to conform to the outer profile of tubes 121 and 123. In some embodiments, overtube 122 can be "rolled" onto tubes 121 and 123, such that overtube 122 both stretches and conforms as it is rolled over tubes 121 and 123. Overtube 122 can comprise PET.

The proximal portion of window 130 can comprise an inward radial projection 1302. Radial projection 1302 can comprise an inner diameter constructed and arranged to match the outer diameter of tubes 123 and 122 (e.g. the outer diameter of tube 122 compressed about tube 123). In some embodiments, window 130 does not include radial projection 1302, and the inner diameter of window 130 is constructed and arranged to match the outer diameter of tubes 123 and 122. In some embodiments, the proximal portion of window 130 slidingly receives the distal portion of tubes 122 and 123. The proximal portion of window 130 can further slidingly receive at least a distal portion of taper 1211 of tube 121. Window 130 can be fixedly attached to tubes 121, 122, and/or 123 via compression and/or an adhesive. In some embodiments, the outer surface of overtube 122 can be prepared (e.g. mechanically or chemically prepared) for adhesion to window 130, for example via a chemical primer. In some embodiments, the proximal end of window 130 is "shrunk" onto tubes 121, 122, and/or 123 to provide a compression fit. In some embodiments, window 130 comprises a material configured to contract when under tension (e.g. when window 130 is pulled, intentionally or unintentionally away from tube 121), such that window 130 compresses onto tubes 121, 122, and/or 123, strengthening joint 125 when under tension. In these embodiments, tubes 121, 122, and/or 123 can comprise a lower modulus than window 130, such that window 130 compresses more under equal tension than one or more of tubes 121, 122, and/or 123.

In some embodiments, joint 125 comprises a maximum outer diameter of no more than 0.02", such as no more than 0.0175", such as less than or equal to 0.0155". In some embodiments, joint 125 comprises a tensile strength of at least 2 N, such as at least 2.6 N, such as at least 5.5 N, such as at least 6 N. In some embodiments, the distal portion of imaging probe 100 (including joint 125 and at least a distal segment of tube 121, for example the distal 30 cm of imaging probe 100) comprises a minimum bend radius of no more than 5 mm, such as no more than 4 mm, no more than 3 mm, or no more than 2.5 mm.

In some embodiments, optical core 110 can comprise two or more layers (e.g. two or more concentric layers), such as a core 1105, which can be surrounded by one or more layers of cladding, cladding 1106.

Figure 8:
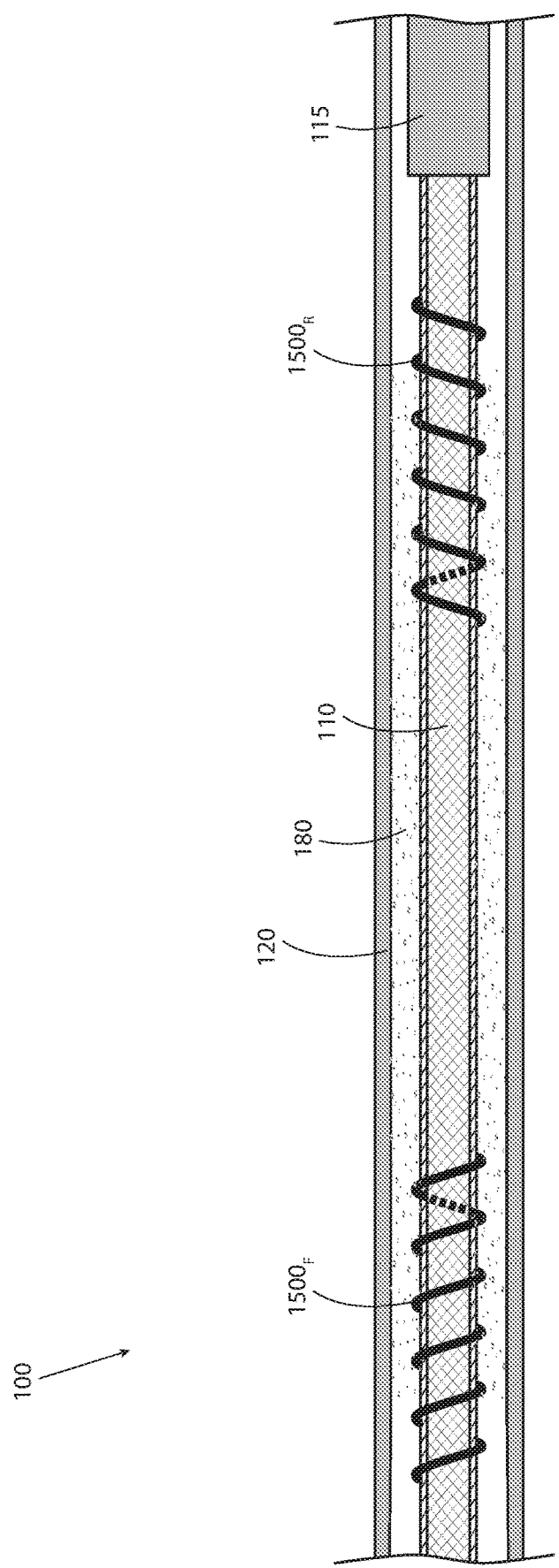
FIG. 8 illustrates a sectional view of a portion of an imaging probe comprising a bidirectional fluid propulsion element, consistent with the present inventive concepts.

Referring now to FIG. 8, a sectional view of a portion of an imaging probe comprising a bidirectional fluid propulsion element is illustrated, consistent with the present inventive concepts. Imaging probe 100 of FIG. 8 can comprise similar components and be of similar construction and arrangement to imaging probe 100 of FIG. 1 described herein. Imaging probe 100 of FIG. 8 comprises two fluid propulsion elements, FPE $1500_F$ and $1500_R$. In some embodiments, FPE $1500_F$ can be positioned proximal to FPE $1500_R$ as shown in FIG. 8. FPE $1500_F$ can be configured to propel gel 180 distally towards FPE $1500_R$ when optical core 110 is rotated in a first direction, such as is described herein. FPE $1500_R$ can be configured to propel gel 180 proximally, towards FPE $1500_F$, when optical core 110 is also rotated in the first direction (e.g. when FPE $1500_F$ and $1500_R$ are rotated in the same direction, they propel gel 180 in opposite directions). In this manner, FPE $1500_F$ and $1500_R$ are configured to maintain gel 180 between each other (e.g. to create a confined region of pressurized gel 180 between the two elements). In some embodiments, as optical core 110 is advanced and/or retraced within shaft 120, FPE $1500_F$ and $1500_R$ are configured to propel gel 180 to translate with optical core 110 (e.g. remain between FPE $1500_F$ and $1500_R$ as the FPEs are translated with optical core 110). In some embodiments, the rotation of optical core 110 can be reversed, causing gel 180 to be at least partially evacuated from the region between FPE $1500_F$ and $1500_R$.

Figure 9A:
FIGS. 9A-D illustrate perspective views of four steps of a process for manufacturing a fluid propulsion element, consistent with the present inventive concepts.
Figure 9B:
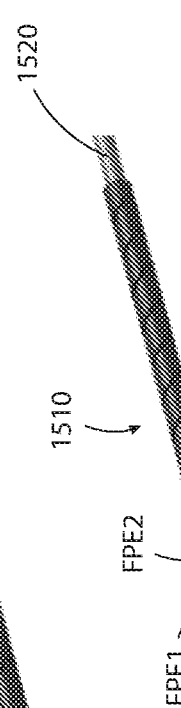
Figure 9C:
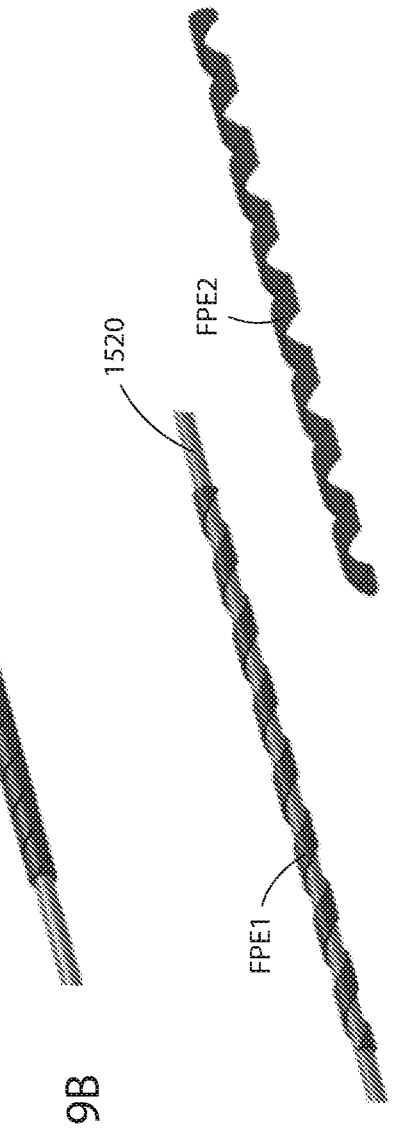
Figure 9D:
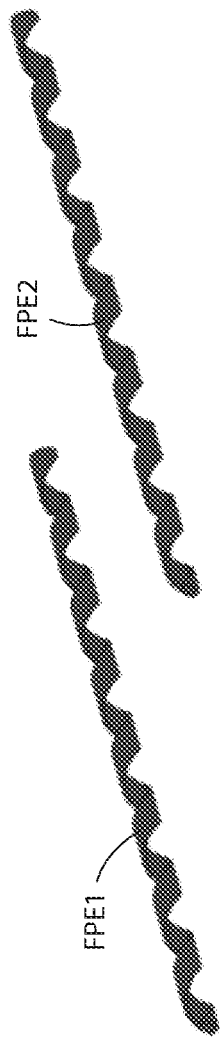

Referring now to FIGS. 9A-D, perspective views of four steps of a process for manufacturing a fluid propulsion element are illustrated, consistent with the present inventive concepts. FIG. 9A illustrates a tube 1510 (e.g. a polyimide tube) surrounding a mandrel 1520. A helical channel has been cut (e.g. laser cut) into tube 1510 (e.g. after mandrel 1520 was inserted into tube 1510). In FIG. 9B, mandrel 1520 has been rotated 180°, and a second helical channel has been cut, separating tube 1510 into a first fluid propulsion element FPE1, and a second fluid propulsion element FPE2, each surrounding mandrel 1520 (e.g. two similar or dissimilar FPE $1500_S$). In FIG. 9C, FPE2 has been removed from mandrel 1520, for example FPE2 has been peeled off of mandrel 1520. In FIG. 9D, FPE1 has also been removed from mandrel 1520 (e.g. peeled off or slid off of mandrel 1520). The illustrated process provides two fluid propulsion elements of the present inventive concepts, such as for use in a single optical probe 100 comprising two FPE $1500_S$, and/or for use in two optical probes 100, each comprising a single FPE 1500. In this process, each of FPE1 and FPE2 can comprise matching dimensions, for example when the coil spacing equals the coil width of each FPE. In some embodiments, three or more slits can be made in tube 1510, such as to produce three or more FPE $1500_S$.

The above-described embodiments should be understood to serve only as illustrative examples; further embodiments are envisaged. Any feature described herein in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the inventive concepts, which is defined in the accompanying claims.

What is claimed is:

1. An imaging system for a patient comprising:
    an imaging probe, comprising:
        an elongate shaft comprising a proximal end, a distal portion, and a lumen extending between the proximal end and the distal portion;
        a rotatable optical core comprising a proximal end and a distal end, wherein at least a portion of the rotatable optical core is positioned within the lumen of the elongate shaft;
        an optical assembly positioned proximate the distal end of the rotatable optical core, the optical assembly configured to direct light to tissue and collect reflected light from the tissue;
        a damping fluid positioned between the elongate shaft and the rotatable optical core and configured to reduce non-uniform rotation of the optical assembly; and
        a fluid pressurization element configured to increase the pressure of the damping fluid to reduce the presence of bubbles proximate the optical assembly;
        an imaging assembly constructed and arranged to optically couple to the imaging probe, the imaging assembly configured to emit light into the imaging probe and receive the reflected light collected by the optical assembly;
        wherein the damping fluid comprises a fluid with high surface tension configured to reduce bubble formation.

2. The system as claimed in claim 1, wherein the fluid pressurization element is configured to reduce bubble formation.

3. The system as claimed in claim 1, wherein the fluid pressurization element is configured to reduce the size of one or more bubbles.

4. The system as claimed in claim 1, wherein the system comprises an optical beam path, and wherein the fluid pressurization element is configured to propel one or more bubbles to a location remote from the optical beam path.

5. The system as claimed in claim 1, wherein the fluid pressurization element is configured to create a pressure gradient within the damping fluid.

6. The system as claimed in claim 1, wherein the fluid pressurization element is configured to generate a pressure of the damping fluid of at least: 3.6 psi; 5.0 psi; 10 psi; 15 psi; 20 psi; 30 psi; 40 psi; 75 psi; 100 psi; 125 psi; and/or 150 psi.

7. The system as claimed in claim 1, wherein the fluid pressurization element is configured to increase the pressure of the damping fluid when the rotatable optical core is rotated.

8. The system according to claim 7, wherein the fluid pressurization element comprises a helical projection that radially extends from the rotatable optical core.

9. The system as claimed in claim 1, wherein the fluid pressurization element comprises a first fluid pressurization element and a second fluid pressurization element, and wherein the second fluid pressurization element is positioned proximal to the first fluid pressurization element.

10. The system according to claim 9, wherein the second fluid pressurization element is configured to prime the first fluid pressurization element when rotated.

11. The system as claimed in claim 1, wherein the fluid pressurization element comprises a material selected from the group consisting of:
   metal; plastic; stainless steel; nickel-titanium alloy; nylon; polyether ether ketone;
   polyimide; and combinations thereof.

12. The system as claimed in claim 1, wherein the rotatable optical core comprises a diameter D1, wherein the elongate shaft lumen comprises a diameter $D_2$, wherein the fluid pressurization element extends from the rotatable optical core with a radial height H1, and wherein H1 comprises at least 5% and/or no more than 95% of half the difference between D1 and $D_2$.

13. The system as claimed in claim 1, wherein the rotatable optical core comprises a diameter D1, wherein the elongate shaft lumen comprises a diameter $D_2$, wherein the fluid pressurization element extends from the rotatable optical core with a radial height H1, wherein a clearance C1 comprises one half the difference between D1 and $D_2$ minus H1, and wherein clearance C1 comprises a length of no more than 100 μm and/or no more than 75 um.

14. The system as claimed in claim 1, wherein the damping fluid comprises a shear-thinning fluid.

15. The system as claimed in claim 1, wherein the damping fluid comprises a low viscosity fluid configured to reduce bubble formation.

16. The system according to claim 15, wherein the damping fluid comprises a fluid with a viscosity of no more than 1000 centipoise.

17. The system according to claim 1, wherein the damping fluid comprises a fluid with a surface tension of at least 40 dynes/cm.

18. The system as claimed in claim 1, wherein the imaging probe comprises a distal portion with a diameter of no more than 0.020".

19. The system according to claim 18, wherein the imaging probe distal portion comprises a diameter of no more than 0.016".

20. The system as claimed in claim 1, wherein the imaging probe further includes a sealing element in a distal portion of the elongate shaft.

21. An imaging system for a patient comprising:
   an imaging probe, comprising:
      an elongate shaft comprising a proximal end, a distal portion, and a lumen extending between the proximal end and the distal portion;
      a rotatable optical core comprising a proximal end and a distal end, wherein at least a portion of the rotatable optical core is positioned within the lumen of the elongate shaft;
      an optical assembly positioned proximate the distal end of the rotatable optical core, the optical assembly configured to direct light to tissue and collect reflected light from the tissue;
      a damping fluid positioned between the elongate shaft and the rotatable optical core and configured to reduce non-uniform rotation of the optical assembly; and
      a fluid pressurization element configured to increase the pressure of the damping fluid to reduce the presence of bubbles proximate the optical assembly;
   an imaging assembly constructed and arranged to optically couple to the imaging probe, the imaging assembly configured to emit light into the imaging probe and receive the reflected light collected by the optical assembly;
   wherein the fluid pressurization element is configured to increase the pressure of the damping fluid intermittently, and
   wherein the fluid pressurization element is configured to increase the pressure of the damping fluid for discrete time periods of no more than five seconds.

22. An imaging system for a patient comprising:
   an imaging probe, comprising:
      an elongate shaft comprising a proximal end, a distal portion, and a lumen extending between the proximal end and the distal portion;
      a rotatable optical core comprising a proximal end and a distal end, wherein at least a portion of the rotatable optical core is positioned within the lumen of the elongate shaft;
      an optical assembly positioned proximate the distal end of the rotatable optical core, the optical assembly configured to direct light to tissue and collect reflected light from the tissue;
      a damping fluid positioned between the elongate shaft and the rotatable optical core and configured to reduce non-uniform rotation of the optical assembly; and
      a fluid pressurization element configured to increase the pressure of the damping fluid to reduce the presence of bubbles proximate the optical assembly;
   an imaging assembly constructed and arranged to optically couple to the imaging probe, the imaging assembly configured to emit light into the imaging probe and receive the reflected light collected by the optical assembly;
   wherein the fluid pressurization element is adhesively attached to the rotatable optical core.

23. An imaging system for a patient comprising:
   an imaging probe, comprising:
      an elongate shaft comprising a proximal end, a distal portion, and a lumen extending between the proximal end and the distal portion;
      a rotatable optical core comprising a proximal end and a distal end, wherein at least a portion of the rotatable optical core is positioned within the lumen of the elongate shaft;
      an optical assembly positioned proximate the distal end of the rotatable optical core, the optical assembly configured to direct light to tissue and collect reflected light from the tissue;
      a damping fluid positioned between the elongate shaft and the rotatable optical core and configured to reduce non-uniform rotation of the optical assembly; and
      a fluid pressurization element configured to increase the pressure of the damping fluid to reduce the presence of bubbles proximate the optical assembly:
   an imaging assembly constructed and arranged to optically couple to the imaging probe, the imaging assembly configured to emit light into the imaging probe and receive the reflected light collected by the optical assembly;
   wherein the fluid pressurization element is formed into the rotatable optical core, and;

wherein the system is formed onto the rotatable optical core via deposition and/or three-dimensional (3D) printing.

24. An imaging system for a patient comprising:

an imaging probe, comprising:

an elongate shaft comprising a proximal end, a distal portion, and a lumen extending between the proximal end and the distal portion;

a rotatable optical core comprising a proximal end and a distal end, wherein at least a portion of the rotatable optical core is positioned within the lumen of the elongate shaft;

an optical assembly positioned proximate the distal end of the rotatable optical core, the optical assembly configured to direct light to tissue and collect reflected light from the tissue;

a damping fluid positioned between the elongate shaft and the rotatable optical core and configured to reduce non-uniform rotation of the optical assembly; and a fluid pressurization element configured to increase the pressure of the damping fluid to reduce the presence of bubbles proximate the optical assembly:

an imaging assembly constructed and arranged to optically couple to the imaging probe, the imaging assembly configured to emit light into the imaging probe and receive the reflected light collected by the optical assembly;

wherein the damping fluid comprises a static viscosity of at least 500 centipoise, and wherein the damping fluid comprises a static viscosity to shear viscosity ratio of at least 1.2:1 and/or no more than 100:1.

* * * * *